US012637413B2

(12) United States Patent
Stearns et al.

(10) Patent No.: US 12,637,413 B2
(45) Date of Patent: May 26, 2026

(54) FATTY ACID AMIDE HYDROLASE (FAAH) CLEAVABLE PRODRUGS OF THYROMIMETICS AND COMBINATION WITH PERIPHERALLY RESTRICTED FAAH INHIBITORS

(71) Applicant: Autobahn Therapeutics, Inc., San Diego, CA (US)

(72) Inventors: Brian Andrew Stearns, San Diego, CA (US); Jill Melissa Baccei, San Diego, CA (US); Jason Randall Harris, San Diego, CA (US)

(73) Assignee: AUTOBAHN THERAPEUTICS, INC., San Diego, CA (US)

( * ) Notice: Subject to any disclaimer, the term of this patent is extended or adjusted under 35 U.S.C. 154(b) by 386 days.

(21) Appl. No.: 18/558,726

(22) PCT Filed: May 6, 2022

(86) PCT No.: PCT/US2022/028187

§ 371 (c)(1),
(2) Date: Nov. 2, 2023

(87) PCT Pub. No.: WO2022/236133

PCT Pub. Date: Nov. 10, 2022

(65) Prior Publication Data

US 2024/0254075 A1 Aug. 1, 2024

Related U.S. Application Data

(60) Provisional application No. 63/274,856, filed on Nov. 2, 2021, provisional application No. 63/185,254, filed on May 6, 2021.

(51) Int. Cl.

| | |
|---|---|
| ***C07D 205/04*** | (2006.01) |
| ***A61K 31/16*** | (2006.01) |
| ***A61K 31/165*** | (2006.01) |
| ***A61K 31/397*** | (2006.01) |
| ***A61K 31/40*** | (2006.01) |
| ***A61K 31/42*** | (2006.01) |
| ***A61K 31/44*** | (2006.01) |
| ***A61K 31/4406*** | (2006.01) |
| ***A61K 31/4409*** | (2006.01) |
| ***A61K 31/455*** | (2006.01) |
| ***A61K 31/4965*** | (2006.01) |
| ***A61K 31/50*** | (2006.01) |
| ***A61K 31/505*** | (2006.01) |
| ***A61K 31/5375*** | (2006.01) |
| ***A61P 25/00*** | (2006.01) |
| ***C07C 235/16*** | (2006.01) |
| ***C07C 235/20*** | (2006.01) |
| ***C07C 235/22*** | (2006.01) |
| ***C07C 235/24*** | (2006.01) |
| ***C07C 243/28*** | (2006.01) |
| ***C07C 255/29*** | (2006.01) |
| ***C07C 259/06*** | (2006.01) |
| ***C07C 313/02*** | (2006.01) |

(Continued)

(52) U.S. Cl.

CPC ............ *C07C 235/20* (2013.01); *A61K 31/16* (2013.01); *A61K 31/165* (2013.01); *A61K 31/397* (2013.01); *A61K 31/40* (2013.01); *A61K 31/42* (2013.01); *A61K 31/44* (2013.01); *A61K 31/4406* (2013.01); *A61K 31/4409* (2013.01); *A61K 31/455* (2013.01); *A61K 31/4965* (2013.01); *A61K 31/50* (2013.01); *A61K 31/505* (2013.01); *A61K 31/5375* (2013.01); *A61P 25/00* (2018.01); *C07C 235/16* (2013.01); *C07C 235/22* (2013.01); *C07C 235/24* (2013.01); *C07C 243/28* (2013.01); *C07C 255/29* (2013.01); *C07C 259/06* (2013.01); *C07C 313/02* (2013.01); *C07C 317/28* (2013.01); *C07D 205/04* (2013.01); *C07D 213/75* (2013.01); *C07D 237/20* (2013.01); *C07D 237/22* (2013.01); *C07D 239/42* (2013.01); *C07D 241/20* (2013.01); *C07D 261/14* (2013.01); *C07D 295/18* (2013.01); *C07D 305/08* (2013.01); *C07C 2601/02* (2017.05); *C07C 2601/14* (2017.05)

(58) Field of Classification Search

CPC .................................................... C07D 205/04

See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |

(Continued)

FOREIGN PATENT DOCUMENTS

| | | | |
|---|---|---|---|
| CN | 1882327 | A | 12/2006 |
| CN | 101180097 | A | 5/2008 |

(Continued)

OTHER PUBLICATIONS

Actis et al., Small molecule inhibitors of PCNA/PIP-box interaction suppress translesion DNA synthesis. Bioorg Med Chem. 21(7):1972-1977 (2013).

(Continued)

*Primary Examiner* — John S Kenyon

(74) *Attorney, Agent, or Firm* — WILSON SONSINI GOODRICH & ROSATI

(57) ABSTRACT

Provided herein are fatty acid amide (FAAH) cleavable prodrugs of thyromimetics and pharmaceutical compositions comprising these compounds with at least one pharmaceutically acceptable excipient further comprising a peripherally restricted FAAH inhibitor.

20 Claims, 11 Drawing Sheets

(51) Int. Cl.

| | |
|---|---|
| ***C07C 317/28*** | (2006.01) |
| ***C07D 213/75*** | (2006.01) |
| ***C07D 237/20*** | (2006.01) |
| ***C07D 237/22*** | (2006.01) |
| ***C07D 239/42*** | (2006.01) |
| ***C07D 241/20*** | (2006.01) |
| ***C07D 261/14*** | (2006.01) |
| ***C07D 295/18*** | (2006.01) |
| ***C07D 305/08*** | (2006.01) |

(56) References Cited

U.S. PATENT DOCUMENTS

| | | | |
|---|---|---|---|
| 4,652,441 | A | 3/1987 | Okada et al. |
| 4,675,189 | A | 6/1987 | Kent et al. |
| 4,677,191 | A | 6/1987 | Tanaka et al. |
| 4,723,027 | A | 2/1988 | Stoutamire et al. |
| 4,728,721 | A | 3/1988 | Yamamoto et al. |
| 4,741,897 | A | 5/1988 | Andrews et al. |
| 4,917,893 | A | 4/1990 | Okada et al. |
| 4,992,445 | A | 2/1991 | Lawter et al. |
| 5,001,139 | A | 3/1991 | Lawter et al. |
| 5,023,252 | A | 6/1991 | Hseih |
| 5,466,569 | A | 11/1995 | Eber et al. |
| 5,616,345 | A | 4/1997 | Geoghegan et al. |
| 5,883,294 | A | 3/1999 | Scanlan et al. |
| 6,054,485 | A | 4/2000 | Schwartz et al. |
| 6,107,517 | A | 8/2000 | Scanlan et al. |
| 6,236,946 | B1 | 5/2001 | Scanlan et al. |
| 7,288,571 | B2 | 10/2007 | Hangeland et al. |
| 7,302,347 | B2 | 11/2007 | Baxter et al. |
| 7,915,261 | B2 | 3/2011 | Ishii et al. |
| 7,919,494 | B2 | 4/2011 | Ishii et al. |
| 7,919,495 | B2 | 4/2011 | Ishii et al. |
| 9,562,012 | B2 | 2/2017 | Tanis et al. |
| 9,701,650 | B2 | 7/2017 | Scanlan et al. |
| 10,130,643 | B2 | 11/2018 | Cable et al. |
| 10,226,438 | B2 | 3/2019 | Scanlan et al. |
| 10,233,197 | B2 | 3/2019 | Yu |
| 10,392,356 | B2 | 8/2019 | Scanlan et al. |
| 10,544,075 | B2 | 1/2020 | Scanlan et al. |
| 10,870,616 | B2 | 12/2020 | Scanlan et al. |
| 11,104,654 | B2 | 8/2021 | Scanlan et al. |
| 11,325,886 | B2 | 5/2022 | Scanlan et al. |
| 11,510,887 | B2 | 11/2022 | Scanlan et al. |
| 11,578,032 | B2 | 2/2023 | Scanlan |
| 11,613,517 | B2 | 3/2023 | Scanlan et al. |
| 11,667,606 | B2 | 6/2023 | Von Geldern et al. |
| 11,827,596 | B2 | 11/2023 | Von Geldern et al. |
| 2003/0203898 | A1 | 10/2003 | Haning et al. |
| 2003/0215434 | A1 | 11/2003 | Khan et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |
| 2008/0221170 | A1 | 9/2008 | Roberts et al. |
| 2008/0306046 | A1 | 12/2008 | Ishii et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2019/0210950 | A1 | 7/2019 | Scanlan et al. |
| 2020/0181103 | A1 | 6/2020 | Scanlan et al. |
| 2020/0405669 | A1 | 12/2020 | Scanlan et al. |
| 2021/0002208 | A1 | 1/2021 | Scanlan |
| 2021/0087137 | A1 | 3/2021 | Scanlan et al. |
| 2023/0242471 | A1 | 8/2023 | Von Geldern et al. |
| 2023/0242473 | A1 | 8/2023 | Von Geldern et al. |

FOREIGN PATENT DOCUMENTS

| | | | |
|---|---|---|---|
| CN | 101189248 | A | 5/2008 |
| CN | 101547898 | A | 9/2009 |
| CN | 101600450 | A | 12/2009 |
| CN | 101610774 | A | 12/2009 |
| CN | 101848712 | A | 9/2010 |
| CN | 107848940 | A | 3/2018 |
| EP | 3259246 | A1 | 12/2017 |
| JP | H09301917 | A | 11/1997 |
| JP | 2012106996 | A | 6/2012 |
| RU | 2007148927 | A | 7/2009 |
| WO | WO-9321146 | A1 | 10/1993 |
| WO | WO-9900353 | A1 | 1/1999 |
| WO | WO-0039077 | A2 | 7/2000 |
| WO | WO-0073292 | A1 | 12/2000 |
| WO | WO-0160784 | A1 | 8/2001 |
| WO | WO-0190053 | A1 | 11/2001 |
| WO | WO-0200167 | A2 | 1/2002 |
| WO | WO-0234260 | A1 | 5/2002 |
| WO | WO-02072539 | A1 | 9/2002 |
| WO | WO-02081426 | A1 | 10/2002 |
| WO | WO-2004043939 | A1 | 5/2004 |
| WO | WO-2006031922 | A2 | 3/2006 |
| WO | WO-2006128056 | A2 | 11/2006 |
| WO | WO-2006128058 | A2 | 11/2006 |
| WO | WO-2007110226 | A1 | 10/2007 |
| WO | WO-2008125724 | A1 | 10/2008 |
| WO | WO-2013006734 | A1 | 1/2013 |
| WO | WO-2014078892 | A1 | 5/2014 |
| WO | WO-2014178892 | A1 | 11/2014 |
| WO | WO-2014178931 | A1 | 11/2014 |
| WO | WO-2015188015 | A1 | 12/2015 |
| WO | WO-2016134292 | A1 | 8/2016 |
| WO | WO-2017015360 | A1 | 1/2017 |
| WO | WO-2017201320 | A1 | 11/2017 |
| WO | WO-2018032012 | A1 | 2/2018 |
| WO | WO-2018208707 | A1 | 11/2018 |
| WO | WO-2019160980 | A1 | 8/2019 |
| WO | WO-2020118564 | A1 | 6/2020 |
| WO | WO-2020123861 | A1 | 6/2020 |
| WO | WO-2020180624 | A1 | 9/2020 |
| WO | WO-2021108549 | A1 | 6/2021 |
| WO | WO-2022236118 | A1 | 11/2022 |
| WO | WO-2022236133 | A1 | 11/2022 |

OTHER PUBLICATIONS

Alonso-Merino et al., Thyroid hormones inhibit TGF-beta signaling and attenuate fibrotic responses. PNAS USA 113(24):E3451-E3460 (2016).

Ashraf et al., Synthesis, characterization and in vitro hydrolysis studies of ester and amide prodrugs of dexibuprofen. Medicinal Chemistry Research 21:3361-3368 (2012).

Balkwill et al., Smoldering and polarized inflammation in the initiation and promotion of malignant disease. Cancer Cell 7(3):211-217 (2005).

Bastin et al. Salt selection and optimisation procedures for pharmaceutical new chemical entities. Organic Process Research & Development 4(5):427-435 (2000).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4): 154-157 (2004).

(56) References Cited

OTHER PUBLICATIONS

Baxter et al., Selective modulation of thyroid hormone receptor action. J. Steroid Biochem. Mol. Bio. 76:31-42 (2001).
Berge et al. Pharmaceutical Salts. Journal of Pharmaceutical Sciences 66(1): 1-19 (Jan. 1977).
Berkenstam et al., The thyroid hormone mimetic compound KB2115 lowers plasma LDL cholesterol and stimulates bile acid synthesis without cardiac effects in humans. PNAS USA 105(2):663-667 (2008).
Bernal et al., Action of thyroid hormone in brain. J Endocrinol Invest. 25(3):268-288 (2002).
Bernal et al., Thyroid hormone receptors in brain development and function. Nat Clin Pract Endocrinol Metab. 3(3):249-259 (2007).
Bigaud et al., Siponimod penetrates, distributes and acts on the central nervous system: translational insights [abstract No. 3973]. Neurology. 94(15 Suppl) (2020).
Biondi et al., Hypothyroidism as a risk factor for cardiovascular disease. Endocrine 24:1-13 (2004).
Boger et al., Fatty acid amide hydrolase substrate specificity. Bioorg Med Chem Lett. 10(23):2613-2616 (2000).
Borngraeber et al. Ligand Selectivity by Seeking Hydrophobicity in Thyroid Hormone Receptor. PNAS USA 100(26):15358-15363 (2003).
Boymond et al., Preparation of highly functionalized grignard reagents by an iodine-magnesium exchange reaction and its application in solid-phase synthesis. Angew Chem Int Ed Engl. 37(12):1701-1703 (1998).
Buzard et al., Discovery of APD334: design of a clinical stage functional antagonist of the sphingosine-1-phosphate-1 receptor. ACS Med Chem Lett. 5(12):1313-1317 (2014).
Calza et al., Thyroid hormone and remyelination in adult central nervous system: a lesson from an inflammatory-demyelinating disease. Brain Res Brain Res Rev. 48(2):339-346 (2005).
Chiellini et al., A high-affinity subtype-selective agonist ligand for the thyroid hormone receptor. Chemistry and Biology 5(6):299-306 (1998).
Chiellini et al., Synthesis and biological activity of novel thyroid hormone analogues: 5'-aryl substituted GC-1 derivatives. Bioorg Med Chem. 10(2):333-346 (2002).
Clark et al. Retinoic acid receptor-targeted drugs in neurodegenerative disease. Expert Opin Drug Metab Toxicol 16(11):1097-1108 (2020).
Cravatt et al., Supersensitivity to anandamide and enhanced endogenous cannabinoid signaling in mice lacking fatty acid amide hydrolase. Pnas USA 98(16):9371-9376 (2001).
Dell'Acqua et al., Functional and molecular evidence of myelin- and neuroprotection by thyroid hormone administration in experimental allergic encephalomyelitis. Neuropathol Appl Neurobiol. 38(5):454-470 (2012).
Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. PNAS USA 104(39):15490-15495 (2007).
Ferrara et al., A CNS-targeting prodrug strategy for nuclear receptor modulators. J Med Chem. 63(17):9742-9751 (2020).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould. Salt Selection for Basic Drugs. International Journal of Pharmaceutics, Elsevier, Biomedical Division, NL 33(1-3):201-217 (1986) Retrieved on Nov. 1, 1986].
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
International Conference on Harmonization of Technical Requirements for Registration of Pharmaceuticals for Human Use (ICH). Impurities: Guidelines for Residual Solvents Q3C(R6) 40 pages (Nov. 2005).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult CNS. J Neurosci. 32(36):12528-12542 (2012).
Krogsgaard-Larsen et al. Chapter 4: Design and application of prodrugs. Textbook of Drug Designing and Discovery, US, Taylor & Francis Inc (3rd Ed.) (pp. P460-P514).
Lee et al., Drug transporters in the central nervous system: brain barriers and brain parenchyma considerations. Pharmacological Review 53(4):569-596 (2001).
Liberman et al., Pharmaceutical Dosage Forms. Second Edition 1:209-214 (1990).
Lieberman et al., Pharmaceutical Dosage Forms. Marcel Decker (1980).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Mackenna, D. A. et al. P944.03 Feedback control on the pituitary-thyroid hormone axis by thyroid hormone agonists correlates with peripheral exposure as opposed to central exposure and on-target activity. Neuroscience 2021 Conference Nov. 8-11, Nov. 9, 2021.
Mackenna, D. et al. ABX-002: A fatty-acid amide hydrolase (FAAH) activated prodrug enhances functional delivery of a potent TR-β selective thyromimetic to the brain and demonstrated biological activity i models of X-linked Adrenoleukodystrophy (2442). Neurology (Apr. 13, 2021) 96(15):2442. Meeting Info.: Virtual Annual Meeting of the American Academy of Neurology. Apr. 17-22, 2021.
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).

(56) References Cited

OTHER PUBLICATIONS

Martin et al. The proliferating cell nuclear antigen regulates retinoic acid receptor transcriptional activity through direct protein-protein interaction. Nucleic Acids Res. 33(13):4311-21 (2005).
Massague. TGFbeta signalling in context. Nat Rev Mol Cell Biol. 13(10):616-630 (2012).
Meinig et al., Structure-activity relationships of central nervous system penetration by fatty acid amide hydrolase (FAAH)-targeted thyromimetic prodrugs. ACS Med Chem Lett. 10(1):111-116 (2018).
Meinig et al., Targeting fatty-acid amide hydrolase with prodrugs for CNS-selective therapy. ACS Chem Neurosci. 8(11):2468-2476 (2017).
Meng et al., Indole-propionic acid derivatives as potent, S1P3-sparing and EAE efficacious sphingosine-1-phosphate 1 (S1P1) receptor agonists. Bioorg Med Chem Lett. 22(8):2794-2797 (2012).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
Patani et al., Bioisosterism: A Rational Approach In Drug Design. Chemical Reviews. American Chemical Society 96:3147-3176 (1996).
PCT/US2022/028187 International Search Report and Written Opinion dated Jun. 30, 2022.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
PubChem SID 235918886 [ https://pubchem.ncbi.nlm.nih.gov/substance/ 235918886] (2015).
PubChem SID 319635332 [ https://pubchem.ncbi.nlm.nih.gov/substance/319635332 ] (2016).
Reichel et al., The role of blood-brain barrier studies in the pharmaceutical industry. Curr Drug Metab. 7(2):183-203 (2006).
Remington et al., Remington's Pharmaceutical Sciences. Mack Publishing Company. Fifteenth Edition 5 Pages (1975).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
Scanlan. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70:6789-6795 (2014).
Taub et al., Lipid lowering in healthy volunteers treated with multiple doses of MGL-3196, a liver-targeted thyroid hormone receptor-beta agonist. Atherosclerosis 230(2):373-380 (2013).
Tegeli et al. Synthesis and evaluation of amide prodrugs of mefenamic acid. International Journal of Chemical Sciences 12(3):1033-1043.
Thyroid. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/updated Mar. 1, 2021].
Valadares et al. Role of halogen bonds in thyroid hormone receptor selectivity: pharmacophore-based 3D-QSSR studies. J Chem Inf Model 49(11):2606-2616 (2009).
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: A brief review. 3(3):62-64 (2013).
Ye et al., Thyroid receptor ligands. 1. Agonist ligands selective for the thyroid receptor beta1. J Med Chem. 46(9):1580-1588 (2003).
Yen., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).

ABX-002 + PFI

ABX-002

ABX-002A

ABX-002A

ABX-002

ABX-002 + PFI

ABX-002 + GFI

FATTY ACID AMIDE HYDROLASE (FAAH) CLEAVABLE PRODRUGS OF THYROMIMETICS AND COMBINATION WITH PERIPHERALLY RESTRICTED FAAH INHIBITORS

CROSS-REFERENCE

This patent application is a national stage entry of PCT/US2022/028187, filed on May 6, 2022, which claims the benefit of U.S. Provisional Application No. 63/185,254, filed May 6, 2021 and U.S. Provisional Application No. 63/274,856, filed Nov. 2, 2021, each of which is hereby incorporated by reference in its entirety.

BACKGROUND OF THE INVENTION

The blood-brain barrier is composed of tightly linked endothelial cells that limit the passage of pathogens and specific types of small and large molecules from the blood into the brain. This critical protective function also restricts the diffusion of therapeutics into the brain representing a major challenge to the development of new medicines for CNS diseases.

SUMMARY OF THE INVENTION

In one aspect provided herein is a pharmaceutical composition comprising a fatty acid amide hydrolase (FAAH) cleavable prodrug of Formula (I'), or a pharmaceutically acceptable salt or solvate thereof:

Formula (I')

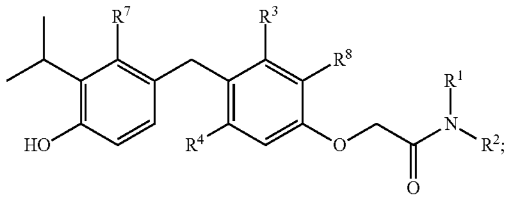

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$;

$R^3$ and $R^4$ are independently selected from —F, —Cl, —Br, and —I;

$R^5$ and $R^6$ are independently selected from hydrogen and $C_1$-$C_6$alkyl; and $R^7$ and $R^8$ are independently selected from hydrogen, —F, —Cl, —Br, and —I; and a pharmaceutically acceptable excipient; further comprising a peripherally restricted FAAH inhibitor.

In some embodiments, $R^7$ is hydrogen. In some embodiments, $R^7$ is —F. In some embodiments, $R^8$ is hydrogen. In some embodiments, $R^8$ is —F.

In another aspect provided herein is a pharmaceutical composition comprising a fatty acid amide hydrolase (FAAH) cleavable prodrug of Formula (I), or a pharmaceutically acceptable salt or solvate thereof:

Formula (I)

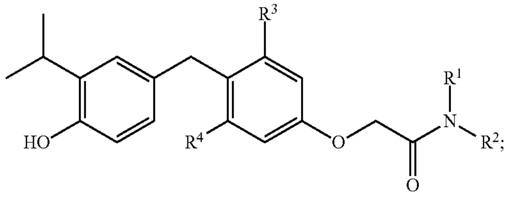

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycl- oalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$;

$R^3$ and $R^4$ are independently selected from —F, —Cl, —Br, and —I; and $R^5$ and $R^6$ are independently selected from hydrogen and $C_1$-$C_6$alkyl;

and a pharmaceutically acceptable excipient; further comprising a peripherally restricted FAAH inhibitor.

In some embodiments, $R^1$ is hydrogen. In some embodiments, $R^2$ is $C_1$-$C_6$alkyl optionally substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more —OH. In some embodiments, $R^2$ is $C_1$-$C_6$alkyl substituted with one or more of halo. In some embodiments, $R^2$ is unsubstituted $C_1$-$C_6$alkyl. In some embodiments, $R^2$ is phenyl optionally substituted with one or more of halo, cyano, —$OR^5$, —$NR^5R^6$, —$S(O)_2R^5$, or —$S(O)_2OR^5$. In some embodiments, $R^2$ is —$C_1$-$C_6$alkyl-phenyl optionally substituted with one or more of halo, cyano, —$OR^5$, —$NR^5R^6$, —$S(O)_2R^5$, or —$S(O)_2OR^5$. In some embodiments, $R^3$ and $R^4$ are independently selected from —F, —Cl, and —Br. In some embodiments, $R^3$ and $R^4$ are both —Br. In some embodiments, $R^3$ and $R^4$ are both —Br. In some embodiments, $R^3$ and $R^4$ are both —Cl. In some embodiments, $R^3$ and $R^4$ are both —F.

In some embodiments, the peripherally restricted FAAH inhibitor is ASP-3652.

In another aspect is a method of treating a CNS disease or disorder in a patient in need thereof comprising administering to the patient a therapeutically effective amount of a pharmaceutical composition described herein. In some embodiments, the CNS disease or disorder is selected from acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (HDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), and Zellweger syndrome. In some embodiments, the CNS disease or disorder is selected from multiple sclerosis and X-linked adrenoleukodystrophy.

BRIEF DESCRIPTION OF THE DRAWINGS

The novel features of the disclosure are set forth with particularity in the appended claims. A better understanding of the features and advantages of the present disclosures will be obtained by reference to the following detailed description that sets forth illustrative embodiments, in which the principles of the disclosures are utilized, and the accompanying drawings of which:

DETAILED DESCRIPTION OF THE INVENTION

Figure 1:
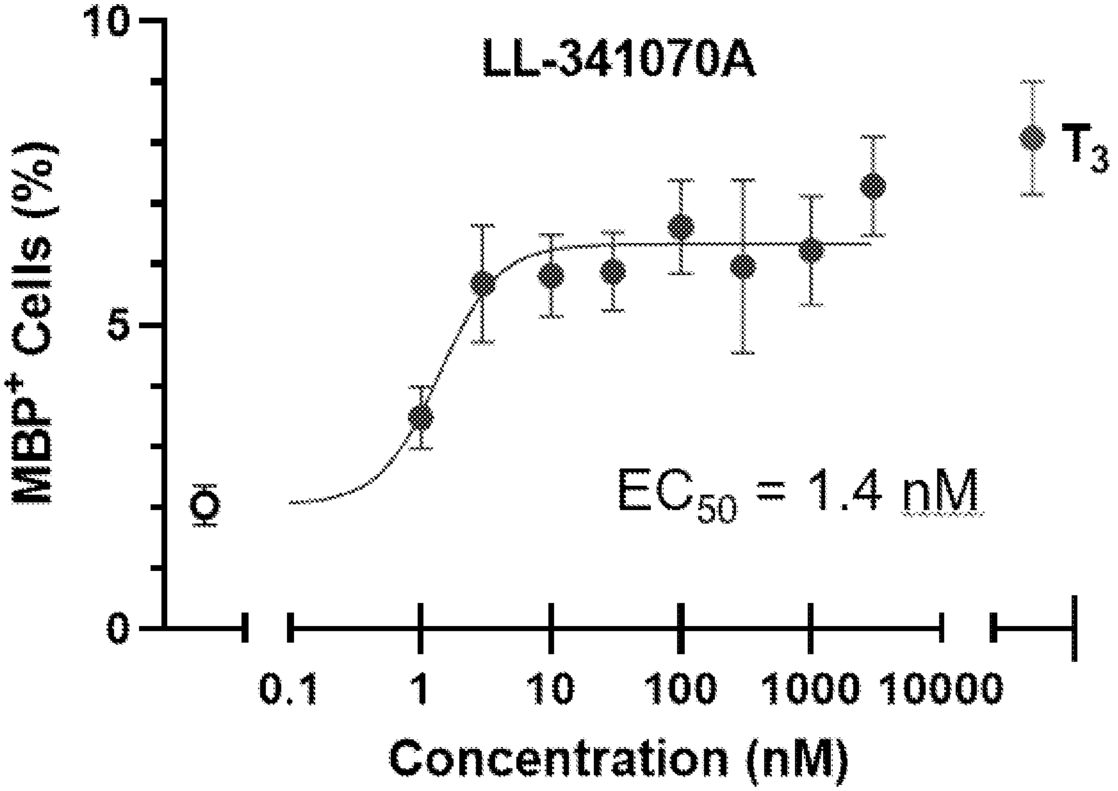
FIG. 1 depicts the active metabolite of the LL-341070 prodrug, LL-341070A, enhanced oligodendrocyte differentiation in vitro in an oligodendrocyte progenitor cell assay.

Fatty acid amide hydrolase (FAAH) is an integral membrane serine hydrolase that degrades the fatty acid amide family of signaling lipids and can hydrolyze select amide prodrugs. FAAH is highly conserved between species and is expressed in many tissues, including the central nervous system (CNS), to varying degrees. Select carboxylic acids can be converted to more permeable amide prodrugs which are then capable of passing through the blood brain barrier where they can be converted to active molecules through the action of FAAH upon the prodrug. This results in the delivery of higher amounts of the carboxylic acid to the CNS as compared to dosing the parent alone. However, peripherally expressed FAAH simultaneously hydrolyzes the prodrug resulting in a considerable amount of non-productive prodrug conversion. Co-administration of a peripherally restricted FAAH inhibitor with a CNS permeable FAAH convertible prodrug increases the selectivity of prodrug delivery to the CNS.

It also results in lower exposures of the parent molecule in plasma and peripheral tissue than what is observed when dosing the prodrug alone.

Candidates for clinical development may be selected from the compounds disclosed herein based on their in vitro FAAH-mediated hydrolysis, in vitro plasma stability, in vivo tissue distribution, in vitro target selectivity, in vitro target potency, target gene expression, in vivo pharmacological efficacy, or degree of drug-like (rule-of-5 compliant) physiochemical properties, or combinations thereof.

Certain Terminology

The singular forms "a," "an," and "the" include plural referents unless the context clearly dictates otherwise. Thus, for example, reference to "a drug" includes reference to one or more of such drugs, and reference to "an excipient" includes reference to one or more of such excipients. When ranges are used herein, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range.

The terms "formulation" and "composition," as used herein, are used interchangeably and refer to a mixture of two or more compounds, elements, or molecules. In some aspects the terms "formulation" and "composition" may be used to refer to a mixture of one or more active agents with a carrier or other excipients.

The terms "active agent," "active pharmaceutical agent," "drug," "active ingredient," and variants thereof are used interchangeably to refer to an agent or substance that has measurable specified or selected physiologic activity when administered to a subject in a significant or effective amount.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), 37 Impurities: Guidelines for Residual Solvents, Q3C(R3), (November 2005). Hydrates are formed when the solvent is water, or alcoholates are formed when the solvent is alcohol.

The terms "effective amount" or "therapeutically effective amount" as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "subject," "individual," and "patient" are used interchangeably herein to refer to a mammal. Mammals include, but are not limited to, murines, simians, humans, farm animals, sport animals, and pets.

The term "peripherally restricted FAAH inhibitor" as used herein, refers to a fatty acid amide hydrolase (FAAH) inhibitor that inhibits FAAH to a greater extent in the periphery than in the central nervous system from a systemic dose. In some embodiments, the peripherally restricted FAAH inhibitor is 60% peripherally restricted. In some embodiments, the peripherally restricted FAAH inhibitor is 70% peripherally restricted. In some embodiments, the peripherally restricted FAAH inhibitor is 80% peripherally restricted. In some embodiments, the peripherally restricted FAAH inhibitor is 90% peripherally restricted. In some embodiments, the peripherally restricted FAAH inhibitor is 95% peripherally restricted.

Target

Thyroid hormone (TH) is a key signal for oligodendrocyte differentiation and myelin formation during development, and also stimulates remyelination in adult models of multiple sclerosis (MS) (Calza L et al, Brain Res Revs 48:339-346, 2005). However, TH is not an acceptable long-term therapy due to there being virtually no therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm J et al, *Mini Rev Med Chem* 7:79-86, 2007). These receptors are expressed in two major forms with heterogenous tissue distributions and overlapping but distinct sets of target genes (Yen P M, Physiol Rev 81:1097-1142, 2001). TRα is enriched in the heart, brain, and bone while TRO is enriched in the liver (O'Shea P J et al, *Nucl Recept Signal* 4:e011, 2006).

Developing selective thyromimetics has been challenging due to the high sequence homology of thyroid hormone receptor subtypes; namely, only one amino acid residue on the internal surface of the ligand binding domain cavity varies between the $\alpha 1$ and $\beta 1$ forms.

In some embodiments, the pharmaceutical compositions described herein comprise a fatty acid amide hydrolase (FAAH) cleavable prodrug of Formula (I'), wherein the prodrug of Formula (I') is a prodrug of a TRO agonist. In some embodiments, the pharmaceutical compositions described herein comprise a fatty acid amide hydrolase (FAAH) cleavable prodrug of Formula (I), wherein the prodrug of Formula (I) is a prodrug of a TRO agonist. In some embodiments, the pharmaceutical compositions described herein comprise a fatty acid amide hydrolase (FAAH) cleavable prodrug of Formula (II), wherein the prodrug of Formula (II) is a prodrug of a TRO agonist.

Pharmaceutical Compositions

In some embodiments described herein is a pharmaceutical composition comprising a fatty acid amide hydrolase (FAAH) cleavable prodrug of Formula (I'), or a pharmaceutically acceptable salt or solvate thereof:

Formula (I')

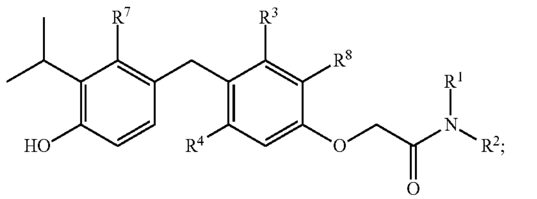

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$;

$R^3$ and $R^4$ are independently selected from —F, —Cl, —Br, and —I;

$R^5$ and $R^6$ are independently selected from hydrogen and $C_1$-$C_6$alkyl; and $R^7$ and $R^8$ are independently selected from hydrogen, —F, —Cl, —Br, and —I;

and a pharmaceutically acceptable excipient; further comprising a peripherally restricted FAAH inhibitor.

In some embodiments, $R^7$ is hydrogen. In some embodiments, $R^7$ is —F. In some embodiments, $R^7$ is —Cl. In some embodiments, $R^7$ is —Br.

In some embodiments, $R^8$ is hydrogen. In some embodiments, $R^8$ is —F. In some embodiments, $R^8$ is —Cl. In some embodiments, $R^8$ is —Br.

In some embodiments, $R^1$ is hydrogen. In some embodiments, $R^1$ is $C_{1-6}$alkyl.

In some embodiments, $R^2$ is $C_1$-$C_6$alkyl optionally substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo. In some embodiments, $R^2$ is $C_1$-$C_6$alkyl substituted with one cyano. In some embodiments, $R^2$ is $C_1$-$C_6$alkyl substituted with one or more —$OR^5$. In some embodiments, $R^2$ is $C_1$-$C_6$alkyl substituted with one or more —OH. In some embodiments, $R^2$ is $C_1$-$C_6$alkyl substituted with one —OH. In some embodiments, $R^2$ is $C_1$-$C_6$alkyl substituted with one or more —$NR^5R^6$. In some embodiments, $R^2$ is $C_1$-$C_6$alkyl substituted with one or more —$NH_2$. In some embodiments, $R^2$ is $C_1$-$C_6$alkyl substituted with one —$NH_2$. In some embodiments, $R^2$ is $C_1$-$C_6$alkyl substituted with one —$S(O)_2R^5$. In some embodiments, $R^2$ is $C_1$-$C_6$alkyl substituted with one —$S(O)_2H$. In some embodiments, $R^2$ is $C_1$-$C_6$alkyl substituted with one —$S(O)_2OR^5$. In some embodiments, $R^2$ is $C_1$-$C_6$alkyl substituted with one —$S(O)_2$ OH. In some embodiments, $R^2$ is unsubstituted $C_1$-$C_6$alkyl. In some embodiments, $R^2$ is —$CH_3$. In some embodiments, $R^2$ is —$CH_2CH_3$. In some embodiments, $R^2$ is —$CH_2CH_2CH_3$.

In some embodiments, $R^2$ is $C_2$-$C_6$alkenyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkenyl.

In some embodiments, $R^2$ is $C_2$-$C_6$alkynyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkynyl.

In some embodiments, $R^2$ is $C_3$-$C_6$cycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$cycloalkyl.

In some embodiments, $R^2$ is $C_3$-$C_6$heterocycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$heterocycloalkyl.

In some embodiments, $R^2$ is phenyl optionally substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo. In some embodiments, $R^2$ is phenyl substituted with one or more —$OR^5$. In some embodiments, $R^2$ is phenyl substituted with one or more —OH. In some embodiments, $R^2$ is unsubstituted phenyl.

In some embodiments, $R^2$ is —$C_1$-$C_6$alkyl-phenyl optionally substituted with one or more of halo, cyano, —$OR^5$, —$NR^5R^6$, —$S(O)_2R^5$, or —$S(O)_2OR^5$. In some embodiments, $R^2$ is unsubstituted —$C_1$-$C_6$alkyl-phenyl.

In some embodiments, $R^2$ is —$OR^5$. In some embodiments, $R^2$ is —OH. In some embodiments, $R^2$ is —$NR^5R^6$. In some embodiments, $R^2$ is —$NH_2$.

In some embodiments, $R^2$ is hydrogen.

In some embodiments, $R^3$ and $R^4$ are independently selected from —F, —Cl, and —Br. In some embodiments, $R^3$ and $R^4$ are both —Br. In some embodiments, $R^3$ and $R^4$ are both —Br. In some embodiments, $R^3$ and $R^4$ are both —Cl. In some embodiments, $R^3$ and $R^4$ are both —F. In some embodiments, $R^3$ is —Cl and $R^4$ is —Br. In some embodiments, $R^3$ is —F and $R^4$ is —Br. In some embodiments, $R^3$ is —F and $R^4$ is —Cl.

In some embodiments of the pharmaceutical compositions described herein, the fatty acid amide hydrolase (FAAH) cleavable prodrug of Formula (I') has a structure selected from:

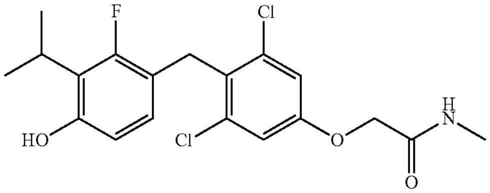
,
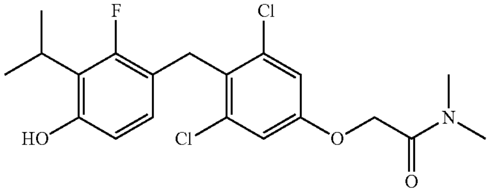
,
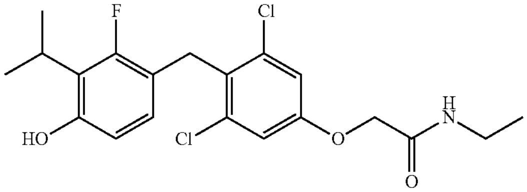
,
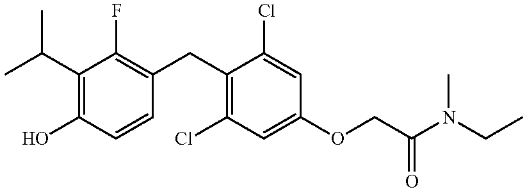
,
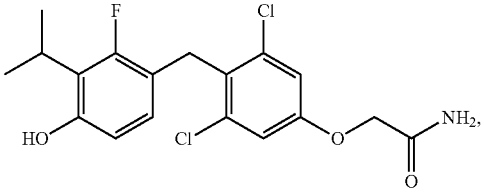
,
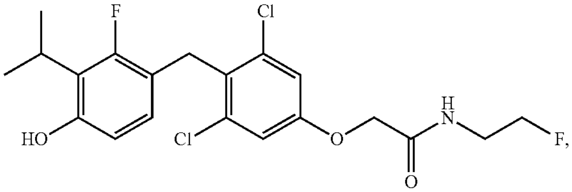
,
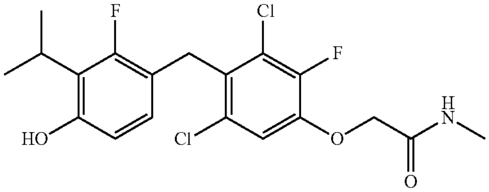
,
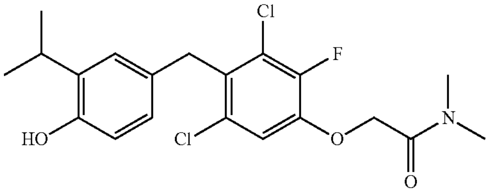
,
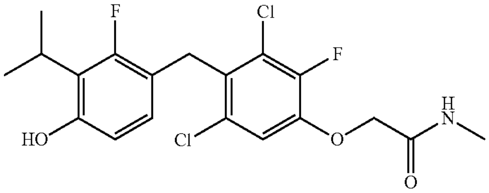
,
-continued
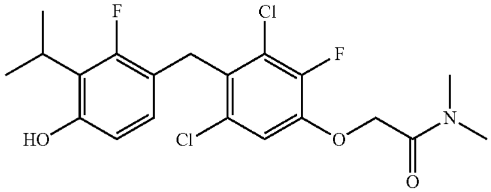
,
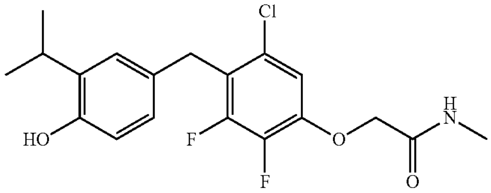
,
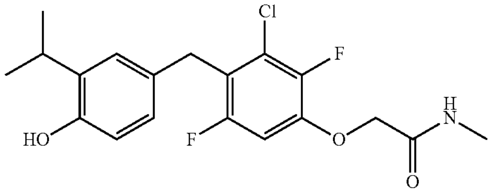
,
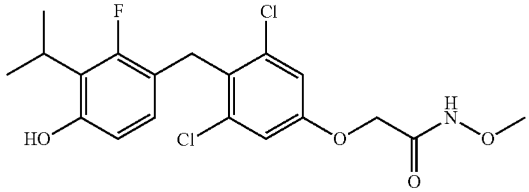
,
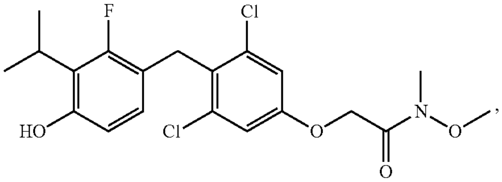
, and
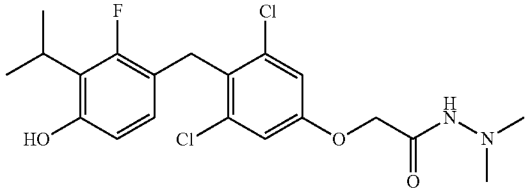
;
or a pharmaceutically acceptable salt or solvate thereof.
In some embodiments described herein is a pharmaceutical composition comprising a fatty acid amide hydrolase (FAAH) cleavable prodrug of Formula (I), or a pharmaceutically acceptable salt or solvate thereof:
Formula (I)
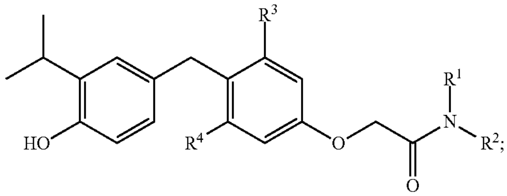
;

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycl- oalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$;

$R^3$ and $R^4$ are independently selected from —F, —Cl, —Br, and —I; and $R^5$ and $R^6$ are independently selected from hydrogen and $C_1$-$C_6$alkyl;

and a pharmaceutically acceptable excipient; further comprising a peripherally restricted FAAH inhibitor.

In some embodiments, $R^1$ is hydrogen. In some embodiments, $R^1$ is $C_{1-6}$alkyl.

In some embodiments, $R^2$ is $C_1$-$C_6$alkyl optionally substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo. In some embodiments, $R^2$ is $C_1$-$C_6$alkyl substituted with one cyano. In some embodiments, $R^2$ is $C_1$-$C_6$alkyl substituted with one or more —$OR^5$. In some embodiments, $R^2$ is $C_1$-$C_6$alkyl substituted with one or more —OH. In some embodiments, $R^2$ is $C_1$-$C_6$alkyl substituted with one —OH. In some embodiments, $R^2$ is $C_1$-$C_6$alkyl substituted with one or more —$NR^5R^6$. In some embodiments, $R^2$ is $C_1$-$C_6$alkyl substituted with one or more —$NH_2$. In some embodiments, $R^2$ is $C_1$-$C_6$alkyl substituted with one —$NH_2$. In some embodiments, $R^2$ is $C_1$-$C_6$alkyl substituted with one —$S(O)_2R^5$. In some embodiments, $R^2$ is $C_1$-$C_6$alkyl substituted with one —$S(O)_2H$. In some embodiments, $R^2$ is $C_1$-$C_6$alkyl substituted with one —$S(O)_2OR^5$. In some embodiments, $R^2$ is $C_1$-$C_6$alkyl substituted with one —$S(O)_2$ OH. In some embodiments, $R^2$ is unsubstituted $C_1$-$C_6$alkyl. In some embodiments, $R^2$ is —$CH_3$. In some embodiments, $R^2$ is —$CH_2CH_3$. In some embodiments, $R^2$ is —$CH_2CH_2CH_3$.

In some embodiments, $R^2$ is $C_2$-$C_6$alkenyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkenyl.

In some embodiments, $R^2$ is $C_2$-$C_6$alkynyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkynyl.

In some embodiments, $R^2$ is $C_3$-$C_6$cycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$cycloalkyl.

In some embodiments, $R^2$ is $C_3$-$C_6$heterocycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$heterocycloalkyl.

In some embodiments, $R^2$ is phenyl optionally substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo. In some embodiments, $R^2$ is phenyl substituted with one or more —$OR^5$. In some embodiments, $R^2$ is phenyl substituted with one or more —OH. In some embodiments, $R^2$ is unsubstituted phenyl.

In some embodiments, $R^2$ is —$C_1$-$C_6$alkyl-phenyl optionally substituted with one or more of halo, cyano, —$OR^5$, —$NR^5R^6$, —$S(O)_2R^5$, or —$S(O)_2OR^5$. In some embodiments, $R^2$ is unsubstituted —$C_1$-$C_6$alkyl-phenyl.

In some embodiments, $R^2$ is —$OR^5$. In some embodiments, $R^2$ is —OH. In some embodiments, $R^2$ is —$NR^5R^6$. In some embodiments, $R^2$ is —$NH_2$.

In some embodiments, $R^2$ is hydrogen.

In some embodiments, $R^3$ and $R^4$ are independently selected from —F, —Cl, and —Br. In some embodiments, $R^3$ and $R^4$ are both —Br. In some embodiments, $R^3$ and $R^4$ are both —Br. In some embodiments, $R^3$ and $R^4$ are both —Cl. In some embodiments, $R^3$ and $R^4$ are both —F. In some embodiments, $R^3$ is —Cl and $R^4$ is —Br. In some embodiments, $R^3$ is —F and $R^4$ is —Br. In some embodiments, $R^3$ is —F and $R^4$ is —Cl.

In some embodiments of the pharmaceutical compositions described herein, the fatty acid amide hydrolase (FAAH) cleavable prodrug of Formula (I') or (I) has a structure selected from:

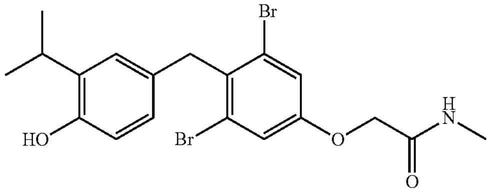 [SMILES: CNC(=O)COc1cc(Cl)c(Cc2ccc(O)c(C(C)C)c2)c(Cl)c1]
,

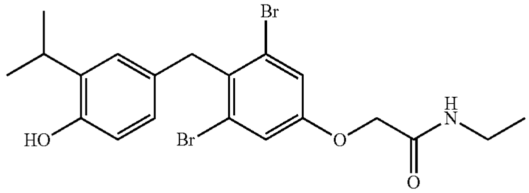 [SMILES: CCNC(=O)COc1cc(Cl)c(Cc2ccc(O)c(C(C)C)c2)c(Cl)c1]
,

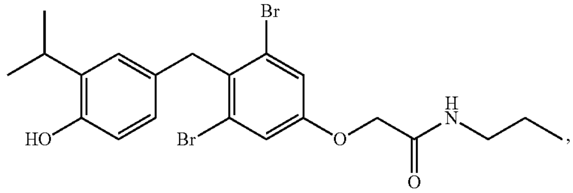
,

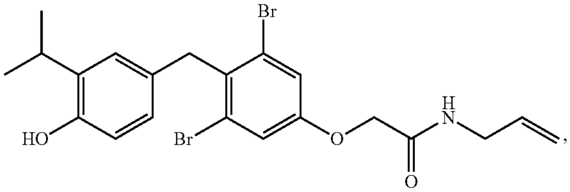
,

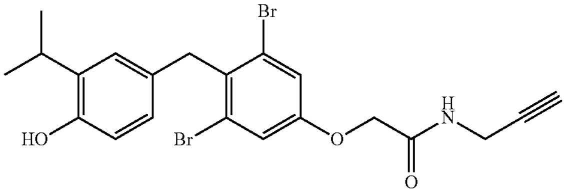
,

-continued
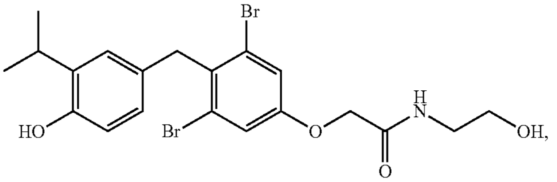
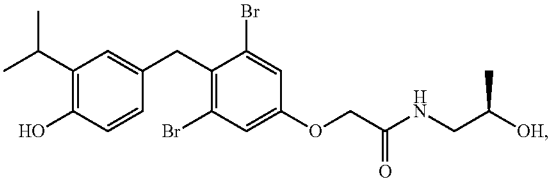
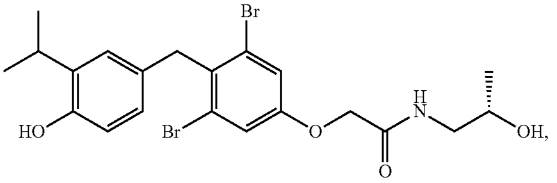
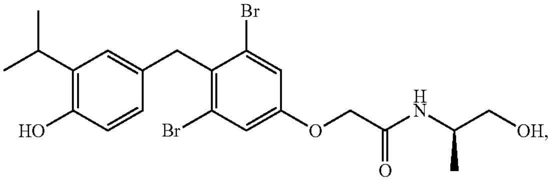
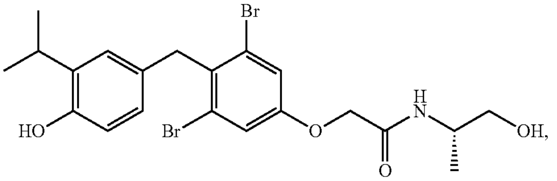
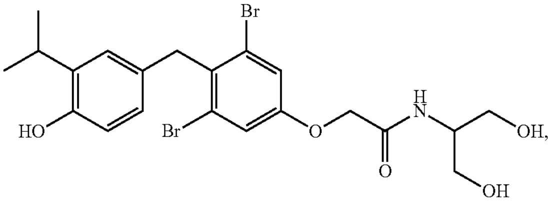
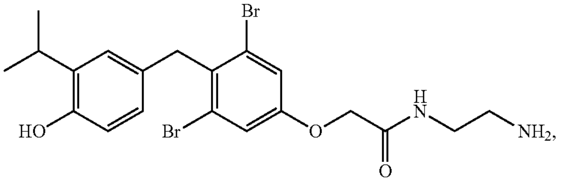
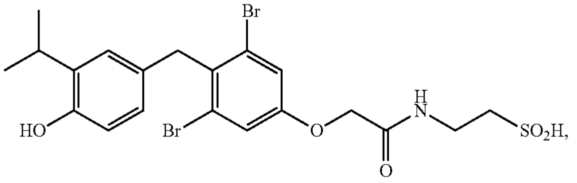
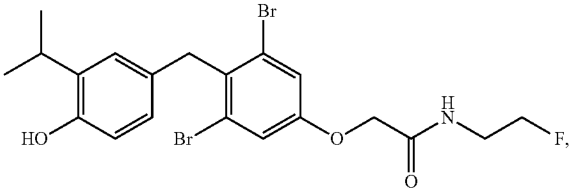
-continued
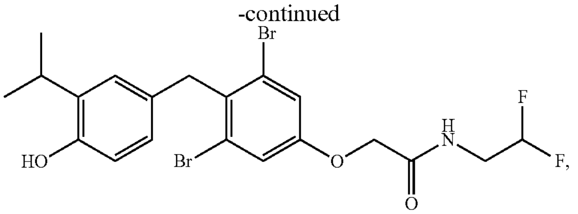
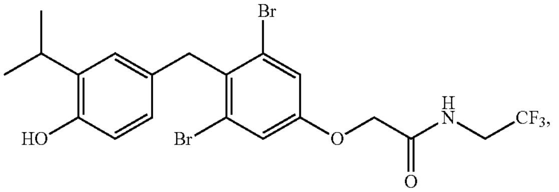
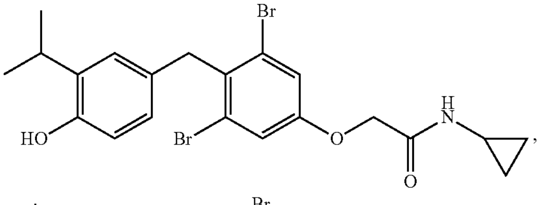
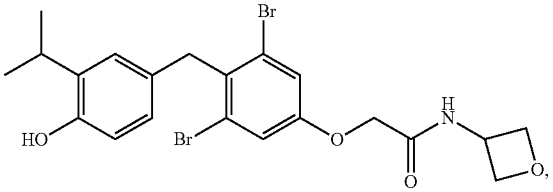
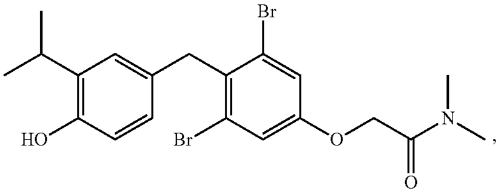
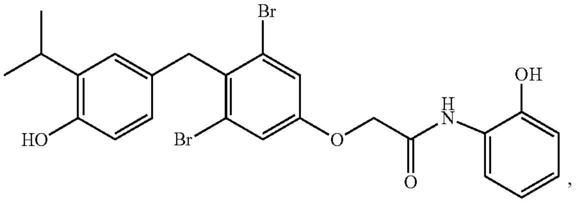
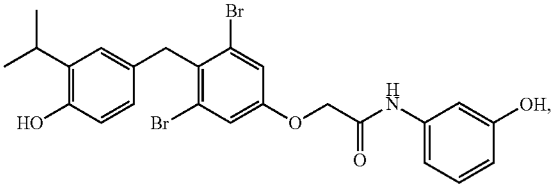
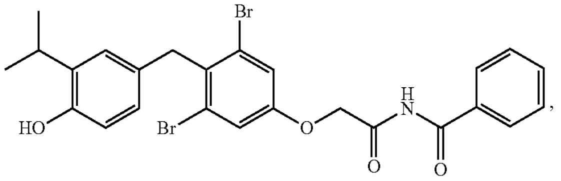
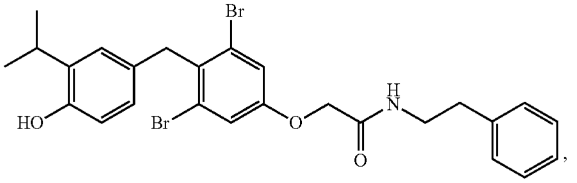

-continued
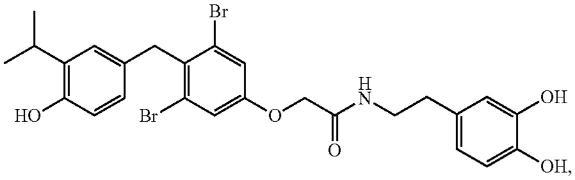
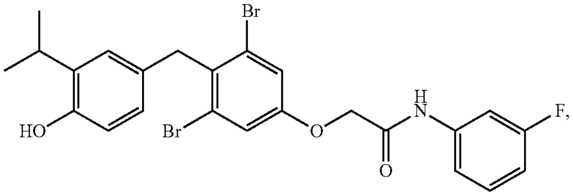
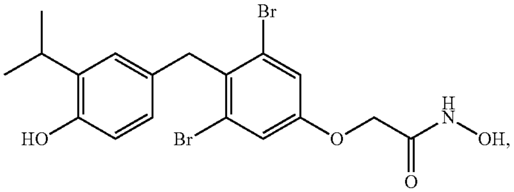
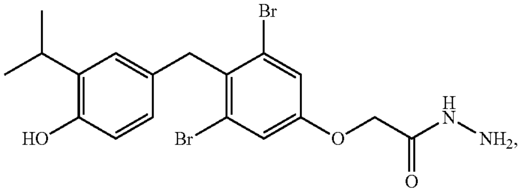
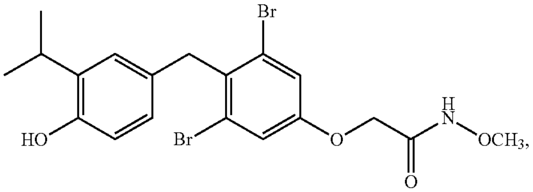
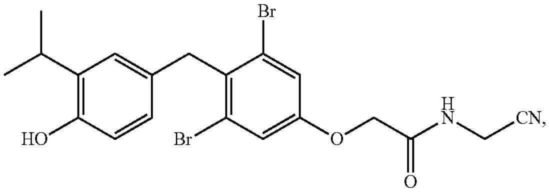
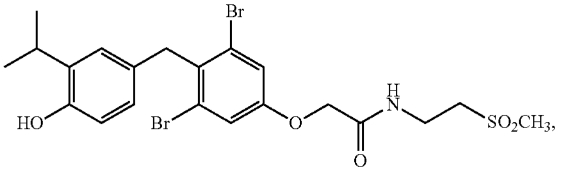
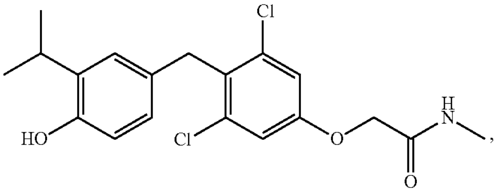
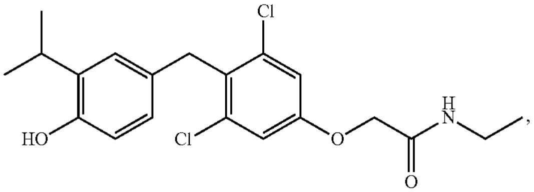
-continued
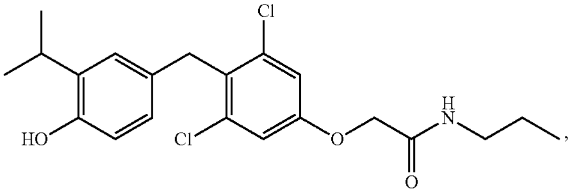
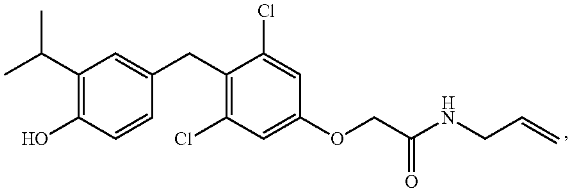
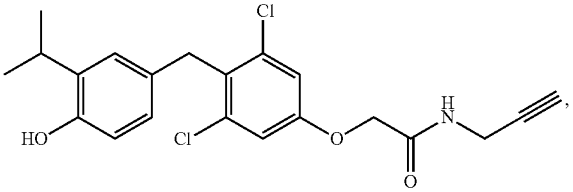
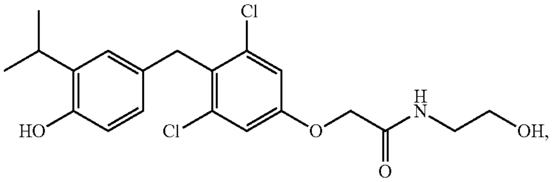
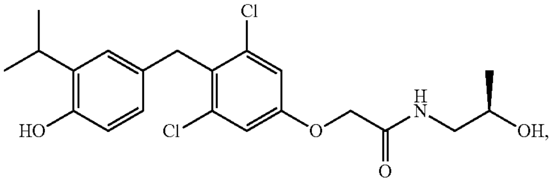
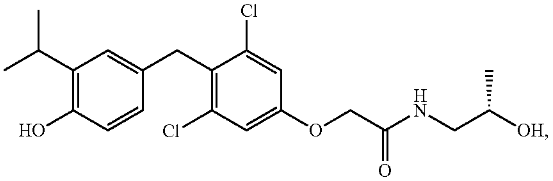
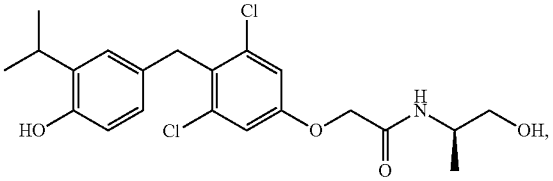
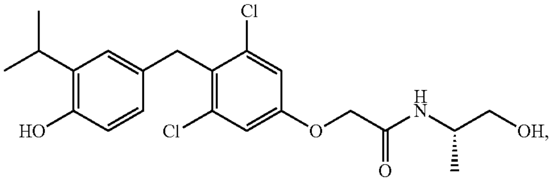
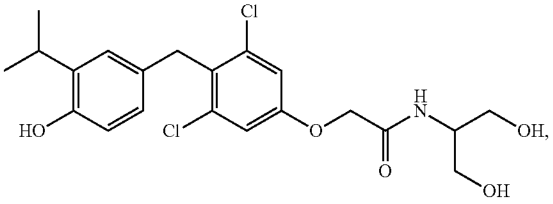

-continued
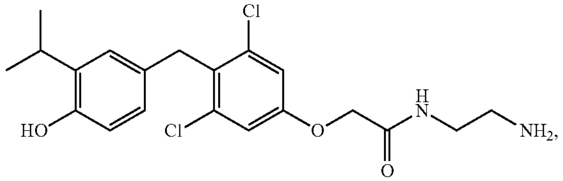
,
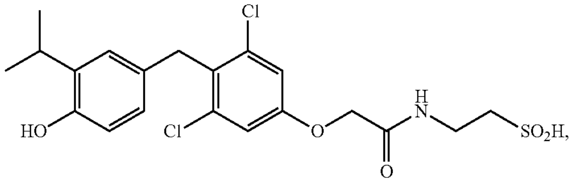
,
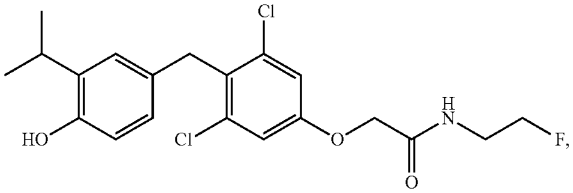
,
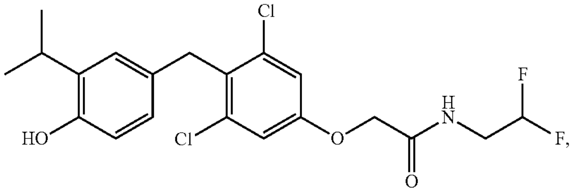
,
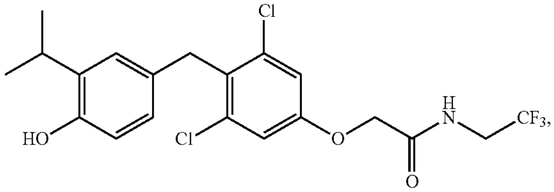
,
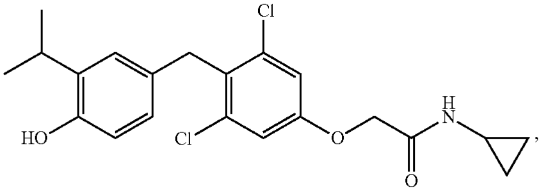
,
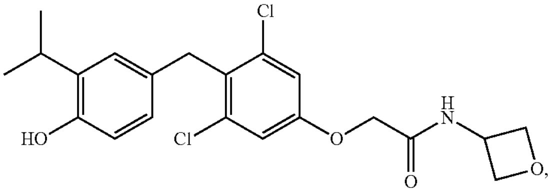
,
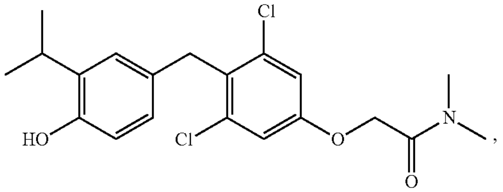
,
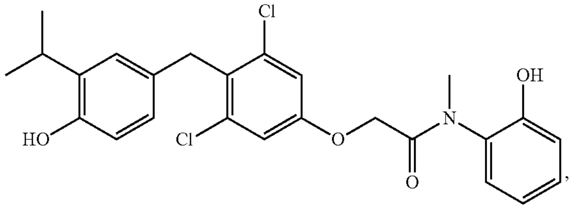
,
-continued
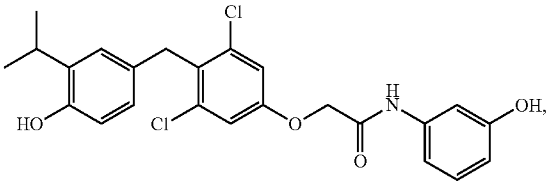
,
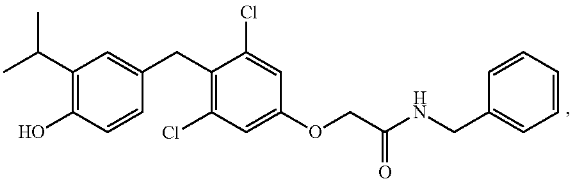
,
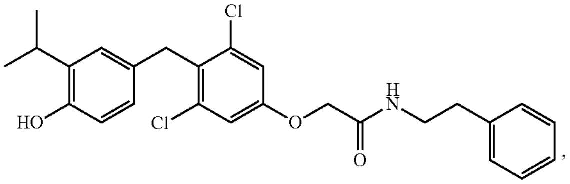
,
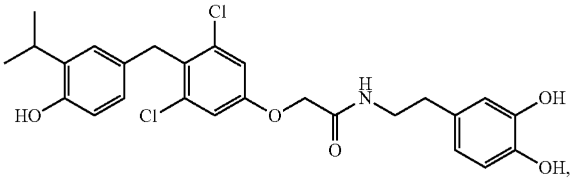
,
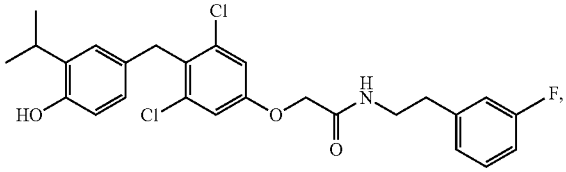
,
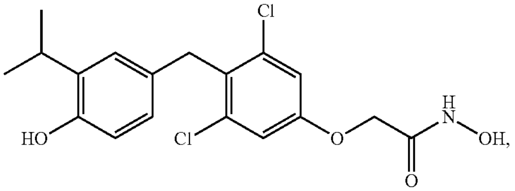
,
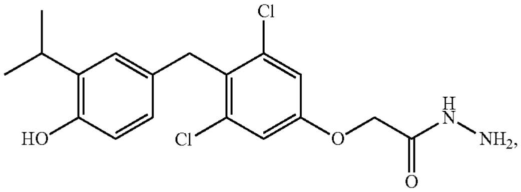
,
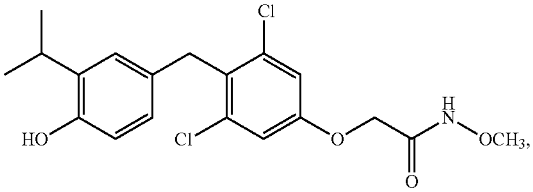
,
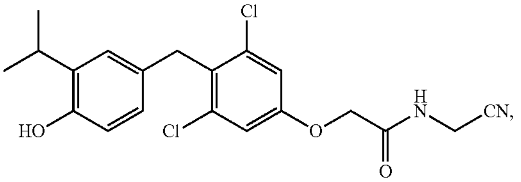
and -continued
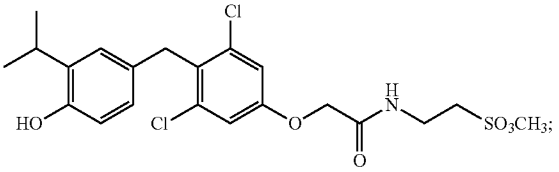
;
or a pharmaceutically acceptable salt or solvate thereof.
In some embodiments of the pharmaceutical compositions described herein, the fatty acid amide hydrolase (FAAH) cleavable prodrug of Formula (I') or (I) has a structure selected from:
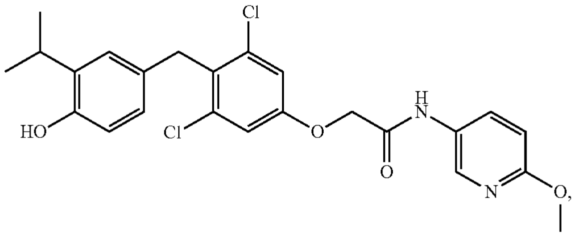
,
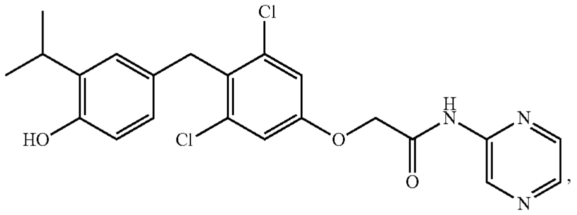
,
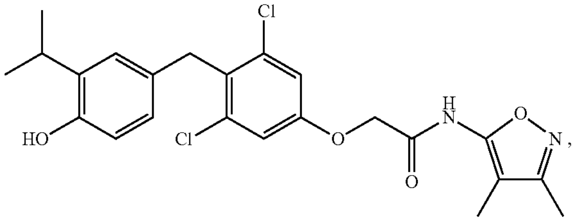
,
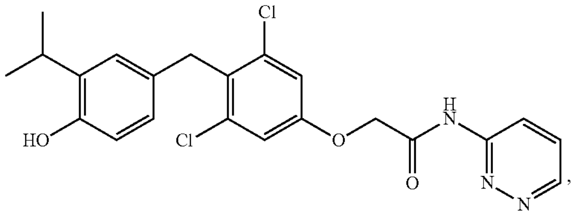
,
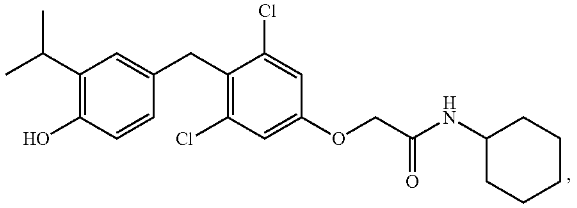
,
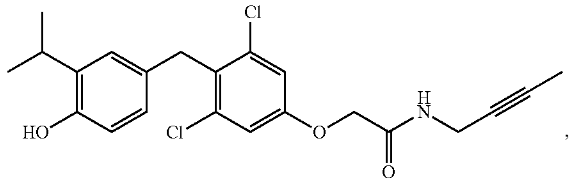
,
-continued
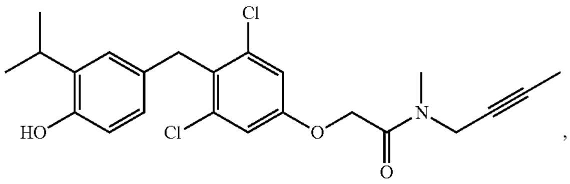
,
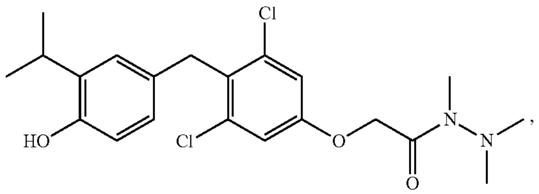
,
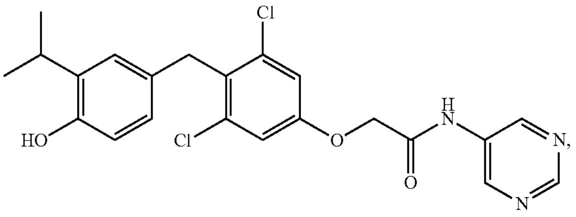
,
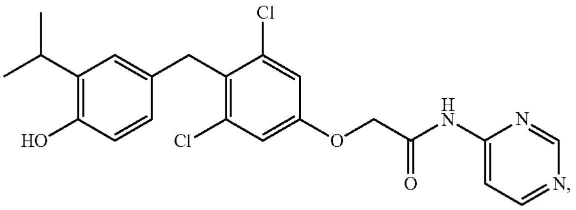
,
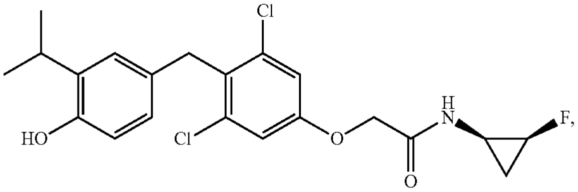
,
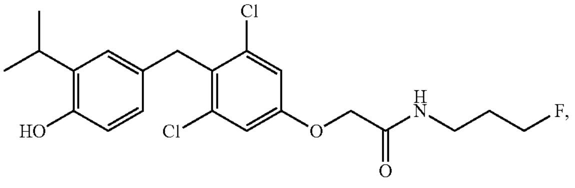
,
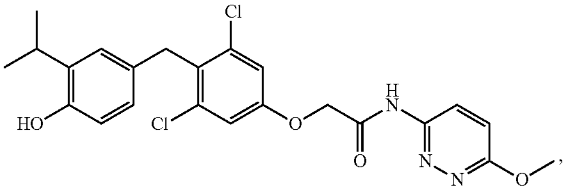
,
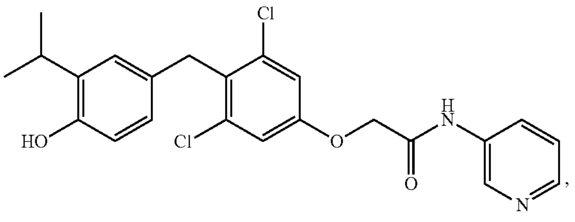
, -continued
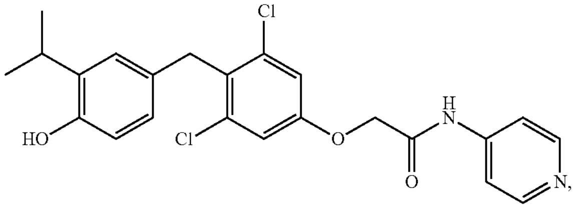
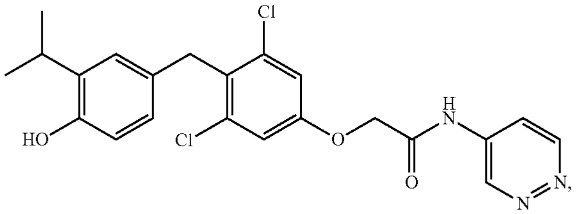
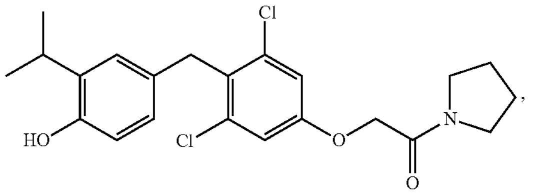
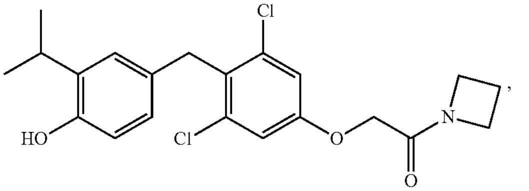
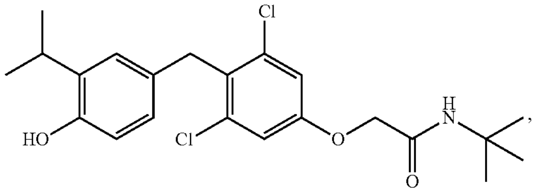
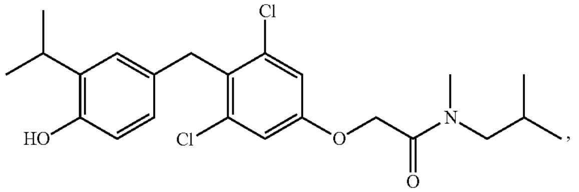
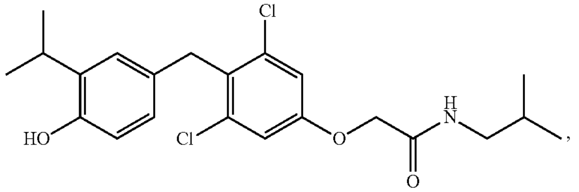
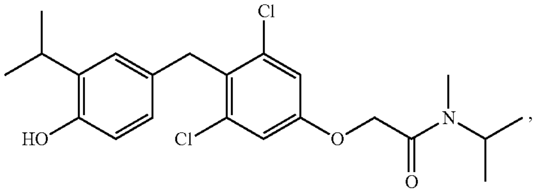
-continued
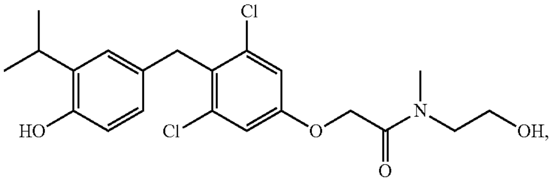
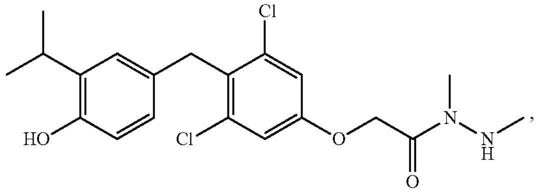
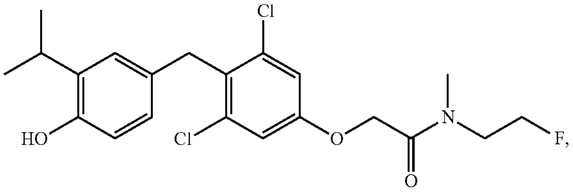
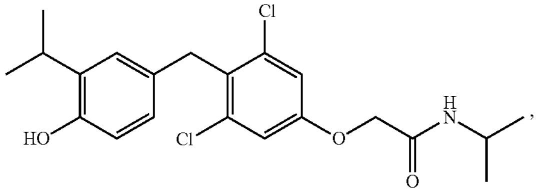
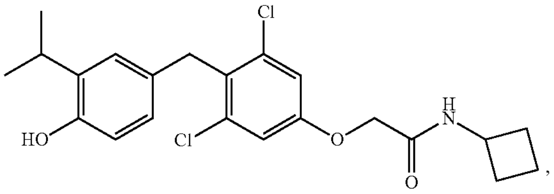
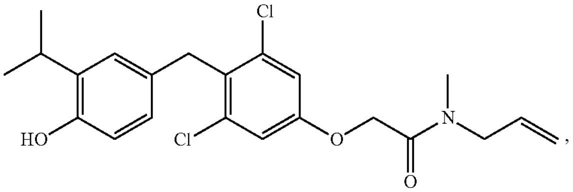
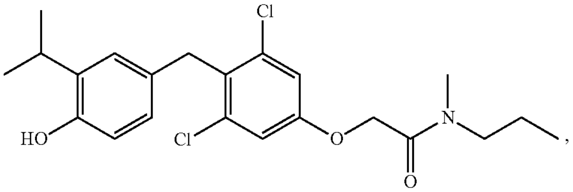
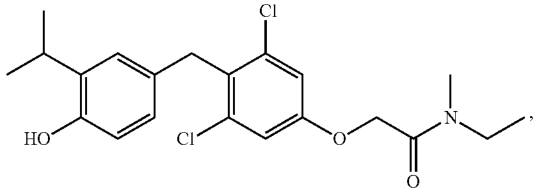
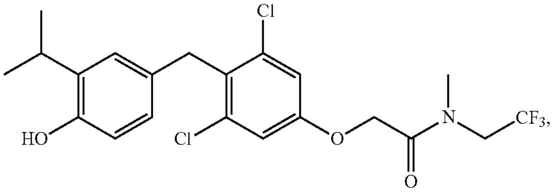

-continued

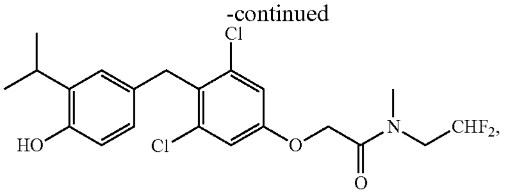

and

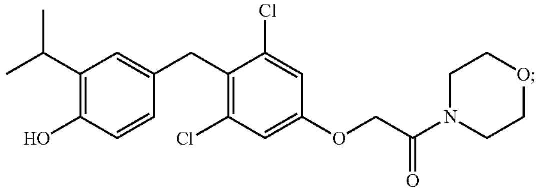

or a pharmaceutically acceptable salt or solvate thereof.

In some embodiments described herein is a pharmaceutical composition comprising a fatty acid amide hydrolase (FAAH) cleavable prodrug of Formula (11), or a pharmaceutically acceptable salt or solvate thereof:

Formula (II)

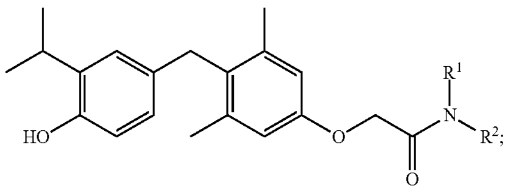

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$; and $R^5$ and $R^6$ are independently selected from hydrogen and $C_1$-$C_6$alkyl;

and a pharmaceutically acceptable excipient; further comprising a peripherally restricted FAAH inhibitor, wherein the peripherally restricted FAAH inhibitor is ASP-3652.

In some embodiments, $R^1$ is hydrogen. In some embodiments, $R^1$ is $C_{1-6}$alkyl.

In some embodiments, $R^2$ is $C_1$-$C_6$alkyl optionally substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo, cyano, —$OR^5$, —$NR^5R^6$, —$S(O)_2R^5$, or —$S(O)_2OR^5$. In some embodiments, $R^2$ is $C_1$-$C_6$alkyl substituted with one or more of halo. In some embodiments, $R^2$ is $C_1$-$C_6$alkyl substituted with one cyano. In some embodiments, $R^2$ is $C_1$-$C_6$alkyl substituted with one or more —$OR^5$. In some embodiments, $R^2$ is $C_1$-$C_6$alkyl substituted with one or more —OH. In some embodiments, $R^2$ is $C_1$-$C_6$alkyl substituted with one —OH. In some embodiments, $R^2$ is $C_1$-$C_6$alkyl substituted with one or more —$NR^5R^6$. In some embodiments, $R^2$ is $C_1$-$C_6$alkyl substituted with one or more —$NH_2$. In some embodiments, $R^2$ is $C_1$-$C_6$alkyl substituted with one —$NH_2$. In some embodiments, $R^2$ is $C_1$-$C_6$alkyl substituted with one —$S(O)_2R^5$. In some embodiments, $R^2$ is $C_1$-$C_6$alkyl substituted with one —$S(O)_2H$. In some embodiments, $R^2$ is $C_1$-$C_6$alkyl substituted with one —$S(O)_2OR^5$. In some embodiments, $R^2$ is $C_1$-$C_6$alkyl substituted with one —$S(O)_2$ OH. In some embodiments, $R^2$ is unsubstituted $C_1$-$C_6$alkyl. In some embodiments, $R^2$ is —$CH_3$. In some embodiments, $R^2$ is —$CH_2CH_3$. In some embodiments, $R^2$ is —$CH_2CH_2CH_3$.

In some embodiments, $R^2$ is $C_2$-$C_6$alkenyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkenyl.

In some embodiments, $R^2$ is $C_2$-$C_6$alkynyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_2$-$C_6$alkynyl.

In some embodiments, $R^2$ is $C_3$-$C_6$cycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$cycloalkyl.

In some embodiments, $R^2$ is $C_3$-$C_6$heterocycloalkyl optionally substituted with one or more of halo, cyano, —$OR^5$, —$NR^5R^6$, —$S(O)_2R^5$, or —$S(O)_2OR^5$. In some embodiments, $R^2$ is unsubstituted $C_3$-$C_6$heterocycloalkyl.

In some embodiments, $R^2$ is phenyl optionally substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo, cyano, —$OR^5$, —$NR^5R^6$, —$S(O)_2R^5$, or —$S(O)_2OR^5$. In some embodiments, $R^2$ is phenyl substituted with one or more of halo. In some embodiments, $R^2$ is phenyl substituted with one or more —$OR^5$. In some embodiments, $R^2$ is phenyl substituted with one or more —OH. In some embodiments, $R^2$ is unsubstituted phenyl.

In some embodiments, $R^2$ is —$C_1$-$C_6$alkyl-phenyl optionally substituted with one or more of halo, cyano, —$OR^5$, —$NR^5R^6$, —$S(O)_2R^5$, or —$S(O)_2OR^5$. In some embodiments, $R^2$ is unsubstituted —$C_1$-$C_6$alkyl-phenyl.

In some embodiments, $R^2$ is —$OR^5$. In some embodiments, $R^2$ is —OH. In some embodiments, $R^2$ is —$NR^5R^6$. In some embodiments, $R^2$ is —$NH_2$.

In some embodiments, $R^2$ is hydrogen.

In some embodiments of the pharmaceutical compositions described herein, the fatty acid amide hydrolase (FAAH) cleavable prodrug of Formula (II) has a structure selected from:

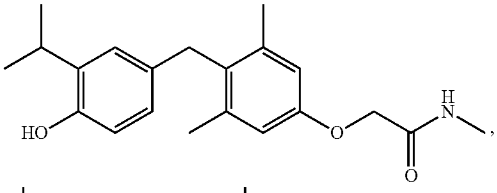

,

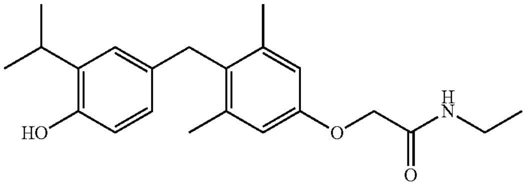

,

-continued
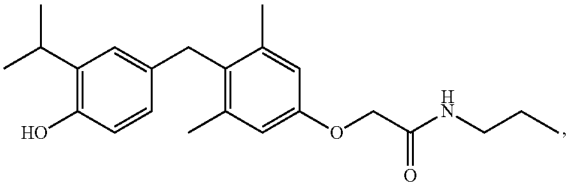
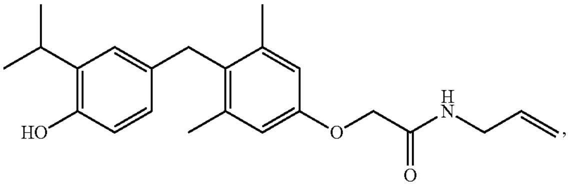
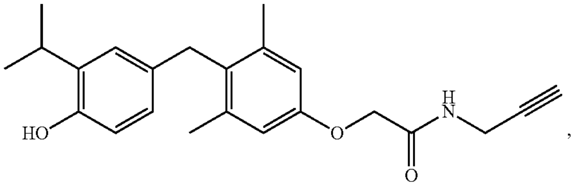
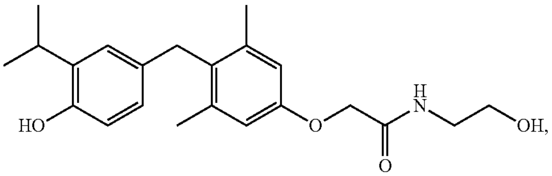
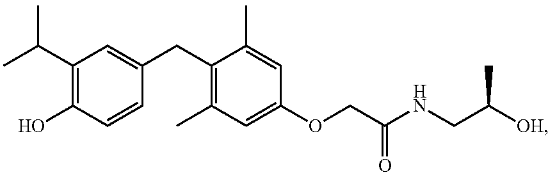
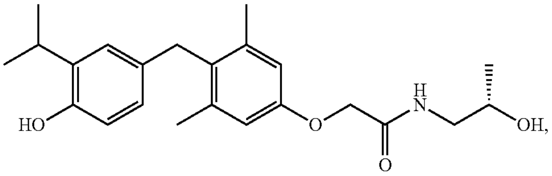
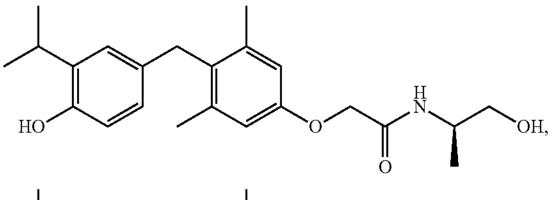
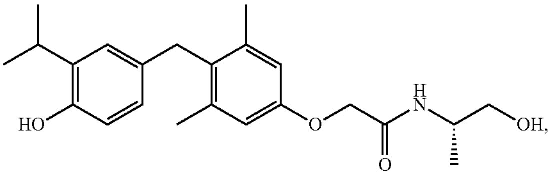
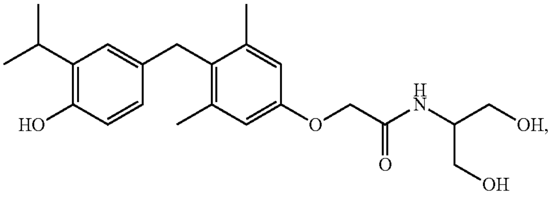
-continued
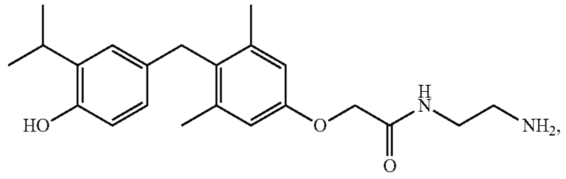
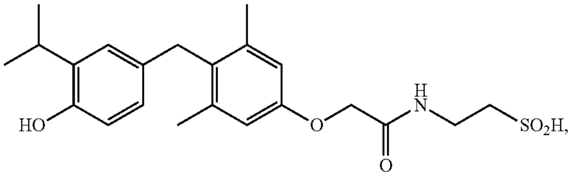
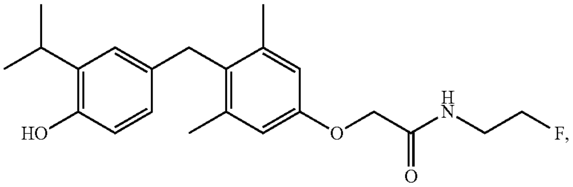
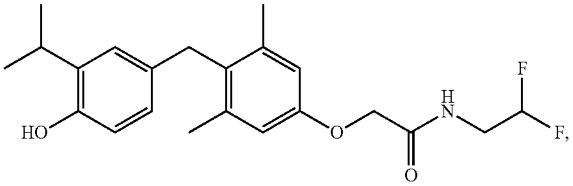
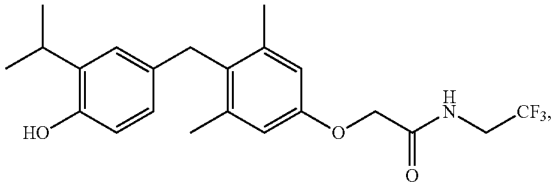
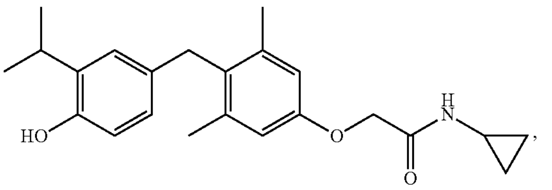
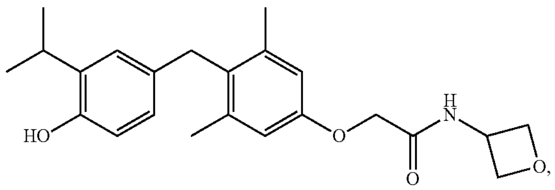
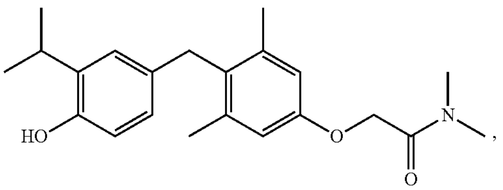
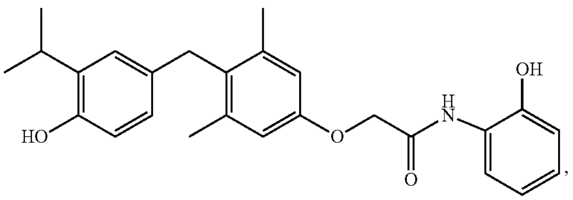

-continued

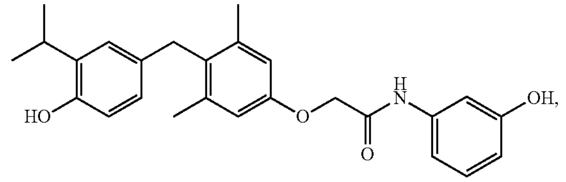

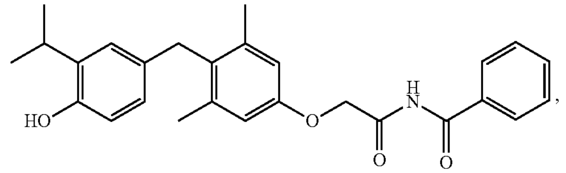

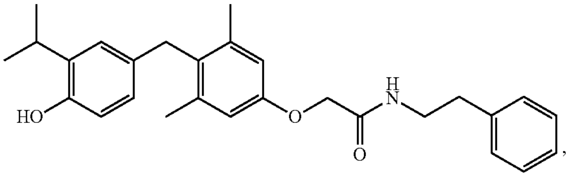

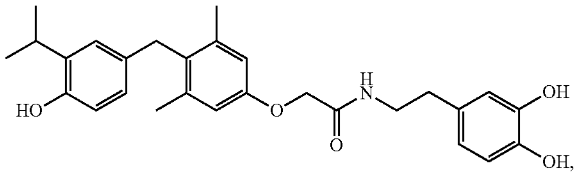

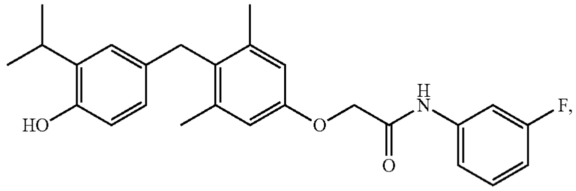

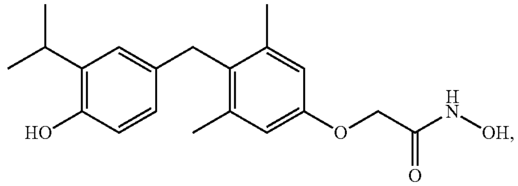

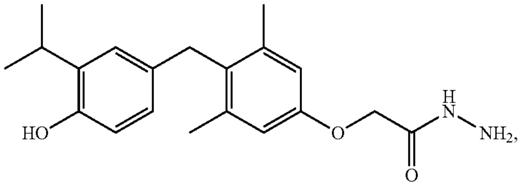

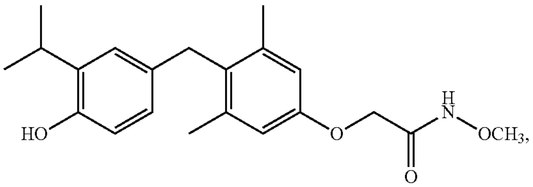

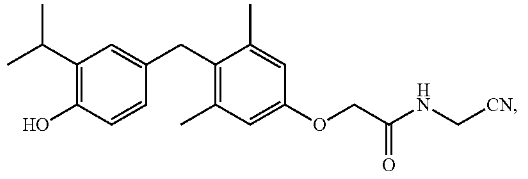

and

-continued

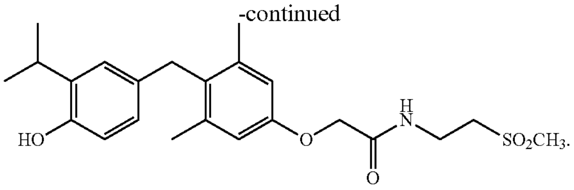

Peripherally Restricted FAAH Inhibitors

The pharmaceutical compositions described herein comprise a peripherally restricted FAAH inhibitor. In some embodiments, the peripherally restricted FAAH inhibitor is disclosed in US 2008/0306046, which is herein incorporated by reference in its entirety.

In some embodiments, the peripherally restricted FAAH inhibitor is a compound of Formula (X), or a pharmaceutically acceptable salt thereof:

Formula (X)

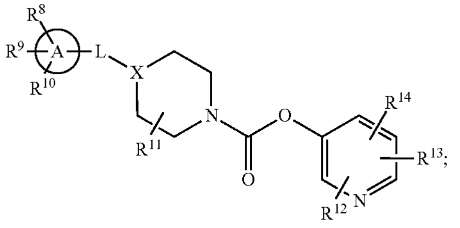

wherein:

ring A is a benzene ring, cyclopentane ring, cyclohexane ring, cycloheptane ring, or a 5- to 7 membered nitrogen-containing hetero ring;

L is a single bond, lower alkylene, lower alkenylene, —N($R^{15}$)—C(═O)—, —C(═O)—N($R^{15}$)—, -(lower alkenylene)-C(═O), —O—, or C(═O);

$R^{15}$ is H or lower alkyl;

X is CH or N;

$R^8$, $R^9$, and $R^{10}$ are each independently selected from:

(i) a group selected from the group consisting of H, halo, —CN, $CF_3$, lower alkyl, and —O-lower alkyl;

(ii) aryl optionally substituted with 1 to 5 groups independently selected from the group consisting of H, halo, —CN, $CF_3$, lower alkyl, and —O-lower alkyl;

(iii) nitrogen-containing heteroaryl optionally substituted with 1 to 5 groups independently selected from the group consisting of H, halo, —CN, —$CF_3$, lower alkyl, and —O-lower alkyl;

(iv) $R^{16}$-(lower alkenylene)-O—;

(v) $R^{16}$-(lower alkenylene)-N($R^{15}$)—; or (vi) $R^{17}R^{18}$N—C(═O)—;

$R^{16}$ is (i) aryl optionally substituted with 1 to 5 groups independently selected from the group consisting of H, halo, —CN, —$CF_3$, lower alkyl, and —O-lower alkyl;

(ii) nitrogen-containing heteroaryl optionally substituted with 1 to 5 groups independently selected from the group consisting of H, halo, —CN, —$CF_3$, lower alkyl, and —O-lower alkyl; or (iii) 3- to 8-membered cycloalkyl;

$R^{17}$ and $R^{18}$ are each independently selected from H, lower alkyl, and 3- to 8-membered cycloalkyl; or $R^{17}$ and $R^{18}$ may form, together with the nitrogen atom bonded thereto, a 3- to 8-membered nitrogen-containing hetero ring;

$R^{11}$ is selected from H, lower alkyl, and oxo (═O); and one of $R^{12}$, $R^{13}$, and $R^{14}$ is —C(═O)—O-(lower alkyl) or —$CO_2H$, and the others are H.

In some embodiments, the peripherally restricted FAAH inhibitor is 5-(((4-(4-((3-fluorobenzyl)oxy)phenoxy)piperidin-1-yl)carbonyl)oxy)nicotinic acid. In some embodiments, the peripherally restricted FAAH inhibitor is 5-(((4-(2-phenylethyl)piperidin-1-yl)carbonyl)oxy)nicotinic acid. In some embodiments, the peripherally restricted FAAH inhibitor is 5-(((4-(4-(2-cyclohexylethoxy)phenoxy)piperidin-1-yl)carbonyl)oxy)nicotinic acid. In some embodiments, the peripherally restricted FAAH inhibitor is 5-(((4-((E)-2-phenylvinyl)piperidin-1-yl)carbonyl)oxy)nicotinic acid. In some embodiments, the peripherally restricted FAAH inhibitor is 5-(((4-(3-(1-(6-methylpyridin-2-yl)piperidin-4-yl)propyl)piperidin-1-yl)carbonyl)oxy)nicotinic acid. In some embodiments, the peripherally restricted FAAH inhibitor is 5-(methoxycarbonyl)pyridin-3-yl 4-(2-phenylethyl)piperazine-1-carboxylate. In some embodiments, the peripherally restricted FAAH inhibitor is ASP-3652. In some embodiments, the peripherally restricted FAAH inhibitor is ASP-3652 which is 5-(((4-(2-phenylethyl)piperidin-1-yl)carbonyl)oxy)nicotinic acid.

Compounds

The compounds of Formula (I'), (I), and (II) described herein are amide prodrugs of TRO agonists. The amide prodrugs described herein are cleaved by fatty acid amide hydrolase (FAAH) to give the active TRO agonist. In some embodiments is a compound selected from:

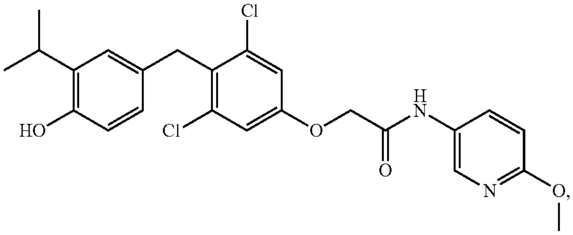

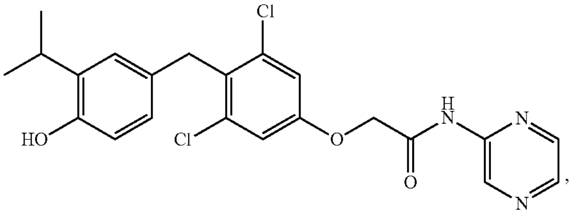
,

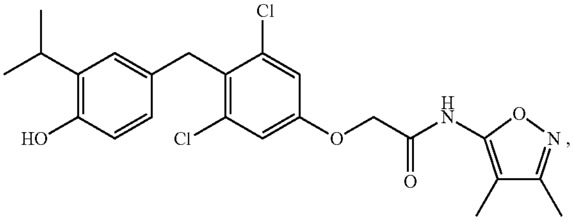
,

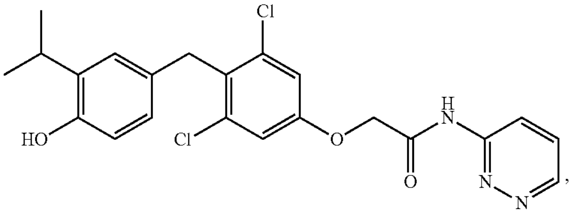
,

-continued

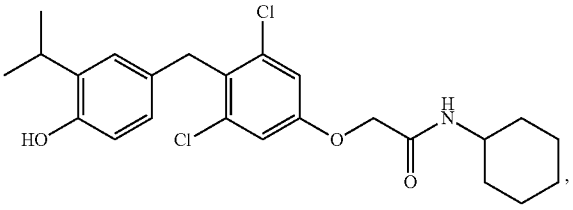
,

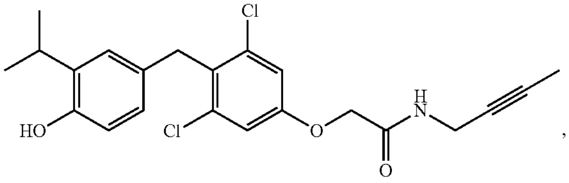
,

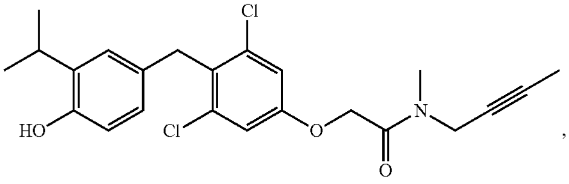
,

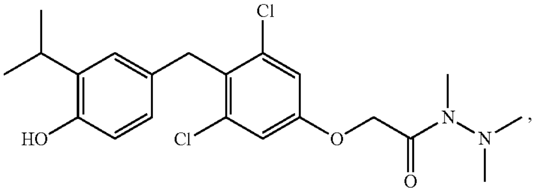

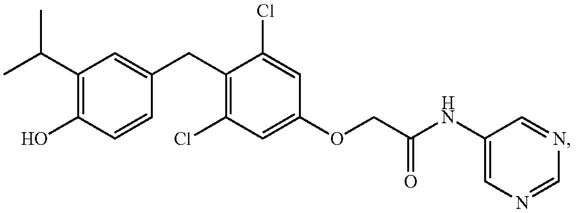

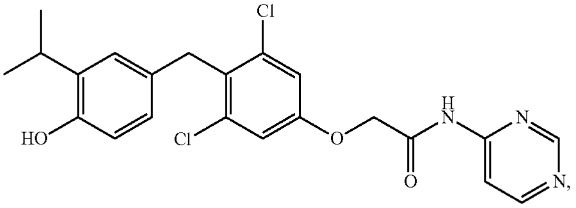

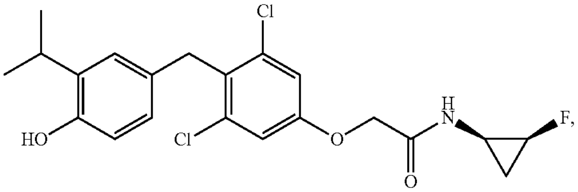

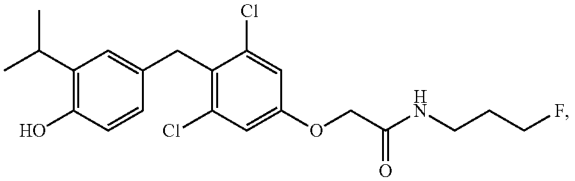

-continued
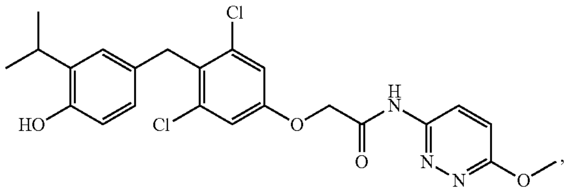
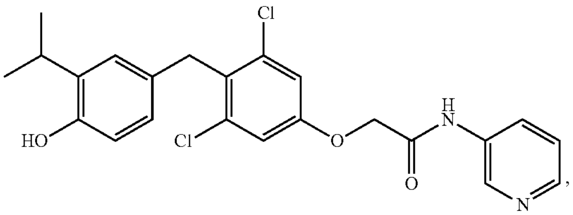
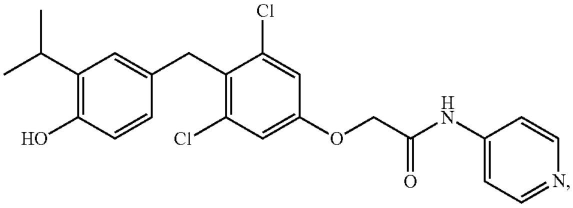
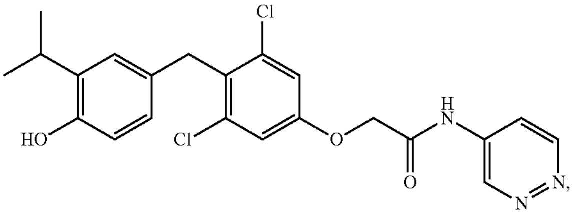
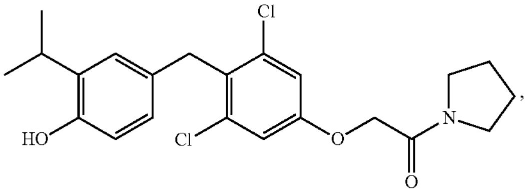
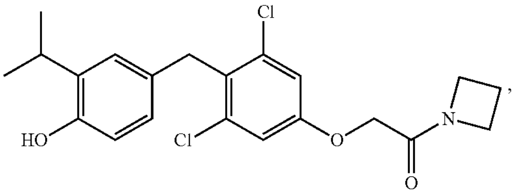
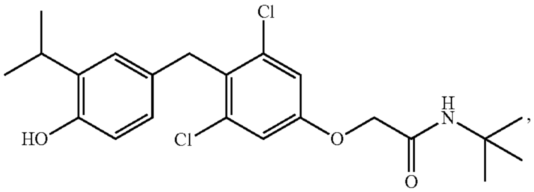
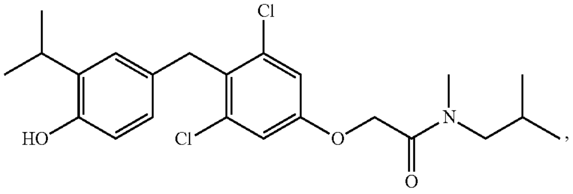
-continued
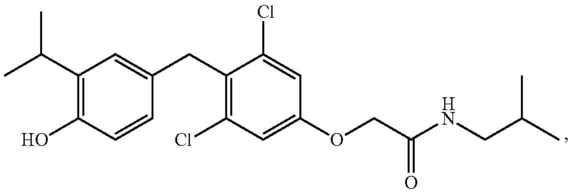
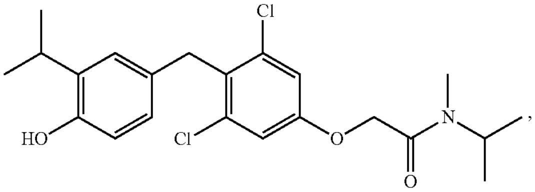
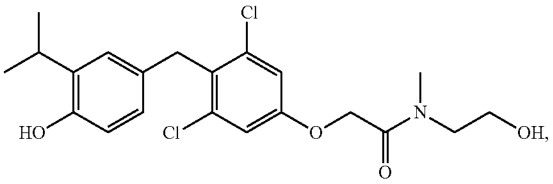
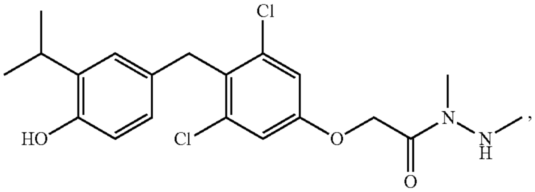
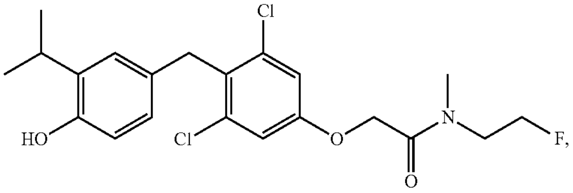
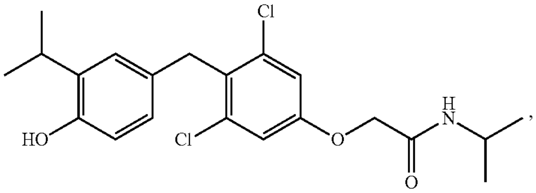
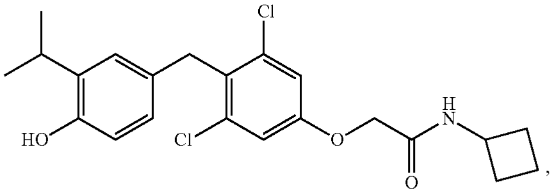
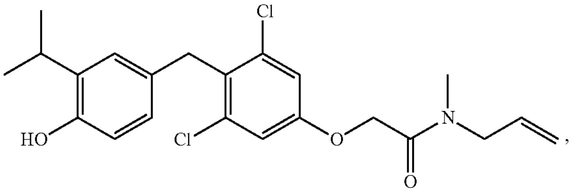
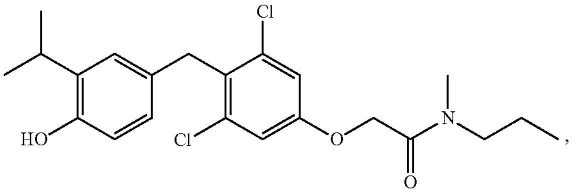

-continued
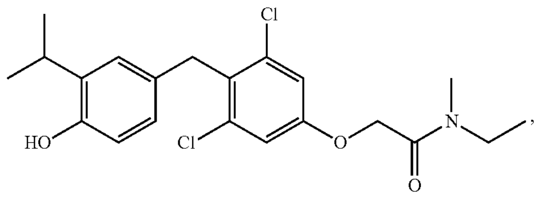
,
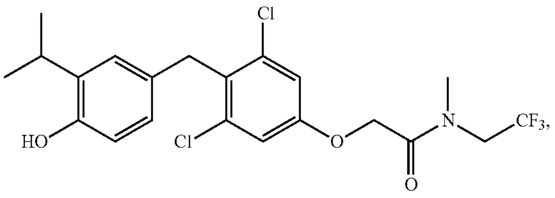
,
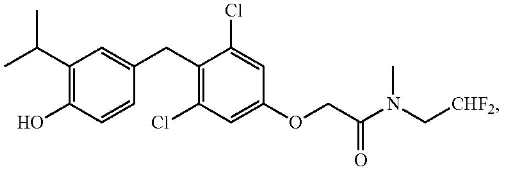
, and
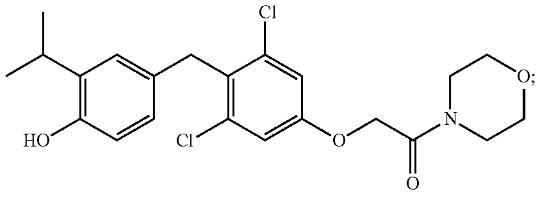
;
or a pharmaceutically acceptable salt or solvate thereof.
In some embodiments is a pharmaceutical composition comprising a pharmaceutically acceptable excipient and a compound selected from
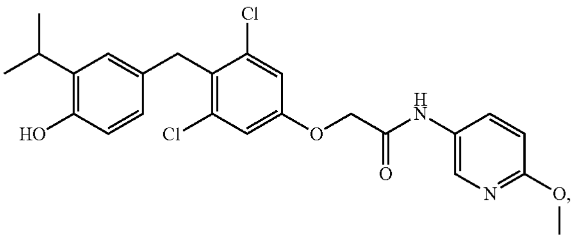
,
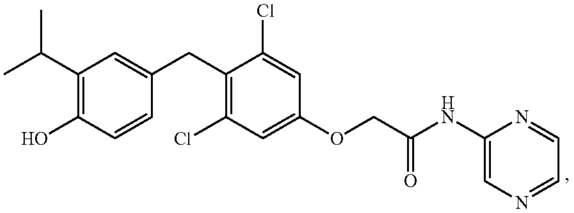
,
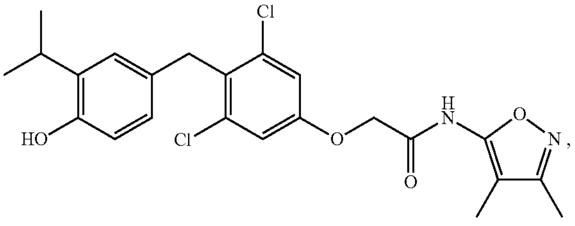
,
-continued
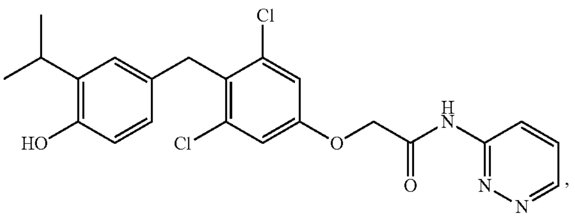
,
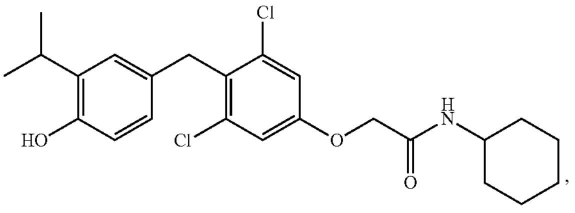
,
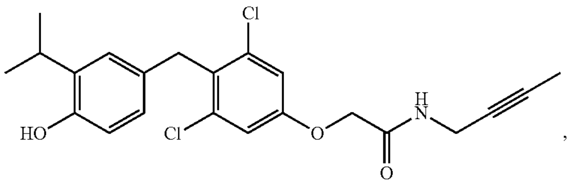
,
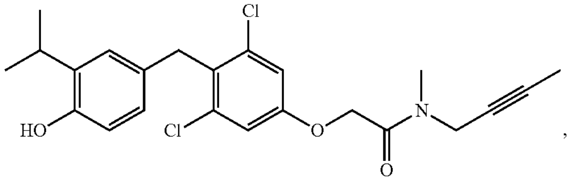
,
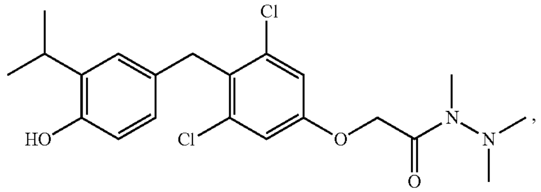
,
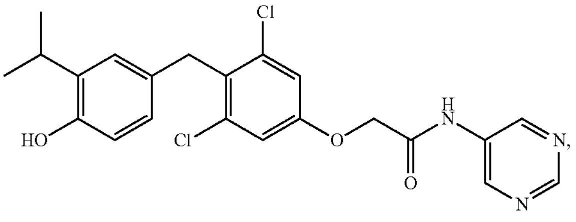
,
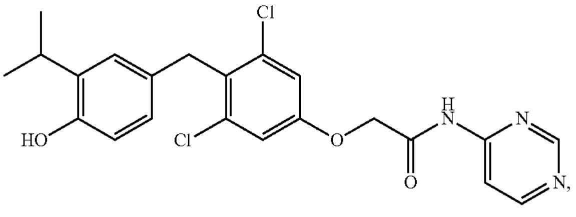
,
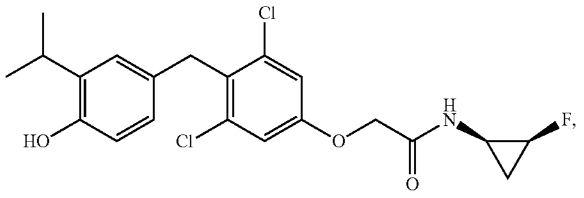
, -continued
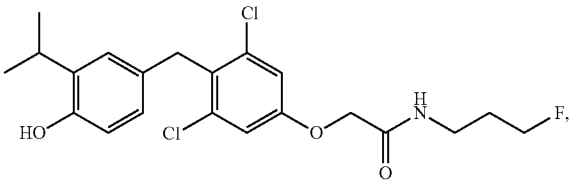
,
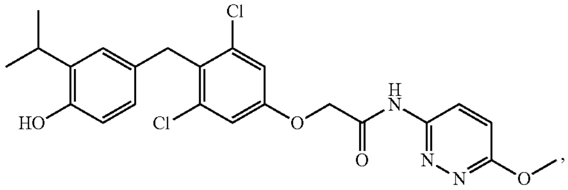
,
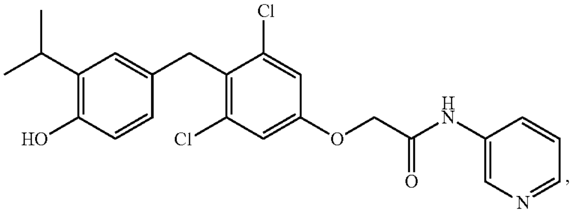
,
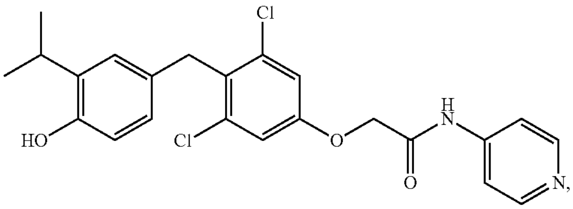
,
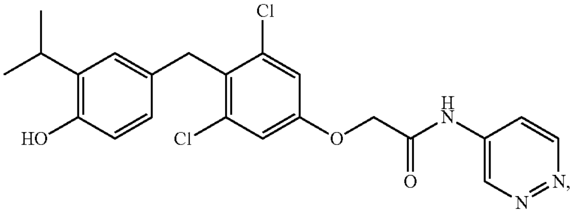
,
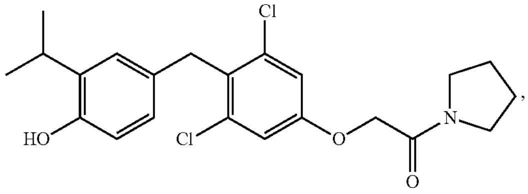
,
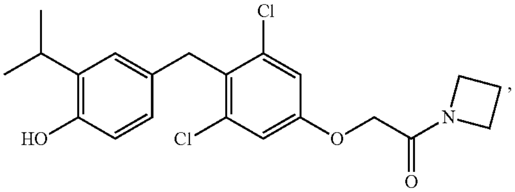
,
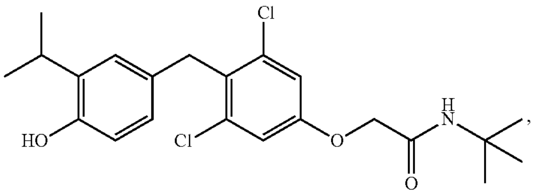
,
-continued
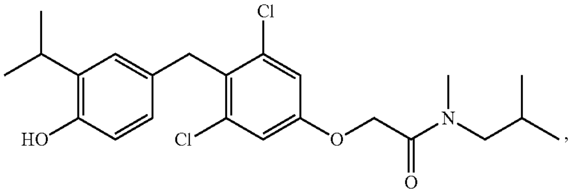
,
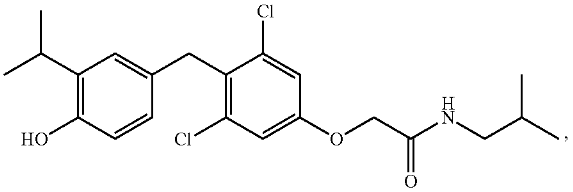
,
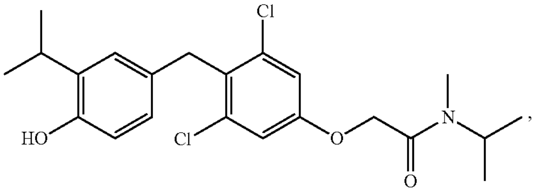
,
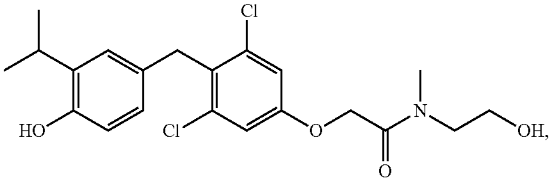
,
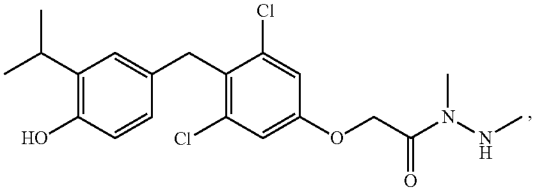
,
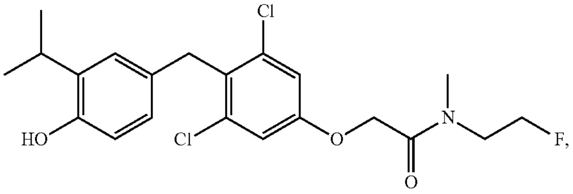
,
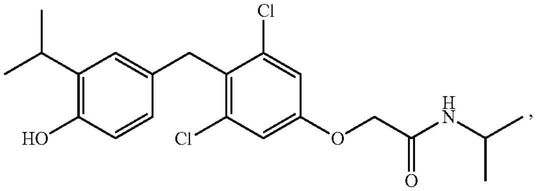
,
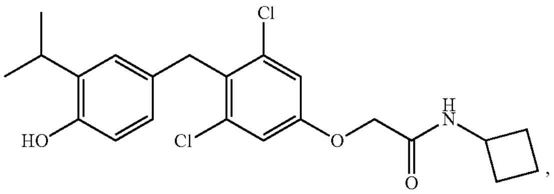
,
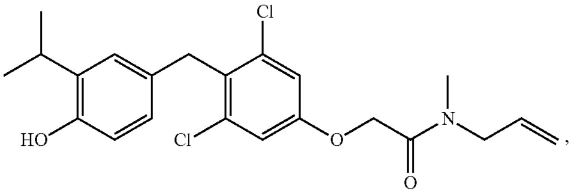
, -continued

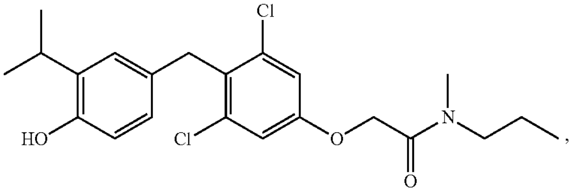

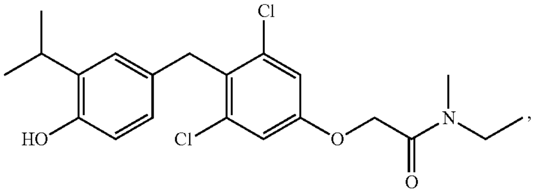

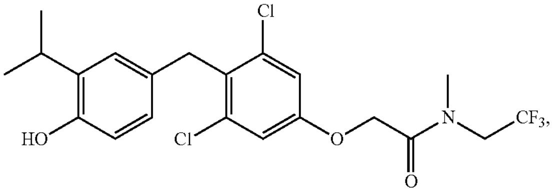

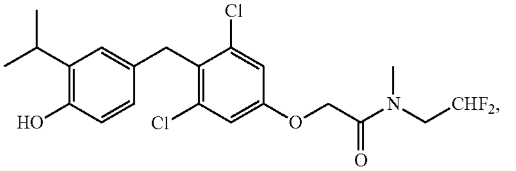

and

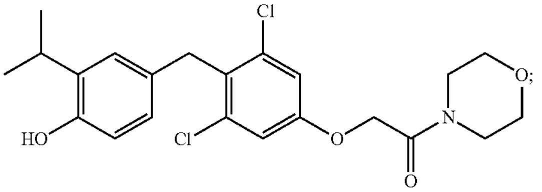

or a pharmaceutically acceptable salt or solvate thereof.

Methods

In some embodiments is a method of treating a CNS disease or disorder in a patient in need thereof comprising administering to the patient a pharmaceutical composition described herein comprising a fatty acid amide hydrolase (FAAH) cleavable prodrug of Formula (I') or (I), or a pharmaceutically acceptable salt or solvate thereof, and a pharmaceutically acceptable excipient; further comprising a peripherally restricted FAAH inhibitor. In some embodiments is a method of treating a CNS disease or disorder in a patient in need thereof comprising administering to the patient a pharmaceutical composition described herein comprising a fatty acid amide hydrolase (FAAH) cleavable prodrug of Formula (I') or (I), or a pharmaceutically acceptable salt or solvate thereof, and a pharmaceutically acceptable excipient; further comprising the peripherally restricted FAAH inhibitor ASP-3652. In some embodiments is a method of treating a CNS disease or disorder in a patient in need thereof comprising administering to the patient a pharmaceutical composition described herein comprising a fatty acid amide hydrolase (FAAH) cleavable prodrug of Formula (I') or (I), or a pharmaceutically acceptable salt or solvate thereof, and a pharmaceutically acceptable excipient; further comprising a peripherally restricted FAAH inhibitor, wherein the CNS disease or disorder is selected from acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (HDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), and Zellweger syndrome. In some embodiments is a method of treating a CNS disease or disorder in a patient in need thereof comprising administering to the patient a pharmaceutical composition described herein comprising a fatty acid amide hydrolase (FAAH) cleavable prodrug of Formula (I') or (I), or a pharmaceutically acceptable salt or solvate thereof, and a pharmaceutically acceptable excipient; further comprising a peripherally restricted FAAH inhibitor, wherein the CNS disease or disorder is multiple sclerosis. In some embodiments is a method of treating a CNS disease or disorder in a patient in need thereof comprising administering to the patient a pharmaceutical composition described herein comprising a fatty acid amide hydrolase (FAAH) cleavable prodrug of Formula (I') or (I), or a pharmaceutically acceptable salt or solvate thereof, and a pharmaceutically acceptable excipient; further comprising a peripherally restricted FAAH inhibitor, wherein the CNS disease or disorder is X-linked adrenoleukodystrophy.

In some embodiments is a method of treating a CNS disease or disorder in a patient in need thereof comprising administering to the patient a pharmaceutical composition described herein comprising a fatty acid amide hydrolase (FAAH) cleavable prodrug of Formula (II), or a pharmaceutically acceptable salt or solvate thereof, and a pharmaceutically acceptable excipient; further comprising a peripherally restricted FAAH inhibitor. In some embodiments is a method of treating a CNS disease or disorder in a patient in need thereof comprising administering to the patient a pharmaceutical composition described herein comprising a fatty acid amide hydrolase (FAAH) cleavable prodrug of Formula (II), or a pharmaceutically acceptable salt or solvate thereof, and a pharmaceutically acceptable excipient; further comprising the peripherally restricted FAAH inhibitor ASP-3652. In some embodiments is a method of treating a CNS disease or disorder in a patient in need thereof comprising administering to the patient a pharmaceutical composition described herein comprising a fatty acid amide hydrolase (FAAH) cleavable prodrug of Formula (II), or a pharmaceutically acceptable salt or solvate thereof, and a pharmaceutically acceptable excipient; further comprising a peripherally restricted FAAH inhibitor, wherein the CNS disease or disorder is selected from acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (HDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), and Zellweger syndrome. In some embodiments is a method of treating a CNS disease or disorder in a patient in need thereof comprising administering to the patient a pharmaceutical composition described herein comprising a fatty acid amide hydrolase (FAAH) cleavable prodrug of Formula (II), or a pharmaceutically acceptable salt or solvate thereof, and a pharmaceutically acceptable excipient; further comprising a peripherally restricted FAAH inhibitor, wherein the CNS disease or disorder is multiple sclerosis. In some embodiments is a method of treating a CNS disease or disorder in a patient in need thereof comprising administering to the patient a pharmaceutical composition described herein comprising a fatty acid amide hydrolase (FAAH) cleavable prodrug of Formula (II), or a pharmaceutically acceptable salt or solvate thereof, and a pharmaceutically acceptable excipient; further comprising a peripherally restricted FAAH inhibitor, wherein the CNS disease or disorder is X-linked adrenoleukodystrophy.

Excipients

Suitable optional excipients for use in the pharmaceutical compositions described herein include any commonly used excipients in pharmaceutics and are selected on the basis of compatibility with the active pharmaceutical agent and the release profile properties of the desired dosage form. Excipients include, but are not limited to, binders, fillers, flow aids, disintegrants, lubricants, glidants, polymeric carriers, plasticizers, stabilizers, surfactants, and the like. A summary of excipients described herein, may be found, for example in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and Pharmaceutical Dosage Forms and Drug Delivery Systems, Seventh Ed. (Lippincott Williams & Wilkins, 1999), herein incorporated by reference in their entirety.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinyl pyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinyl pyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

Fillers or diluents increase bulk in the pharmaceutical formulation. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinzed starch; compressible sugar, such as Di-Pac® (Amstar); hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; bentonite; and the like.

Glidants improve the flow characteristics of a powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Lubricants are compounds which prevent, reduce, or inhibit adhesion or friction of materials. Exemplary lubricants include, e.g., stearic acid; calcium hydroxide, talc; a hydrocarbon such as mineral oil, or hydrogenated vegetable oil such as hydrogenated soybean oil (Sterotex®), Lubritab®, Cutina®; higher fatty acids and their alkali-metal and alkaline earth metal salts, such as aluminum, calcium, magnesium, zinc, stearic acid, sodium stearates, magnesium stearate, glycerol, talc, waxes, Stearowet*, boric acid, sodium acetate, leucine, a polyethylene glycol or a methoxypolyethylene glycol such as Carbowax™, sodium oleate, glyceryl behenate (Compitrol 888®), glyceryl palmitostearate (Precirol®), colloidal silica such as Syloid™, Carb-O-Sil$^{g}$, a starch such as corn starch, silicone oil, a surfactant, and the like. Hydrophilic lubricants include, e.g., sodium stearyl fumarate (currently marketed under the trade name PRUV®), polyethylene glycol (PEG), magnesium lauryl sulfate, sodium lauryl sulfate (SLS), sodium benzoate, sodium chloride, and the like.

Disintegrants facilitate breakup or disintegration of the pharmaceutical formulation after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinyl pyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like.

Polymeric carriers include compounds such as polyvinyl pyrrolidone, e.g., polyvinylpolyvinyl pyrrolidone K12, polyvinyl pyrrolidone K17, polyvinyl pyrrolidone K25, or polyvinyl pyrrolidone K30, polyvinyl pyrrolidone vinyl acetate (PVPVA 64), hydroxypropylmethylcellulose (HPMC), hydroxypropylmethylcellulose acetylsuccinate (HPMC AS), and methylmethacrylate polymers (Eudragit polymers) and the like.

Stabilizers include compounds such as any anti-oxidation agents, e.g., butylated hydroxytoluene (BHT), sodium ascorbate, and tocopherol; buffers, acids, and the like.

Surfactants include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), d-α-tocopheryl polyethylene glycol succinate (Vitamin E TPGS); and the like.

The aforementioned excipients are given as examples only and are not meant to include all possible choices. Other suitable excipient classes include coloring agents, granulating agents, preservatives, anti-foaming agents, plasticizers, and the like. Additionally, many excipients can have more than one role or function, or can be classified in more than one group; the classifications are descriptive only, and are not intended to limit any use of a particular excipient.

Disclosed pharmaceutical formulations are administered to patients (animals and humans) in need of such treatment in dosages that will provide optimal pharmaceutical efficacy. It will be appreciated that the dose required for use in any particular application will vary from patient to patient, not only with the particular pharmaceutical formulation selected, but also with the nature of the condition being treated, the age and condition of the patient, concurrent medication or special diets then being followed by the patient, and other factors, with the appropriate dosage ultimately being at the discretion of the attendant physician.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific. In some embodiments, the compounds provided herein are synthesized as described in US 2019/0210950, which is herein incorporated by reference. In some embodiments, the compounds provided herein are synthesized as described in US 2021/0002208, which is herein incorporated by reference. In some embodiments, the compounds provided herein are synthesized as described in WO 2021/108549, which is herein incorporated by reference. In some embodiments, the compounds provided herein are synthesized as described below in Examples 1-33.

Example 1: Synthesis of 2-(3,5-dichloro-4-{[4-hydroxy-3-(propan-2-yl)phenyl]methyl}phenoxy)-N-(6-methoxypyridin-3-yl)acetamide (Compound 101)

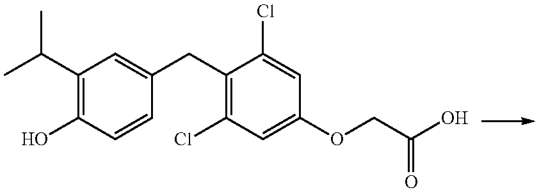

Compound 100

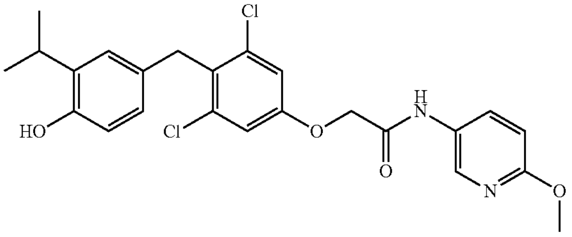

Compound 101

Step 1: To a solution of 2-(3,5-dichloro-4-(4-hydroxy-3-isopropylbenzyl)phenoxy)acetic acid (Compound 100) (100 mg, 0.3 mmol) in DCM (3 mL) was added DMF (cat). The mixture was cooled to 0° C. and oxalyl chloride (57 mg, 0.45 mmol) was added. The mixture was stirred at rt for 30 min, then concentrated in vacuo to afford 2-(3,5-dichloro-4-(4-hydroxy-3-isopropylbenzyl)phenoxy)acetyl chloride (110 mg, 95% yield) as a yellow oil.

Step 2: To solution of 2-(3,5-dichloro-4-(4-hydroxy-3-isopropylbenzyl)phenoxy)acetyl chloride (110 mg, 0.3 mmol) in DCM (2 mL) was added to a mixture of 6-methoxypyridin-3-amine (37 mg, 0.3 mmol) and triethylamine (61 mg, 0.6 mmol) in DCM (3 mL). The mixture was stirred at rt for 1h. Water (15 mL) was added, and the resultant mixture was extracted with DCM (20 mL*3). The combined organic phase was washed with brine (20 mL), dried over $Na_2SO_4$, concentrated in vacuo and purified by prep-HPLC to afford 2-(3,5-dichloro-4-(4-hydroxy-3-isopropylbenzyl)phenoxy)-N-(6-methoxypyridin-3-yl)acetamide (Compound 101) (30 mg, 21% yield) as a white solid. LCMS: M+H=475.2.

Example 2: Synthesis of 2-(3,5-dichloro-4-(4-hydroxy-3-isopropylbenzyl)phenoxy)-N-(pyrazin-2-yl)acetamide (Compound 102)

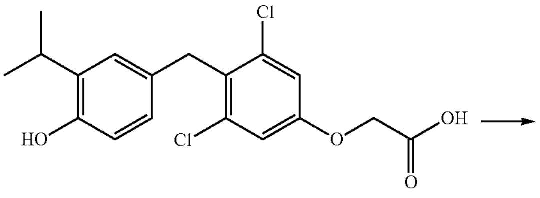

Compound 100

-continued

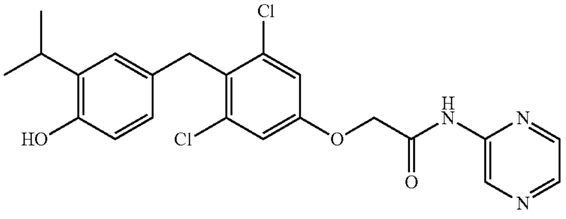

Compound 102

2-(3,5-Dichloro-4-(4-hydroxy-3-isopropylbenzyl)phenoxy)-N-(pyrazin-2-yl)acetamide (Compound 102) was synthesized according to the method of Example 1 using pyrazin-2-amine in step 2. LCMS: M+H=446.1.

Example 3: Synthesis of 2-(3,5-dichloro-4-(4-hydroxy-3-isopropylbenzyl)phenoxy)-N-(3,4-dimethylisoxazol-5-yl)acetamide (Compound 103)

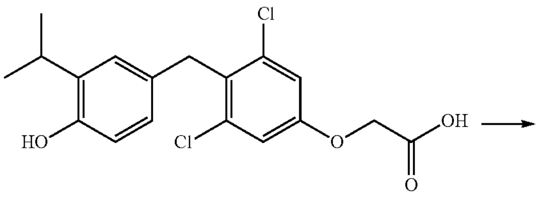

Compound 100

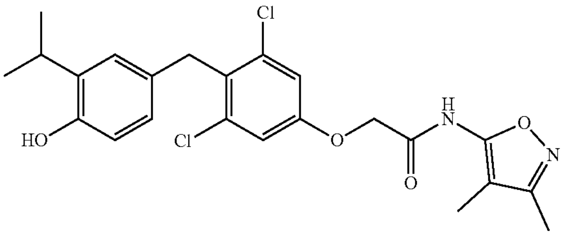

Compound 103

2-(3,5-Dichloro-4-(4-hydroxy-3-isopropylbenzyl)phenoxy)-N-(3,4-dimethylisoxazol-5-yl)acetamide (Compound 103) was synthesized according to the method of Example 1 using 3,4-dimethylisoxazol-5-amine in step 2. LCMS: M+H=463.1.

Example 4: Synthesis of 2-(3,5-dichloro-4-(4-hydroxy-3-isopropylbenzyl)phenoxy)-N-(pyridazin-3-yl)acetamide (Compound 104)

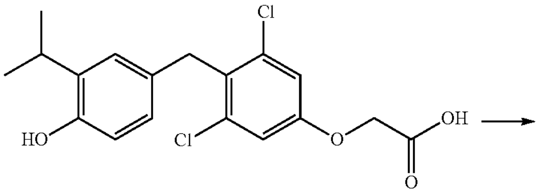

Compound 100

-continued

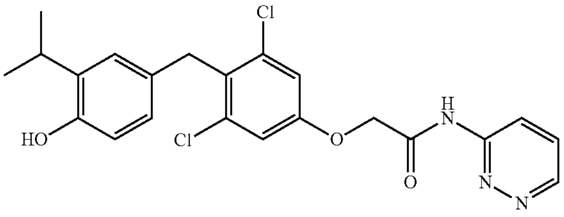

Compound 104

2-(3,5-Dichloro-4-(4-hydroxy-3-isopropylbenzyl)phenoxy)-N-(pyridazin-3-yl)acetamide (Compound 104) was synthesized according to the method of Example 1 using pyridazin-3-amine in step 2. LCMS: M+H=446.1.

Example 5: Synthesis of N-cyclohexyl-2-(3,5-dichloro-4-(4-hydroxy-3-isopropylbenzyl)phenoxy)acetamide (Compound 105)

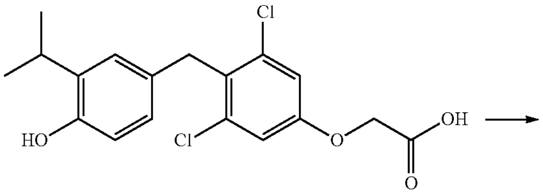

Compound 100

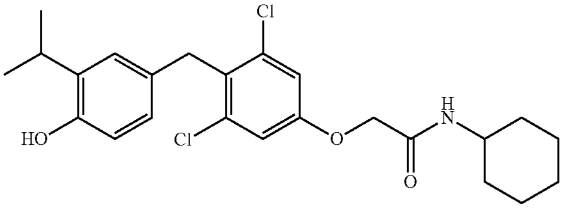

Compound 105

N-Cyclohexyl-2-(3,5-dichloro-4-(4-hydroxy-3-isopropylbenzyl)phenoxy)acetamide (Compound 105) was synthesized according to the method of Example 1 using cyclohexanamine in step 2. LCMS: M−H=448.2.

Example 6: Synthesis of N-(but-2-yn-1-yl)-2-(3,5-dichloro-4-(4-hydroxy-3-isopropylbenzyl)phenoxy)acetamide (Compound 106)

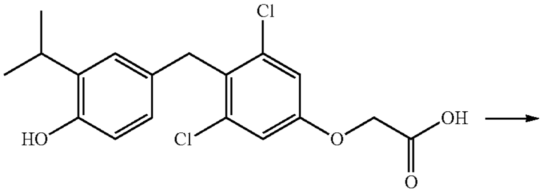

Compound 100

-continued

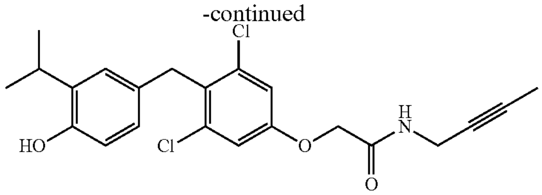

Compound 106

Step 1: A sealed tube (50 mL) was charged with 1-bromobut-2-yne (400 mg, 3.0 mmol) and $NH_3$(10 mL, 7 M in MeOH). The mixture was stirred at 60° C. overnight. The mixture was concentrated in vacuo to afford but-2-yn-1-amine hydrobromide (400 mg, 89% yield) as a yellow oil.

Step 2: N-(But-2-yn-1-yl)-2-(3,5-dichloro-4-(4-hydroxy-3-isopropylbenzyl)phenoxy)acetamide (Compound 106) was synthesized according to the method of Example 1 using but-2-yn-1-amine hydrobromide in step 2. LCMS: M−H=418.1.

Example 7: Synthesis of N-(but-2-yn-1-yl)-2-(3,5-dichloro-4-(4-hydroxy-3-isopropylbenzyl)phenoxy)-N-methylacetamide (Compound 107)

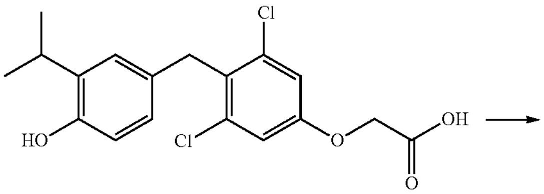

Compound 100

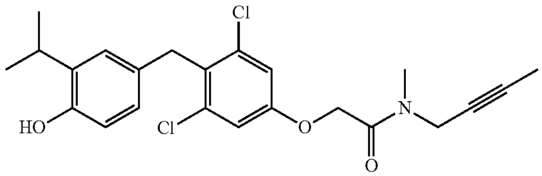

Compound 107

Step 1: To a mixture of N-methylprop-2-yn-1-amine (2.0 g, 29.0 mmol) in THE (20 mL) was added tert-butyldicarbonate (18.9 g, 87.0 mmol). The mixture was cooled to 40° C. and stirred for 2.0 h. Then the mixture was concentrated in vacuo to afford tert-butyl methyl (prop-2-yn-1-yl)carbamate (4.0 g, 82% yield) as a colorless oil.

Step 2: A solution tert-butyl methyl (prop-2-yn-1-yl) carbamate (1.0 g, 5.9 mmol) in DCM (5 mL) was added n-butyllithium (2.5M/THF) (2.8 mL, 7.1 mmol) at −70° C. The mixture was stirred for 1h and was added Iodomethane for another 1.0 h. Water (50 mL) was added, and the resultant mixture was extracted with DCM (20 mL*3). The combined organic phase was washed with brine (50 mL), dried over $Na_2SO_4$, concentrated in vacuo to afford crude tert-butyl but-2-yn-1-yl(methyl)carbamate (1.0 g, 92% yield) as a colorless oil.

Step 3: A solution of tert-butyl but-2-yn-1-yl (methyl) carbamate (1.0 g, 5.5 mmol) in DCM (2 mL) was added TFA (1.3 g, 11.0 mmol) was stirred at 0° C. for 2.0 h. The resulting mixture was concentrated in vacuo to afford N-methylbut-2-yn-1-amine (200.0 mg, 44% yield) as a colorless oil.

Step 4: N-(But-2-yn-1-yl)-2-(3,5-dichloro-4-(4-hydroxy-3-isopropylbenzyl)phenoxy)-N-methylacetamide (Compound 107) was synthesized according to the method of Example 1 using N-methylbut-2-yn-1-amine in step 2. LCMS: M+H=434.1.

Example 8: Synthesis of 2-(3,5-dichloro-4-(4-hydroxy-3-isopropylbenzyl)phenoxy)-N,N',N'-trimethylacetohydrazide (Compound 108)

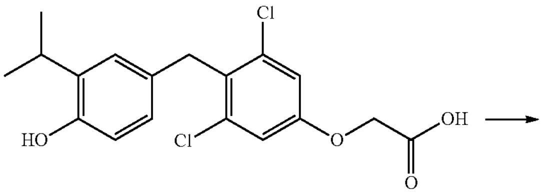

Compound 100

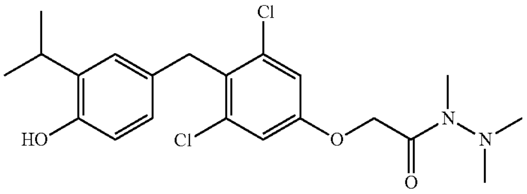

Compound 108

Step 1: To a mixture of tert-butyl 1-methylhydrazine-1-carboxylate (1.0 g, 6.8 mmol) in acetonitrile (10 mL) was added formaldehyde (37 wt. % in water) (5.26 mL, 68.4 mmol). The mixture was stirred at rt 2 hours. After that time, sodium cyanoborohydride (860.0 mg, 13.7 mmol) was added into the solution. The mixture was stirred at rt 2 hours, then the mixture was quenched by water (20 mL) and extracted with EtOAc (10 mL*2). The organic phase was washed by water (20 mL) and brine (20 mL), dried over $Na_2SO_4$, concentrated in vacuum and purified by silica gel column (DCM to DCM/MeOH=10:1) to afford tert-butyl 1,2,2-trimethylhydrazine-1-carboxylate (0.1 g, 8.4% yield) as a colorless oil.

Step 2: To a solution of tert-butyl 1,2,2-trimethylhydrazine-1-carboxylate (0.1 g, 573.9 μmol) in DCM (2 mL) was added HCl (1M/ether) (5.7 mL, 5.7 mmol). The mixture was stirred at rt 1 hour, then concentrated in vacuum to afford 1,1,2-trimethylhydrazine dihydrochloride (70 mg, 71.1% yield) as a white solid.

Step 3: 2-(3,5-Dichloro-4-(4-hydroxy-3-isopropylbenzyl)phenoxy)-N,N',N'-trimethylacetohydrazide (Compound 108) was synthesized according to the method of Example 1 using 1,1,2-trimethylhydrazine dihydrochloride in step 2. LCMS: M+H=425.0.

Example 9: Synthesis of 2-(3,5-dichloro-4-(4-hydroxy-3-isopropylbenzyl)phenoxy)-N-(pyrimidin-5-yl)acetamide (Compound 109)

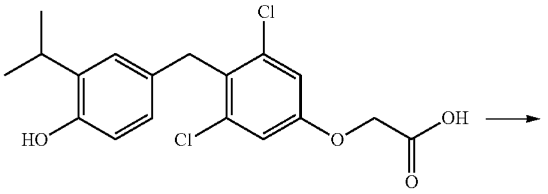

Compound 100

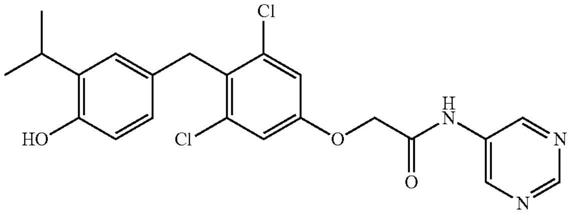

Compound 109

A solution of 2-(3,5-dichloro-4-(4-hydroxy-3-isopropylbenzyl)phenoxy)-N-(pyrimidin-5-yl)acetamide (Compound 100) (0.1 g, 271 μmol), pyrimidin-5-amine (25.8 mg, 271 μmol), HATU (124 mg, 325 μmol) and DIPEA (112 μL, 2.5 eq., 677 μmol) in DMF (2 mL) was stirred at room temperature for 5.0 h. Water (10 mL) was added, and the result mixture was extracted with EtOAc (10 mL*3). The combined organic phase was washed with water (15 mL*2), brine (15 mL), dried over $Na_2SO_4$, concentrated in vacuo and purified by prep-HPLC to afford 2-(3,5-dichloro-4-(4-hydroxy-3-isopropylbenzyl)phenoxy)-N-(pyrimidin-5-yl) acetamide (Compound 109) (20 mg, 44.8 μmol) as a white solid. LCMS: M+H=446.1.

Example 10: Synthesis of 2-(3,5-dichloro-4-(4-hydroxy-3-isopropylbenzyl)phenoxy)-N-(pyrimidin-4-yl)acetamide (Compound 110)

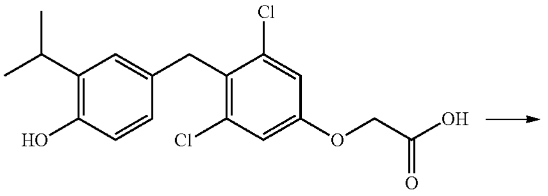

Compound 100

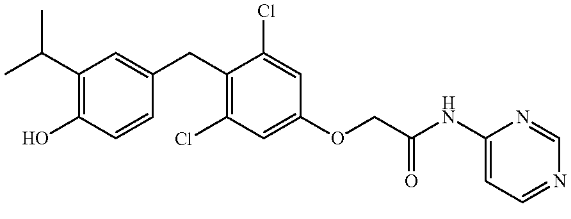

Compound 110

2-(3,5-Dichloro-4-(4-hydroxy-3-isopropylbenzyl)phenoxy)-N-(pyrimidin-4-yl)acetamide (Compound 110) was synthesized according to the method of Example 9 using pyrimidin-4-amine. LCMS: M+H=446.1.

Example 11: Synthesis of 2-(3,5-dichloro-4-(4-hydroxy-3-isopropylbenzyl)phenoxy)-N-((1R,2S)-2-fluorocyclopropyl)acetamide (Compound 111)

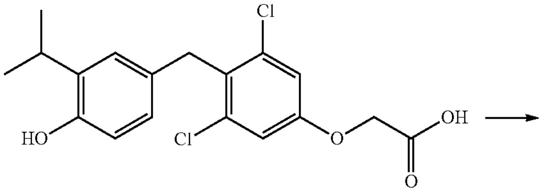

Compound 100

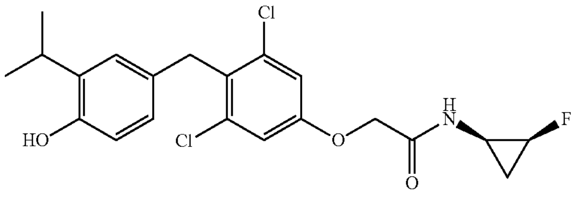

Compound 111

2-(3,5-Dichloro-4-(4-hydroxy-3-isopropylbenzyl)phenoxy)-N-((1R,2S)-2-fluorocyclopropyl)acetamide (Compound 111) was synthesized according to the method of Example 9 using (1R,2S)-2-fluorocyclopropan-1-amine. LCMS: M+H=426.1.

Example 12: Synthesis of 2-(3,5-dichloro-4-(4-hydroxy-3-isopropylbenzyl)phenoxy)-N-(3-fluoropropyl)acetamide (Compound 112)

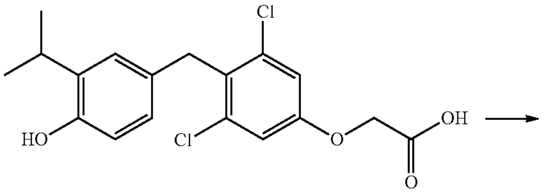

Compound 100

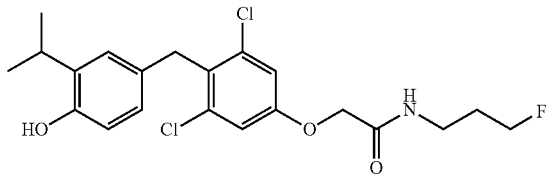

Compound 112

2-(3,5-Dichloro-4-(4-hydroxy-3-isopropylbenzyl)phenoxy)-N-(3-fluoropropyl)acetamide (Compound 112) was synthesized according to the method of Example 9 using 3-fluoropropan-1-amine. LCMS: M−H=426.1.

Example 13: Synthesis of 2-(3,5-dichloro-4-(4-hydroxy-3-isopropylbenzyl)phenoxy)-N-(6-methoxypyridazin-3-yl)acetamide (Compound 113)

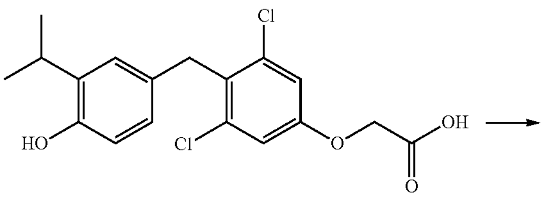

Compound 100

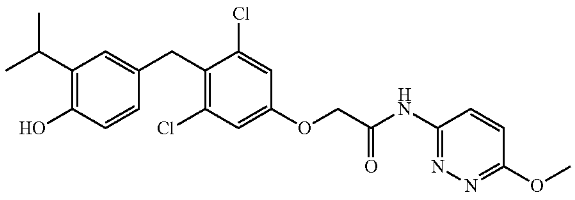

Compound 113

2-(3,5-Dichloro-4-(4-hydroxy-3-isopropylbenzyl)phenoxy)-N-(6-methoxypyridazin-3-yl)acetamide (Compound 113) was synthesized according to the method of Example 9 using 6-methoxypyridazin-3-amine. LCMS: M+H=476.2.

Example 14: Synthesis of 2-(3,5-dichloro-4-(4-hydroxy-3-isopropylbenzyl)phenoxy)-N-(pyridin-3-yl) acetamide (Compound 114)

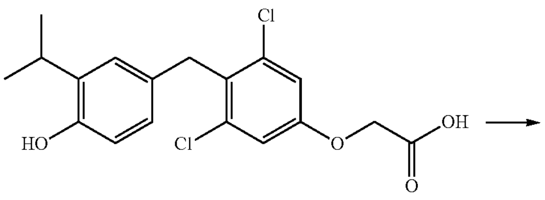

Compound 100

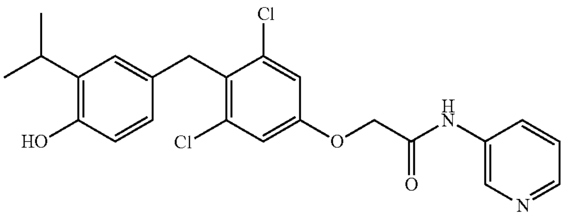

Compound 114

2-(3,5-Dichloro-4-(4-hydroxy-3-isopropylbenzyl)phenoxy)-N-(pyridin-3-yl)acetamide (Compound 114) was synthesized according to the method of Example 9 using pyridin-3-amine. LCMS: M+H=445.1.

Example 15: Synthesis of 2-(3,5-dichloro-4-(4-hydroxy-3-isopropylbenzyl)phenoxy)-N-(pyridin-4-yl) acetamide (Compound 115)

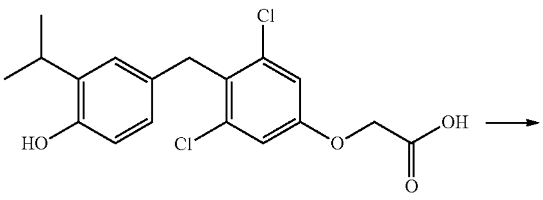

Compound 100

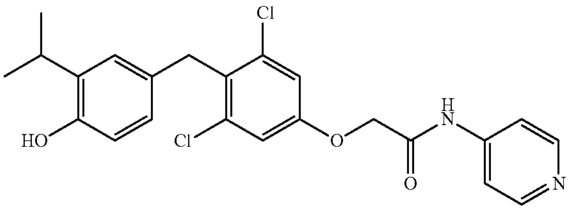

Compound 115

2-(3,5-Dichloro-4-(4-hydroxy-3-isopropylbenzyl)phenoxy)-N-(pyridin-4-yl)acetamide (Compound 115) was synthesized according to the method of Example 9 using pyridin-4-amine. LCMS: M+H=445.2.

Example 16: Synthesis of 2-(3,5-dichloro-4-(4-hydroxy-3-isopropylbenzyl)phenoxy)-N-(pyridazin-4-yl)acetamide (Compound 116)

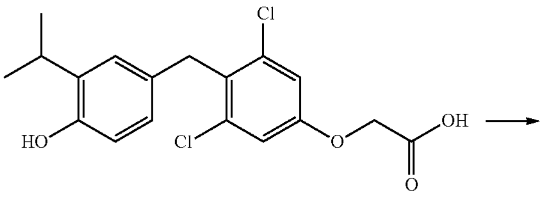

Compound 100

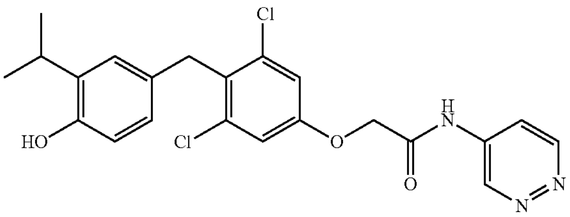

Compound 116

2-(3,5-Dichloro-4-(4-hydroxy-3-isopropylbenzyl)phenoxy)-N-(pyridazin-4-yl)acetamide (Compound 116) was synthesized according to the method of Example 9 using pyridazin-4-amine. LCMS: M+H=446.2.

Example 17: Synthesis of 2-(3,5-dichloro-4-(4-hydroxy-3-isopropylbenzyl)phenoxy)-1-(pyrrolidin-1-yl)ethan-1-one (Compound 117)

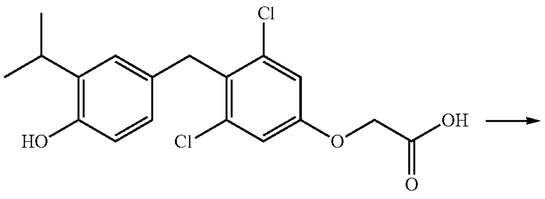

Compound 100

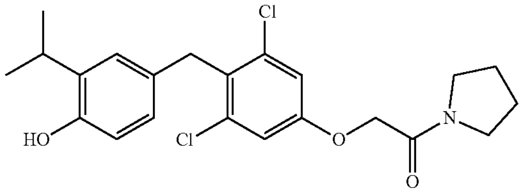

Compound 117

2-(3,5-Dichloro-4-(4-hydroxy-3-isopropylbenzyl)phenoxy)-1-(pyrrolidin-1-yl)ethan-1-one (Compound 117) was synthesized according to the method of Example 9 using pyrrolidine. LCMS: M+H=422.1.

Example 18: Synthesis of 1-(azetidin-1-yl)-2-(3,5-dichloro-4-(4-hydroxy-3-isopropylbenzyl)phenoxy) ethan-1-one (Compound 118)

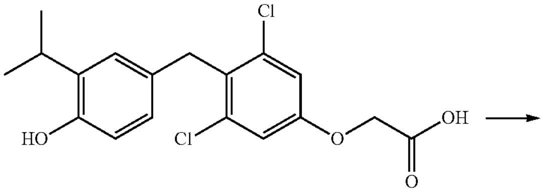

Compound 100

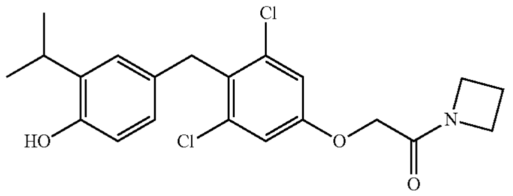

Compound 118

1-(Azetidin-1-yl)-2-(3,5-dichloro-4-(4-hydroxy-3-isopropylbenzyl)phenoxy)ethan-1-one (Compound 118) was synthesized according to the method of Example 9 using azetidine. LCMS: M+H=408.1.

Example 19: Synthesis of N-(tert-butyl)-2-(3,5-dichloro-4-(4-hydroxy-3-isopropylbenzyl)phenoxy) acetamide (Compound 119)

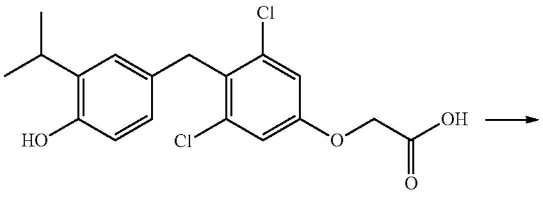

Compound 100

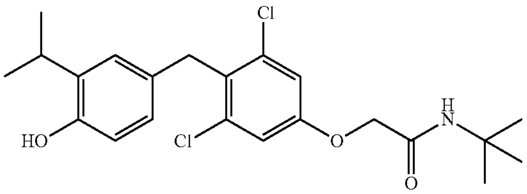

Compound 119

N-(tert-Butyl)-2-(3,5-dichloro-4-(4-hydroxy-3-isopropylbenzyl)phenoxy)acetamide (Compound 119) was synthesized according to the method of Example 9 using 2-methylpropan-2-amine. LCMS: M+H=424.1.

Example 20: Synthesis of 2-(3,5-dichloro-4-(4-hydroxy-3-isopropylbenzyl)phenoxy)-N-isobutyl-N-methylacetamide (Compound 120)

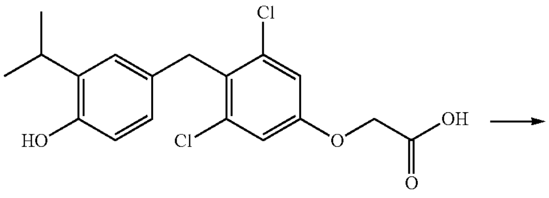

Compound 100

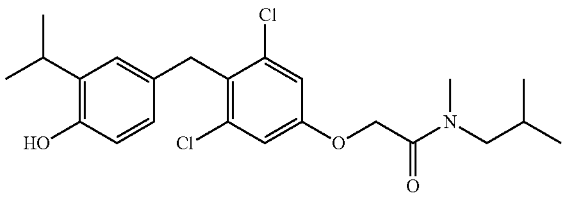

Compound 120

2-(3,5-Dichloro-4-(4-hydroxy-3-isopropylbenzyl)phenoxy)-N-isobutyl-N-methylacetamide (Compound 120) was synthesized according to the method of Example 9 using N,2-dimethylpropan-1-amine. LCMS: M+H=438.2.

Example 21: Synthesis of 2-(3,5-dichloro-4-(4-hydroxy-3-isopropylbenzyl)phenoxy)-N-isobutylacetamide (Compound 121)

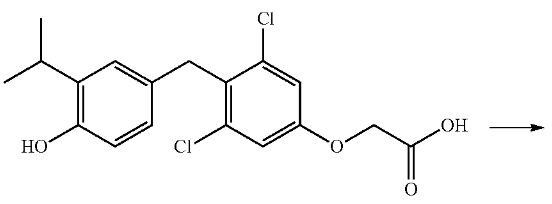

Compound 100

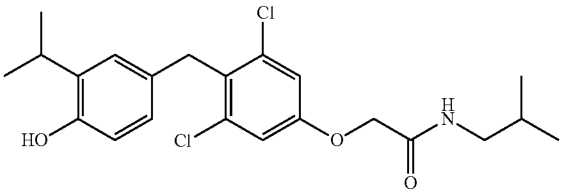

Compound 121

2-(3,5-Dichloro-4-(4-hydroxy-3-isopropylbenzyl)phenoxy)-N-isobutylacetamide (Compound 121) was synthesized according to the method of Example 9 using 2-methylpropan-1-amine. LCMS: M−H=422.1.

Example 22: Synthesis of 2-(3,5-dichloro-4-(4-hydroxy-3-isopropylbenzyl)phenoxy)-N-isopropyl-N-methylacetamide (Compound 122)

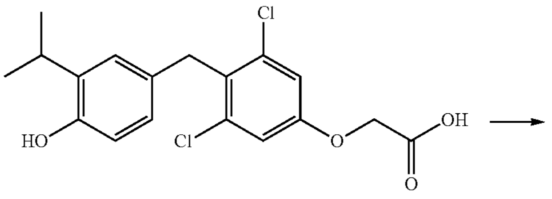

Compound 100

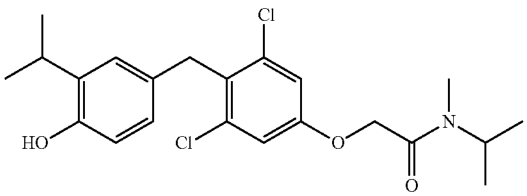

Compound 122

2-(3,5-dichloro-4-(4-hydroxy-3-isopropylbenzyl)phenoxy)-N-isopropyl-N-methylacetamide (Compound 122) was synthesized according to the method of Example 9 using N-methylpropan-2-amine. LCMS: M−H=422.1.

Example 23: Synthesis of 2-(3,5-dichloro-4-(4-hydroxy-3-isopropylbenzyl)phenoxy)-N-(2-hydroxyethyl)-N-methylacetamide (Compound 123)

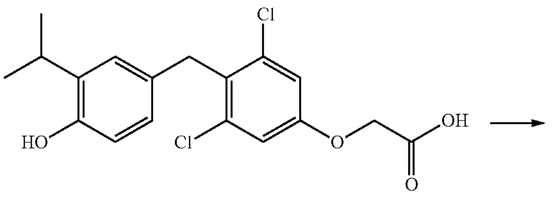

Compound 100

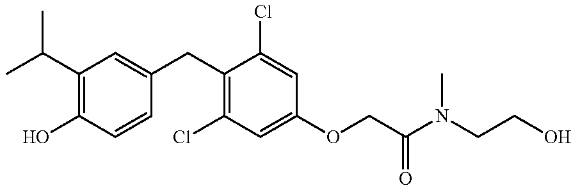

Compound 122

2-(3,5-Dichloro-4-(4-hydroxy-3-isopropylbenzyl)phenoxy)-N-(2-hydroxyethyl)-N-methylacetamide (Compound 123) was synthesized according to the method of Example 9 using 2-(methylamino)ethan-1-ol. LCMS: M−H=424.1.

Example 24: Synthesis of 2-(3,5-dichloro-4-(4-hydroxy-3-isopropylbenzyl)phenoxy)-N,N'-dimethylacetohydrazide (Compound 124)

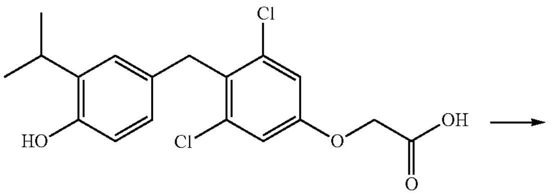

Compound 100

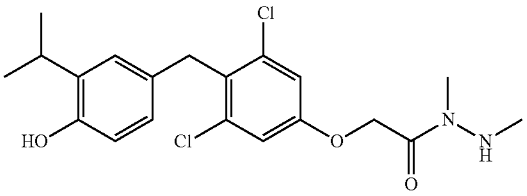

Compound 124

2-(3,5-Dichloro-4-(4-hydroxy-3-isopropylbenzyl)phenoxy)-N,N'-dimethylacetohydrazide (Compound 124) was synthesized according to the method of Example 9 using 1,2-dimethylhydrazine. LCMS: M+H=411.1.

Example 25: Synthesis of 2-(3,5-dichloro-4-(4-hydroxy-3-isopropylbenzyl)phenoxy)-N-(2-fluoroethyl)-N-methylacetamide (Compound 125)

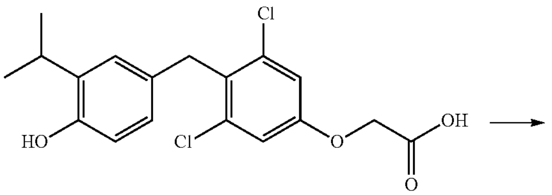

Compound 100

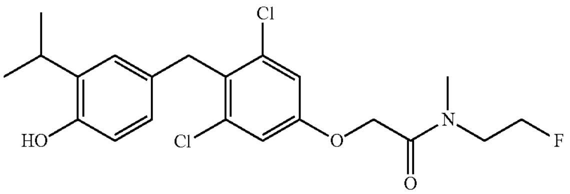

Compound 125

2-(3,5-Dichloro-4-(4-hydroxy-3-isopropylbenzyl)phenoxy)-N-(2-fluoroethyl)-N-methylacetamide (Compound 125) was synthesized according to the method of Example 9 using 2-fluoro-N-methylethan-1-amine. LCMS: M+H=428.1.

Example 26: Synthesis of 2-(3,5-dichloro-4-(4-hydroxy-3-isopropylbenzyl)phenoxy)-N-isopropylacetamide (Compound 126)

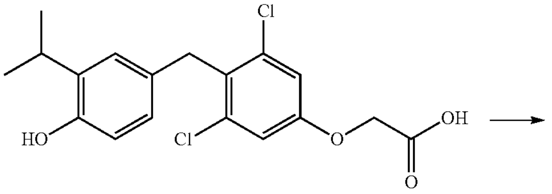

Compound 100

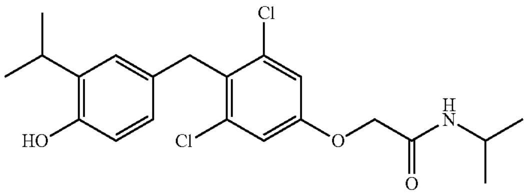

Compound 126

2-(3,5-Dichloro-4-(4-hydroxy-3-isopropylbenzyl)phenoxy)-N-isopropylacetamide (Compound 126) was synthesized according to the method of Example 9 using propan-2-amine. LCMS: M+H=410.1.

Example 27: Synthesis of N-cyclobutyl-2-(3,5-dichloro-4-(4-hydroxy-3-isopropylbenzyl)phenoxy)acetamide (Compound 127)

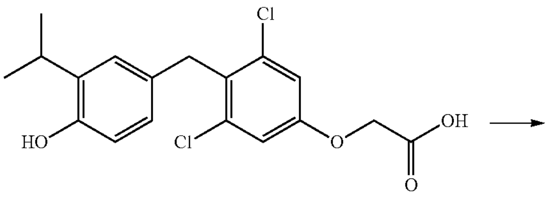

Compound 100

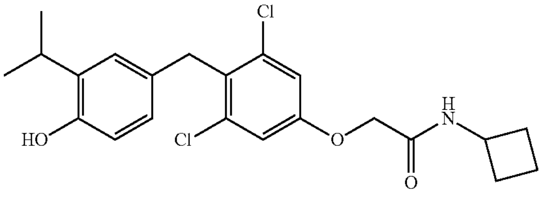

Compound 127

N-Cyclobutyl-2-(3,5-dichloro-4-(4-hydroxy-3-isopropylbenzyl)phenoxy)acetamide (Compound 127) was synthesized according to the method of Example 9 using cyclobutanamine. LCMS: M+H=422.2.

Example 28: Synthesis of N-allyl-2-(3,5-dichloro-4-(4-hydroxy-3-isopropylbenzyl)phenoxy)-N-methylacetamide (Compound 128)

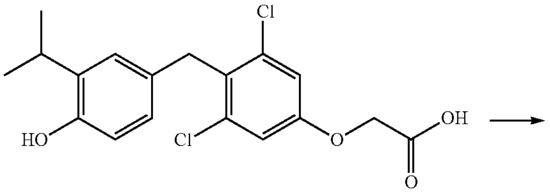

Compound 100

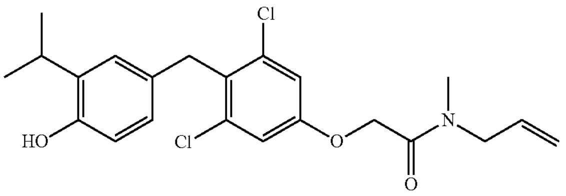

Compound 128

N-Allyl-2-(3,5-dichloro-4-(4-hydroxy-3-isopropylbenzyl)phenoxy)-N-methylacetamide (Compound 128) was synthesized according to the method of Example 9 using N-methylprop-2-en-1-amine. LCMS: M−H=420.1.

Example 29: Synthesis of 2-(3,5-dichloro-4-(4-hydroxy-3-isopropylbenzyl)phenoxy)-N-methyl-N-propylacetamide (Compound 129)

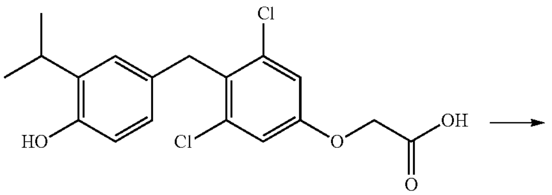

Compound 100

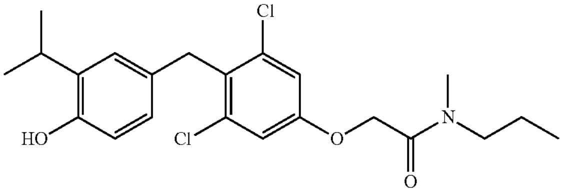

Compound 129

2-(3,5-Dichloro-4-(4-hydroxy-3-isopropylbenzyl)phenoxy)-N-methyl-N-propylacetamide (Compound 129) was synthesized according to the method of Example 9 using N-methylpropan-1-amine. LCMS: M−H=422.1.

Example 30: Synthesis of 2-(3,5-dichloro-4-(4-hydroxy-3-isopropylbenzyl)phenoxy)-N-ethyl-N-methylacetamide (Compound 130)

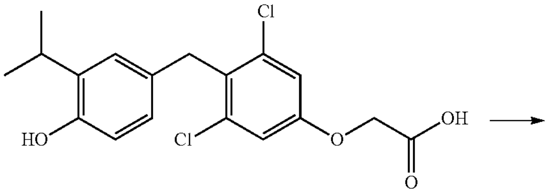

Compound 100

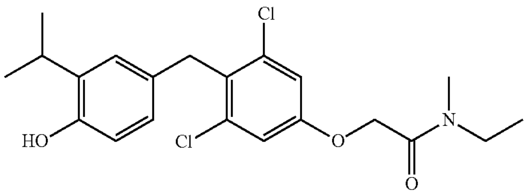

Compound 130

2-(3,5-Dichloro-4-(4-hydroxy-3-isopropylbenzyl)phenoxy)-N-ethyl-N-methylacetamide (Compound 130) was synthesized according to the method of Example 9 using N-methylethanamine. LCMS: M+H=410.2.

Example 31: Synthesis of 2-(3,5-dichloro-4-(4-hydroxy-3-isopropylbenzyl)phenoxy)-N-methyl-N-(2,2,2-trifluoroethyl)acetamide (Compound 131)

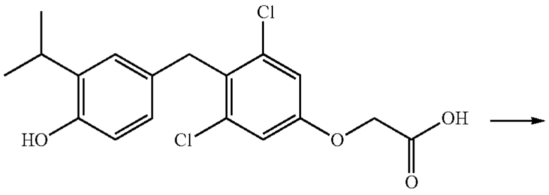

Compound 100

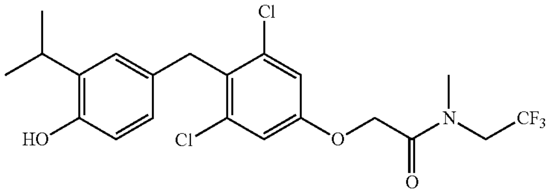

Compound 131

To a solution of 2-(3,5-dichloro-4-(4-hydroxy-3-isopropylbenzyl)phenoxy)acetic acid (100 mg, 0.3 mmol) in DMF (3 mL) was added 2,2,2-trifluoro-N-methylethan-1-amine (134 mg, 0.9 mmol), 1-(3-dimethylaminopropyl)-3-ethylcarbodiimide hydrochloride (EDCI) (77 mg, 0.4 mmol), 1-hydroxybenzotriazole (HOBT) (55 mg, 0.4 mmol) and N,N-diisopropylethylamine (105 mg, 0.8 mmol). The mixture was stirred at rt overnight. Water (20 mL) was added. The mixture was extracted with EtOAc (15 mL*2). The combined organic phase was washed with brine (20 mL), dried over $Na_2SO_4$, concentrated in vacuo and purified by prep-HPLC to afford 2-(3,5-dichloro-4-(4-hydroxy-3-isopropylbenzyl)phenoxy)-N-methyl-N-(2,2,2-trifluoroethyl)acetamide (Compound 131) (50 mg, 36% yield) as a white solid. LCMS: M−H=462.1.

Example 32: Synthesis of 2-(3,5-dichloro-4-(4-hydroxy-3-isopropylbenzyl)phenoxy)-N-(2,2-difluoroethyl)-N-methylacetamide (Compound 132)

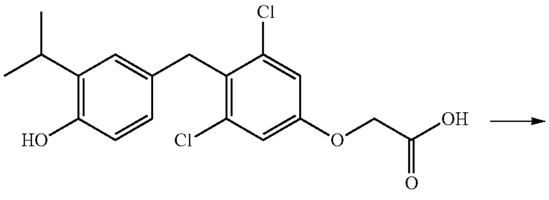

Compound 100

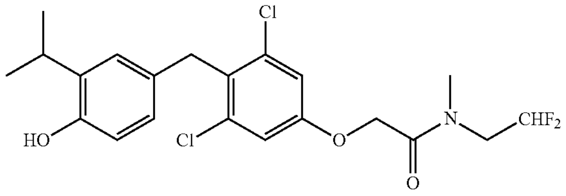

Compound 132

2-(3,5-Dichloro-4-(4-hydroxy-3-isopropylbenzyl)phenoxy)-N-(2,2-difluoroethyl)-N-methylacetamide (Compound 132) was synthesized according to the method of Example 31 using 2,2-difluoro-N-methylethan-1-amine hydrochloride. LCMS: M+H=446.1.

Example 33: Synthesis of 2-(3,5-dichloro-4-(4-hydroxy-3-isopropylbenzyl)phenoxy)-1-morpholinoethan-1-one (Compound 133)

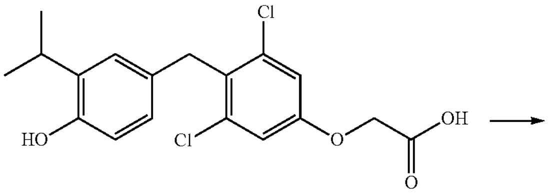

Compound 100

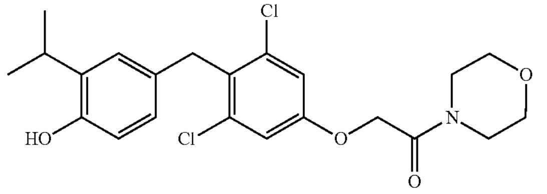

Compound 133

2-(3,5-Dichloro-4-(4-hydroxy-3-isopropylbenzyl)phenoxy)-1-morpholinoethan-1-one (Compound 133) was synthesized according to the method of Example 31 using morpholine. LCMS: M−H=436.0.

Example 34: FAAH Substrate Evaluation

Purified recombinant human FAAH (rhFAAH) was purchased from Cayman Chemical (Ann Arbor, MI, USA). The total volume for each incubation was 400 μL containing a final 0.5 ng/μL rhFAAH, 1 μM test compound, 1.25% ethanol or 1 μM PF-3845 (FAAH inhibitor), and 0.1% bovine serum albumin in Tris-EDTA buffer at pH 8.0). The positive control was LL-341001. The incubation was conducted at the room temperature. At 0, 5, 15, 30 and 60 minutes, an aliquot of 30 μL reaction mixtures was removed and mixed with 300 μL acetonitrile containing 5 ng/mL terfenadine and 10 ng/mL tolbutamide as internal standards to quench the reaction. The resulting mixture was centrifuged at 4000 rpm, 4° C. for 15 minutes, and 100 μL supernatant was ready for LC-MS/MS analysis to measure the formation of acid metabolite.

LC-MS/MS Analysis

Acquity Ultra Performance LC system from Waters was used for sample analysis. The chromatography was performed on a reverse phase Kinetex 2.6 μm C18 column, 2.1×30 mm, 100 Å. The mobile phase A comprised of 0.1% formic acid in water and mobile phase B comprised of 0.1% formic acid in acetonitrile with a 2-min run time at the flow rate of 0.8 mL/min for the acid metabolite from positive control or a 1.5 min run time at the flow rate of 0.9 mL/min for the acid metabolite of test compounds. The mass spectrometer (API-5500 and API Q Trap 4000 Applied Biosystems/MDS SCIEX Instruments, Framingham, MA, USA) was operated under ESI positive or negative ion MRM mode.

Data Analysis

The formation of acid metabolite was monitored and quantified using one calibration point of 1 μM. The observed rate constant (ke) for the acid metabolite formation was calculated by plotting the metabolite concentration versus time of incubation with the slope being ke and is shown in Table 1.

TABLE 1

| Compound | Structure | ke |
|---|---|---|
| 1 | 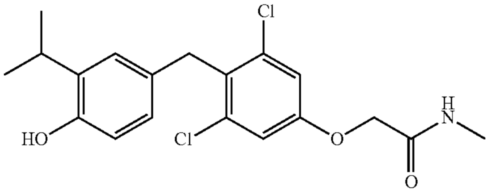 | A |
| 2 | 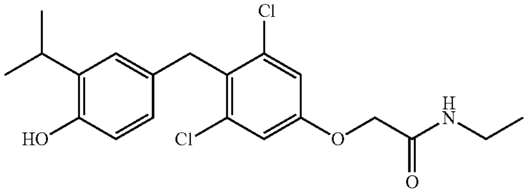 | A |
| 3 | 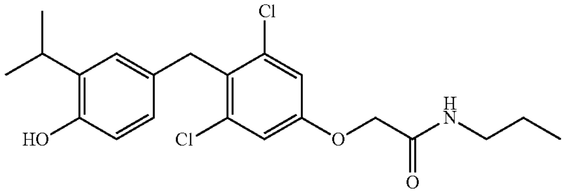 [SMILES: CCCNC(=O)COc1cc(Cl)c(Cc2ccc(O)c(C(C)C)c2)c(Cl)c1] | A |

TABLE 1-continued
| Compound | Structure | ke |
| --- | --- | --- |
| 4 | 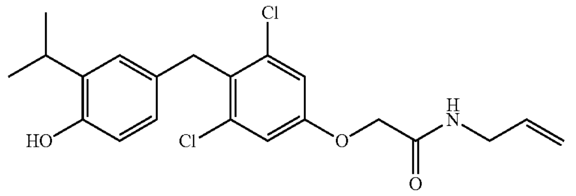 [SMILES: C=CCNC(=O)COc1cc(Cl)c(Cc2ccc(O)c(C(C)C)c2)c(Cl)c1] | A |
| 5 | 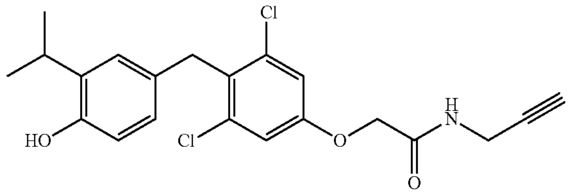 [SMILES: C#CCNC(=O)COc1cc(Cl)c(Cc2ccc(O)c(C(C)C)c2)c(Cl)c1] | A |
| 6 | 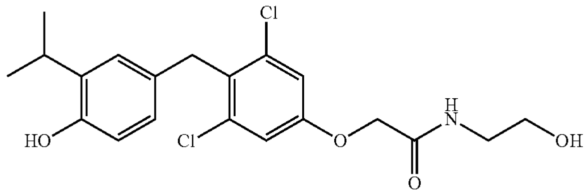 [SMILES: CC(C)c1cc(Cc2c(Cl)cc(OCC(=O)NCCO)cc2Cl)ccc1O] | A |
| 7 | 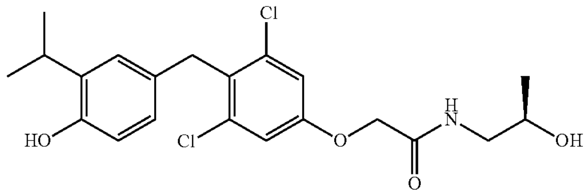 [SMILES: CC(C)c1cc(Cc2c(Cl)cc(OCC(=O)NC[C@@H](C)O)cc2Cl)ccc1O] | B |
| 8 | 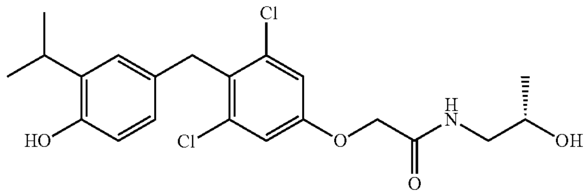 [SMILES: CC(C)c1cc(Cc2c(Cl)cc(OCC(=O)NC[C@H](C)O)cc2Cl)ccc1O] | B |
| 9 | 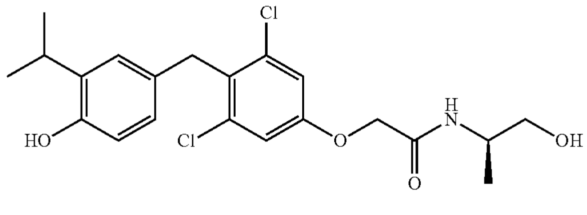 [SMILES: CC(C)c1cc(Cc2c(Cl)cc(OCC(=O)N[C@H](C)CO)cc2Cl)ccc1O] | A |
| 10 | 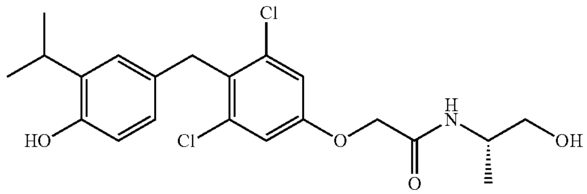 [SMILES: CC(C)c1cc(Cc2c(Cl)cc(OCC(=O)N[C@@H](C)CO)cc2Cl)ccc1O] | A |

TABLE 1-continued
| Compound | Structure | ke |
|---|---|---|
| 11 | 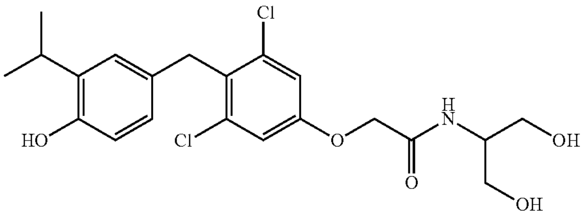 [SMILES: CC(C)c1cc(Cc2c(Cl)cc(OCC(=O)NC(CO)CO)cc2Cl)ccc1O] | B |
| 12 | 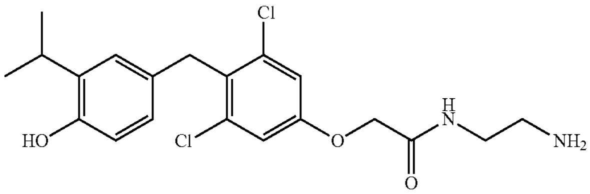 [SMILES: CC(C)c1cc(Cc2c(Cl)cc(OCC(=O)NCCN)cc2Cl)ccc1O] | B |
| 13 | 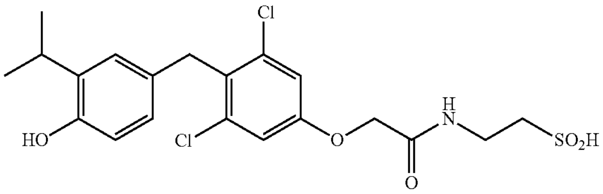 | B |
| 14 | 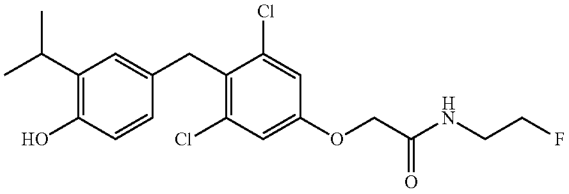 [SMILES: CC(C)c1cc(Cc2c(Cl)cc(OCC(=O)NCCF)cc2Cl)ccc1O] | A |
| 15 | 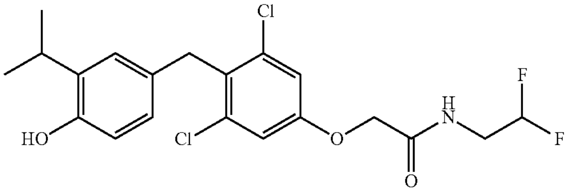 [SMILES: CC(C)c1cc(Cc2c(Cl)cc(OCC(=O)NCC(F)F)cc2Cl)ccc1O] | A |
| 16 | 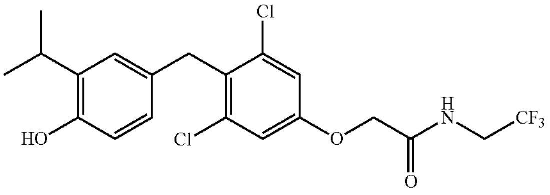 [SMILES: CC(C)c1cc(Cc2c(Cl)cc(OCC(=O)NCC(F)(F)F)cc2Cl)ccc1O] | A |
| 17 | 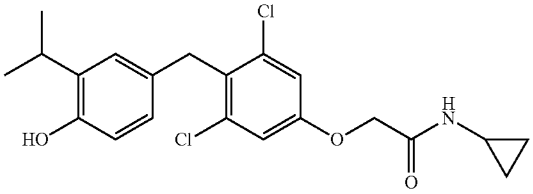 [SMILES: CC(C)c1cc(Cc2c(Cl)cc(OCC(=O)NC3CC3)cc2Cl)ccc1O] | A |

TABLE 1-continued
| Compound | Structure | ke |
|---|---|---|
| 18 | 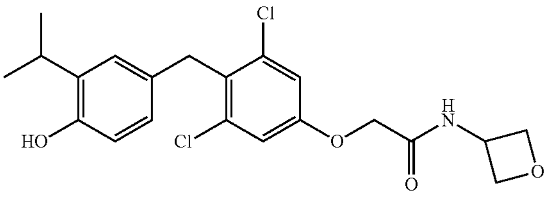 [SMILES: CC(C)c1cc(Cc2c(Cl)cc(OCC(=O)NC3COC3)cc2Cl)ccc1O] | A |
| 19 | 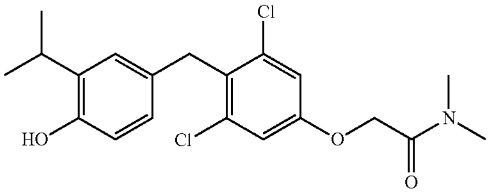 [SMILES: CC(C)c1cc(Cc2c(Cl)cc(OCC(=O)N(C)C)cc2Cl)ccc1O] | B |
| 20 | 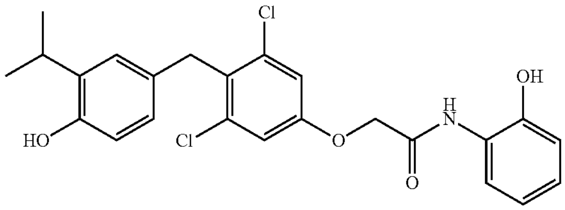 [SMILES: CC(C)c1cc(Cc2c(Cl)cc(OCC(=O)Nc3ccccc3O)cc2Cl)ccc1O] | A |
| 21 | 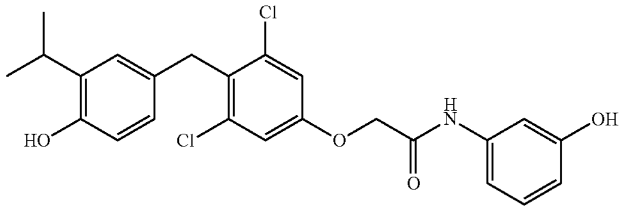 [SMILES: CC(C)c1cc(Cc2c(Cl)cc(OCC(=O)Nc3cccc(O)c3)cc2Cl)ccc1O] | A |
| 22 | 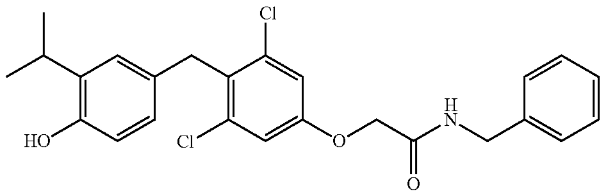 [SMILES: CC(C)c1cc(Cc2c(Cl)cc(OCC(=O)NCc3ccccc3)cc2Cl)ccc1O] | A |
| 23 | 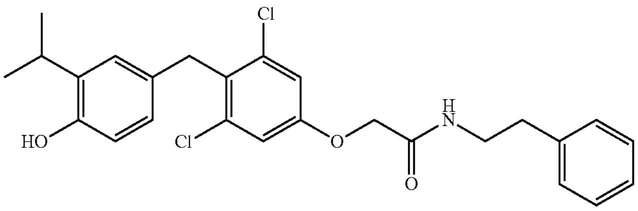 [SMILES: CC(C)c1cc(Cc2c(Cl)cc(OCC(=O)NCCc3ccccc3)cc2Cl)ccc1O] | B |
| 24 | 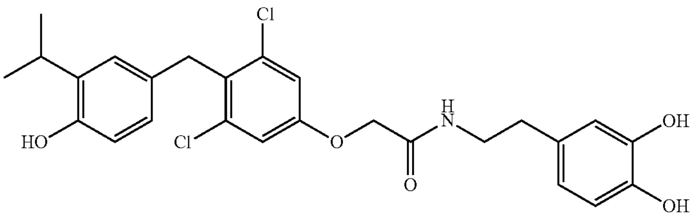 [SMILES: CC(C)c1cc(Cc2c(Cl)cc(OCC(=O)NCCc3ccc(O)c(O)c3)cc2Cl)ccc1O] | B |

TABLE 1-continued
| Compound | Structure | ke |
|---|---|---|
| 25 | 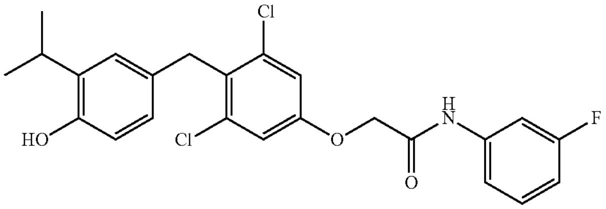 [SMILES: CC(C)c1cc(Cc2c(Cl)cc(OCC(=O)Nc3cccc(F)c3)cc2Cl)ccc1O] | A |
| 26 | 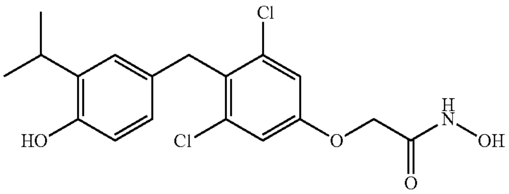 [SMILES: CC(C)c1cc(Cc2c(Cl)cc(OCC(=O)NO)cc2Cl)ccc1O] | A |
| 27 | 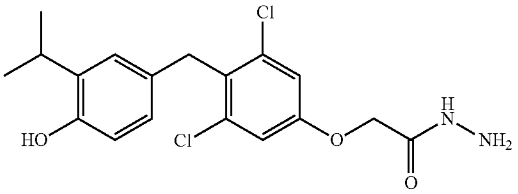 [SMILES: CC(C)c1cc(Cc2c(Cl)cc(OCC(=O)NN)cc2Cl)ccc1O] | A |
| 28 | 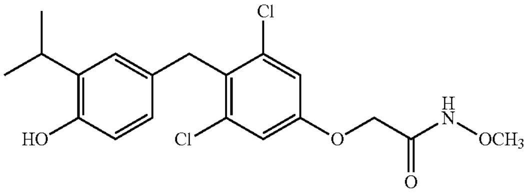 [SMILES: CONC(=O)COc1cc(Cl)c(Cc2ccc(O)c(C(C)C)c2)c(Cl)c1] | A |
| 29 | 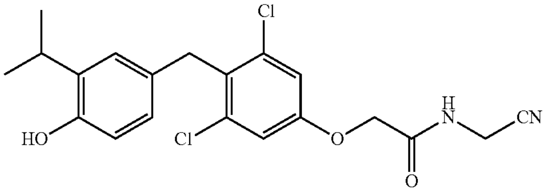 [SMILES: CC(C)c1cc(Cc2c(Cl)cc(OCC(=O)NCC#N)cc2Cl)ccc1O] | A |
| 30 | 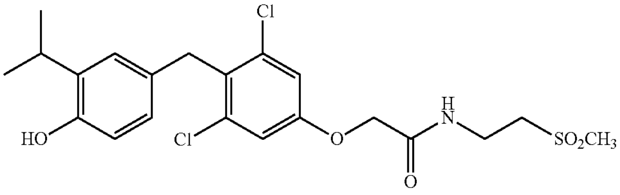 [SMILES: CC(C)c1cc(Cc2c(Cl)cc(OCC(=O)NCCS(C)(=O)=O)cc2Cl)ccc1O] | A |
| 31 | 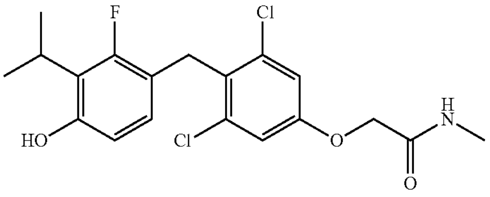 [SMILES: CNC(=O)COc1cc(Cl)c(Cc2ccc(O)c(C(C)C)c2F)c(Cl)c1] | A |

TABLE 1-continued
| Compound | Structure | ke |
|---|---|---|
| 32 | 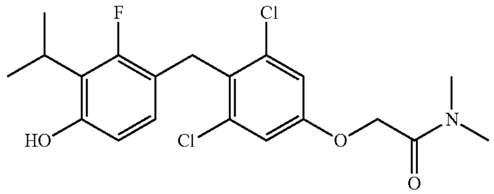 [SMILES: CC(C)c1c(O)ccc(Cc2c(Cl)cc(OCC(=O)N(C)C)cc2Cl)c1F] | A |
| 33 | 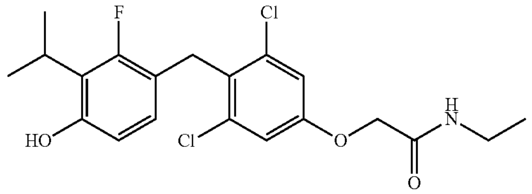 [SMILES: CCNC(=O)COc1cc(Cl)c(Cc2ccc(O)c(C(C)C)c2F)c(Cl)c1] | A |
| 34 | 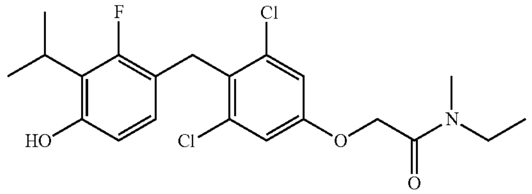 [SMILES: CCN(C)C(=O)COc1cc(Cl)c(Cc2ccc(O)c(C(C)C)c2F)c(Cl)c1] | C |
| 35 | 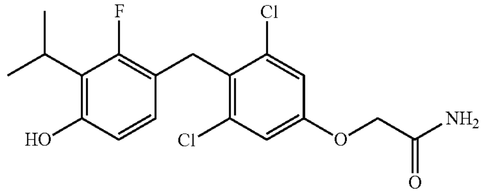 [SMILES: CC(C)c1c(O)ccc(Cc2c(Cl)cc(OCC(N)=O)cc2Cl)c1F] | A |
| 36 | 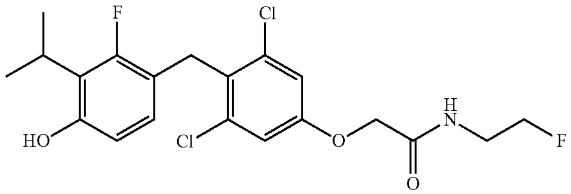 [SMILES: CC(C)c1c(O)ccc(Cc2c(Cl)cc(OCC(=O)NCCF)cc2Cl)c1F] | A |
| 37 | 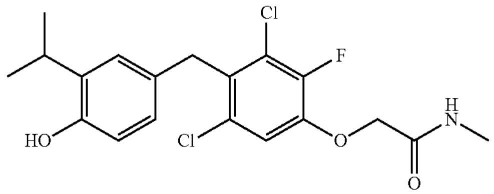 [SMILES: CNC(=O)COc1cc(Cl)c(Cc2ccc(O)c(C(C)C)c2)c(Cl)c1F] | B |
| 38 | 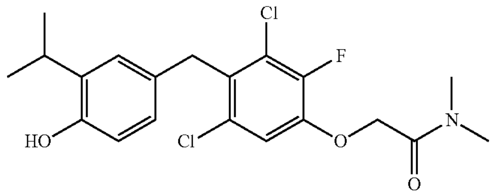 [SMILES: CC(C)c1cc(Cc2c(Cl)cc(OCC(=O)N(C)C)c(F)c2Cl)ccc1O] | B |

TABLE 1-continued
| Compound | Structure | ke |
|---|---|---|
| 39 | 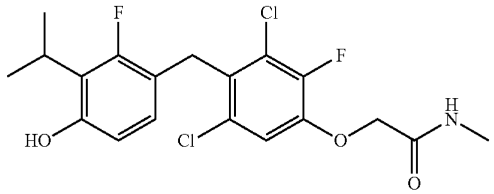 [SMILES: CNC(=O)COc1cc(Cl)c(Cc2ccc(O)c(C(C)C)c2F)c(Cl)c1F] | B |
| 40 | 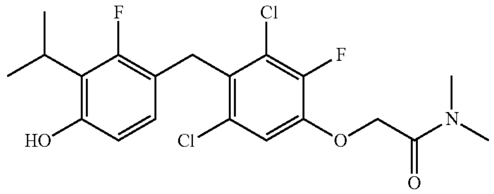 [SMILES: CC(C)c1c(O)ccc(Cc2c(Cl)cc(OCC(=O)N(C)C)c(F)c2Cl)c1F] | B |
| 41 | 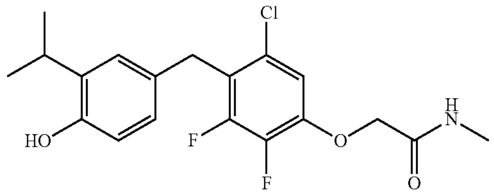 [SMILES: CNC(=O)COc1cc(Cl)c(Cc2ccc(O)c(C(C)C)c2)c(F)c1F] | NT |
| 42 | 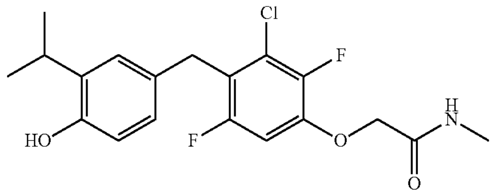 [SMILES: CNC(=O)COc1cc(F)c(Cc2ccc(O)c(C(C)C)c2)c(Cl)c1F] | A |
| 43 | 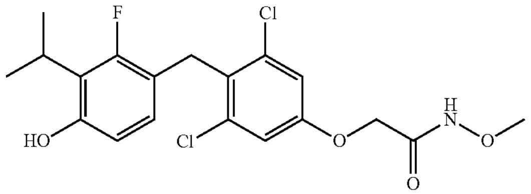 [SMILES: CONC(=O)COc1cc(Cl)c(Cc2ccc(O)c(C(C)C)c2F)c(Cl)c1] | NT |
| 44 | 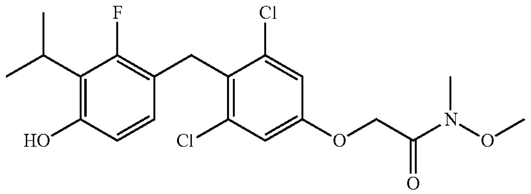 [SMILES: CON(C)C(=O)COc1cc(Cl)c(Cc2ccc(O)c(C(C)C)c2F)c(Cl)c1] | A |
| 45 | 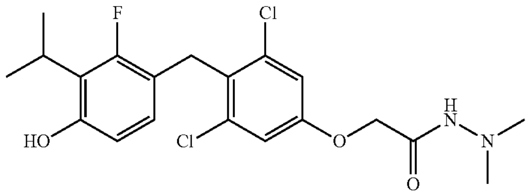 [SMILES: CC(C)c1c(O)ccc(Cc2c(Cl)cc(OCC(=O)NN(C)C)cc2Cl)c1F] | A |

TABLE 1-continued
| Compound | Structure | ke |
| --- | --- | --- |
| 101 | 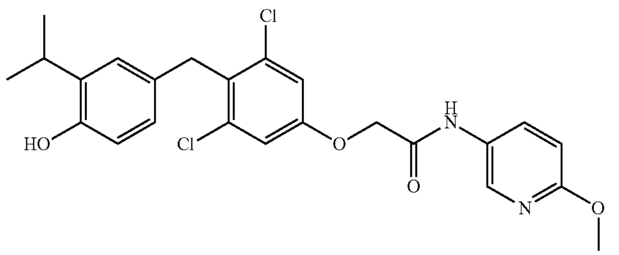 [SMILES: COc1ccc(NC(=O)COc2cc(Cl)c(Cc3ccc(O)c(C(C)C)c3)c(Cl)c2)cn1] | A |
| 102 | 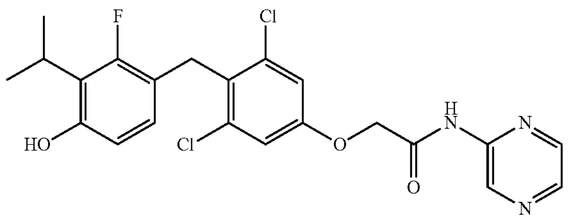 [SMILES: CC(C)c1c(O)ccc(Cc2c(Cl)cc(OCC(=O)Nc3cnccn3)cc2Cl)c1F] | A |
| 103 | 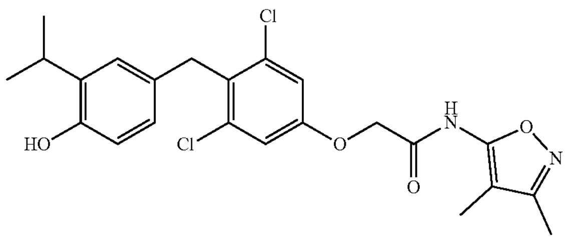 [SMILES: Cc1noc(NC(=O)COc2cc(Cl)c(Cc3ccc(O)c(C(C)C)c3)c(Cl)c2)c1C] | A |
| 104 | 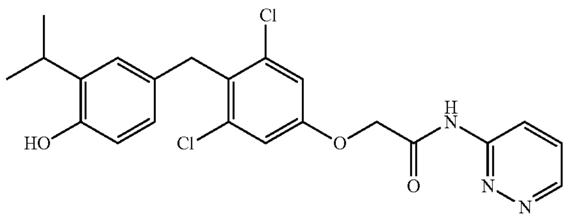 [SMILES: CC(C)c1cc(Cc2c(Cl)cc(OCC(=O)Nc3cccnn3)cc2Cl)ccc1O] | A |
| 105 | 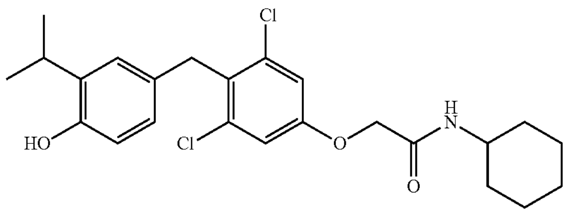 [SMILES: CC(C)c1cc(Cc2c(Cl)cc(OCC(=O)NC3CCCCC3)cc2Cl)ccc1O] | C |
| 106 | 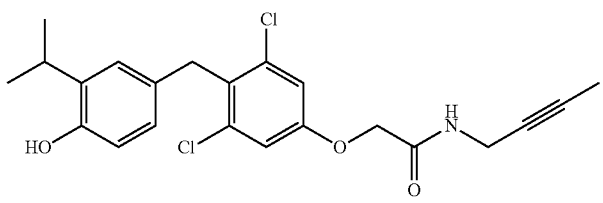 [SMILES: CC#CCNC(=O)COc1cc(Cl)c(Cc2ccc(O)c(C(C)C)c2)c(Cl)c1] | B |
| 107 | 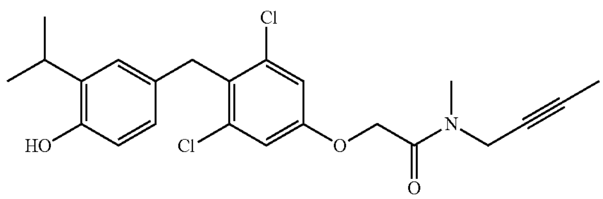 [SMILES: CC#CCN(C)C(=O)COc1cc(Cl)c(Cc2ccc(O)c(C(C)C)c2)c(Cl)c1] | B |

TABLE 1-continued
| Compound | Structure | ke |
| --- | --- | --- |
| 108 | 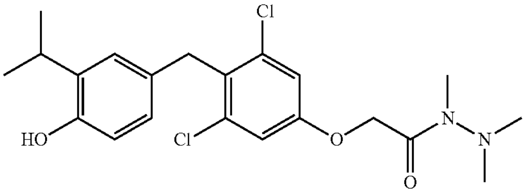 [SMILES: CC(C)c1cc(Cc2c(Cl)cc(OCC(=O)N(C)N(C)C)cc2Cl)ccc1O] | B |
| 109 | 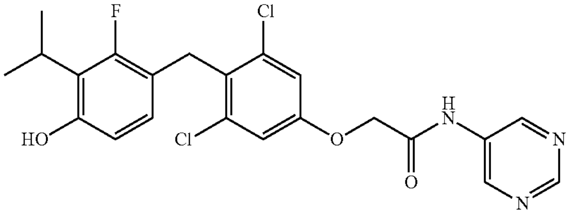 [SMILES: CC(C)c1c(O)ccc(Cc2c(Cl)cc(OCC(=O)Nc3cncnc3)cc2Cl)c1F] | A |
| 110 | 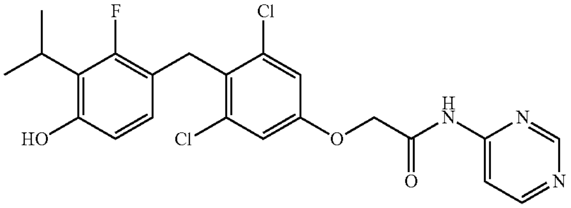 [SMILES: CC(C)c1c(O)ccc(Cc2c(Cl)cc(OCC(=O)Nc3ccncn3)cc2Cl)c1F] | A |
| 111 | 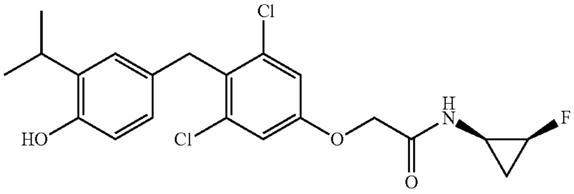 [SMILES: CC(C)c1cc(Cc2c(Cl)cc(OCC(=O)N[C@@H]3C[C@@H]3F)cc2Cl)ccc1O] | A |
| 112 | 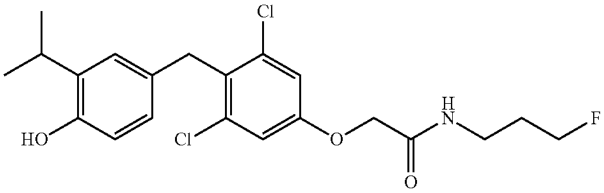 [SMILES: CC(C)c1cc(Cc2c(Cl)cc(OCC(=O)NCCCF)cc2Cl)ccc1O] | A |
| 113 | 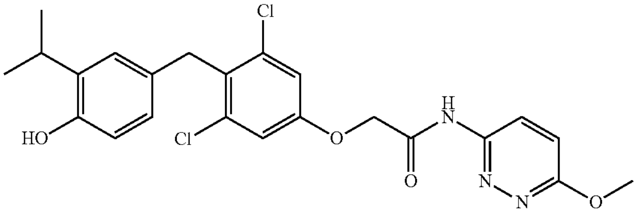 [SMILES: COc1ccc(NC(=O)COc2cc(Cl)c(Cc3ccc(O)c(C(C)C)c3)c(Cl)c2)nn1] | A |
| 114 | 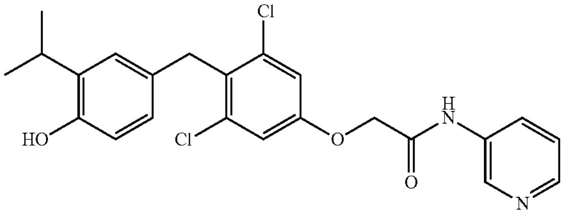 [SMILES: CC(C)c1cc(Cc2c(Cl)cc(OCC(=O)Nc3cccnc3)cc2Cl)ccc1O] | A |

TABLE 1-continued
| Compound | Structure | ke |
|---|---|---|
| 115 | 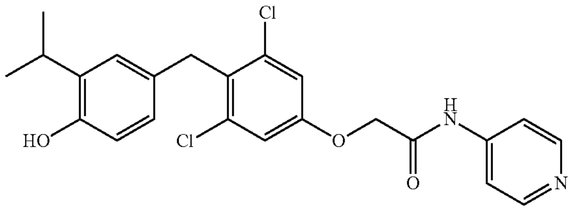 [SMILES: CC(C)c1cc(Cc2c(Cl)cc(OCC(=O)Nc3ccncc3)cc2Cl)ccc1O] | A |
| 116 | 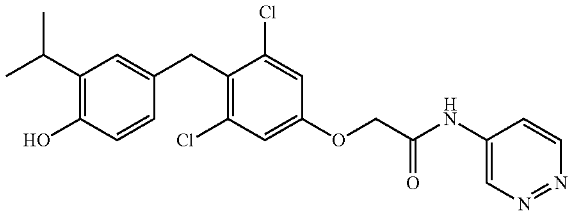 [SMILES: CC(C)c1cc(Cc2c(Cl)cc(OCC(=O)Nc3ccnnc3)cc2Cl)ccc1O] | A |
| 117 | 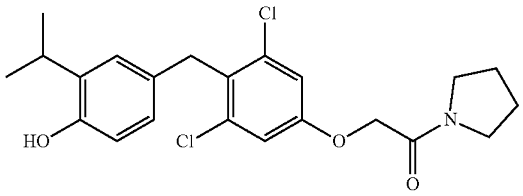 [SMILES: CC(C)c1cc(Cc2c(Cl)cc(OCC(=O)N3CCCC3)cc2Cl)ccc1O] | B |
| 118 | 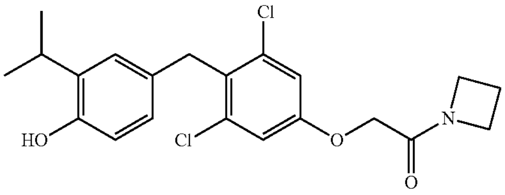 [SMILES: CC(C)c1cc(Cc2c(Cl)cc(OCC(=O)N3CCC3)cc2Cl)ccc1O] | B |
| 119 | 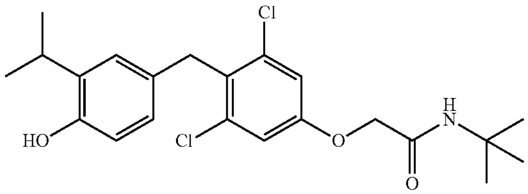 [SMILES: CC(C)c1cc(Cc2c(Cl)cc(OCC(=O)NC(C)(C)C)cc2Cl)ccc1O] | C |
| 120 | 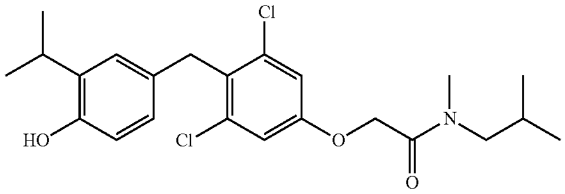 [SMILES: CC(C)CN(C)C(=O)COc1cc(Cl)c(Cc2ccc(O)c(C(C)C)c2)c(Cl)c1] | C |
| 121 | 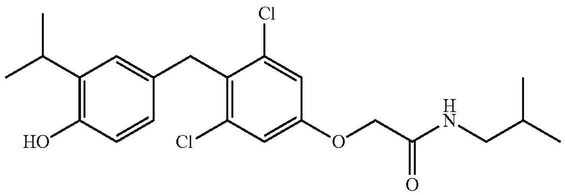 [SMILES: CC(C)CNC(=O)COc1cc(Cl)c(Cc2ccc(O)c(C(C)C)c2)c(Cl)c1] | C |

TABLE 1-continued
| Compound | Structure | ke |
|---|---|---|
| 122 | 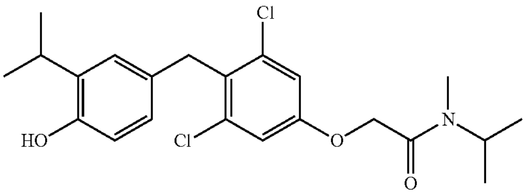 [SMILES: CC(C)c1cc(Cc2c(Cl)cc(OCC(=O)N(C)C(C)C)cc2Cl)ccc1O] | B |
| 123 | 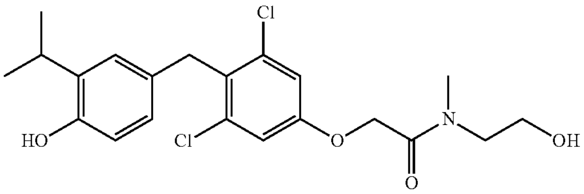 [SMILES: CC(C)c1cc(Cc2c(Cl)cc(OCC(=O)N(C)CCO)cc2Cl)ccc1O] | B |
| 124 | 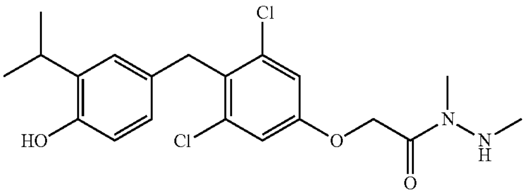 [SMILES: CNN(C)C(=O)COc1cc(Cl)c(Cc2ccc(O)c(C(C)C)c2)c(Cl)c1] | B |
| 125 | 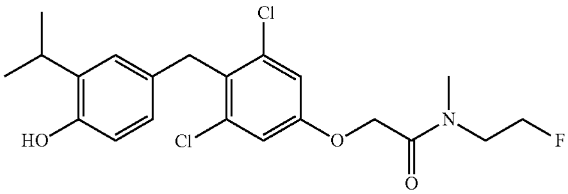 [SMILES: CC(C)c1cc(Cc2c(Cl)cc(OCC(=O)N(C)CCF)cc2Cl)ccc1O] | B |
| 126 | 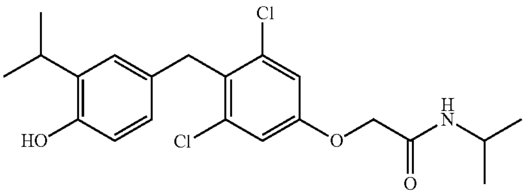 [SMILES: CC(C)NC(=O)COc1cc(Cl)c(Cc2ccc(O)c(C(C)C)c2)c(Cl)c1] | A |
| 127 | 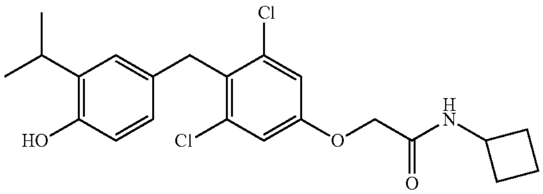 [SMILES: CC(C)c1cc(Cc2c(Cl)cc(OCC(=O)NC3CCC3)cc2Cl)ccc1O] | B |
| 128 | 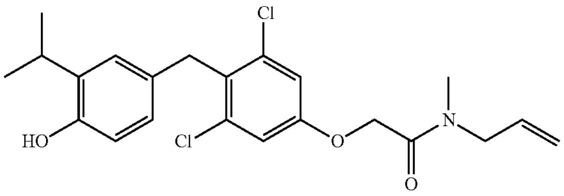 [SMILES: C=CCN(C)C(=O)COc1cc(Cl)c(Cc2ccc(O)c(C(C)C)c2)c(Cl)c1] | B |

TABLE 1-continued

| Compound | Structure | ke |
|---|---|---|
| 129 | 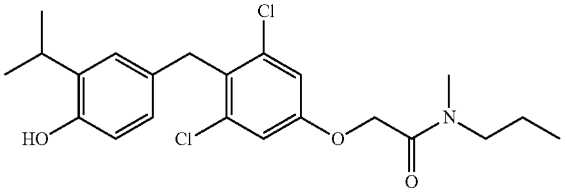 [SMILES: CCCN(C)C(=O)COc1cc(Cl)c(Cc2ccc(O)c(C(C)C)c2)c(Cl)c1] | B |
| 130 | 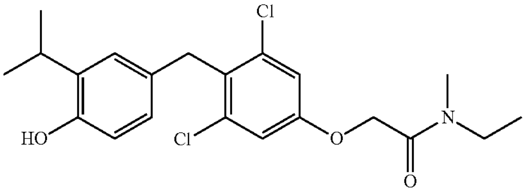 [SMILES: CCN(C)C(=O)COc1cc(Cl)c(Cc2ccc(O)c(C(C)C)c2)c(Cl)c1] | B |
| 131 | 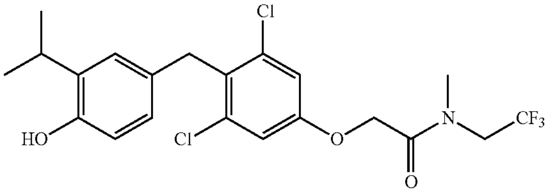 [SMILES: CC(C)c1cc(Cc2c(Cl)cc(OCC(=O)N(C)CC(F)(F)F)cc2Cl)ccc1O] | B |
| 132 | 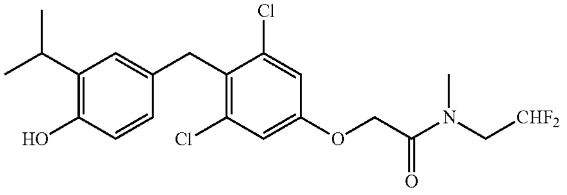 [SMILES: CC(C)c1cc(Cc2c(Cl)cc(OCC(=O)N(C)CC(F)F)cc2Cl)ccc1O] | B |
| 133 | 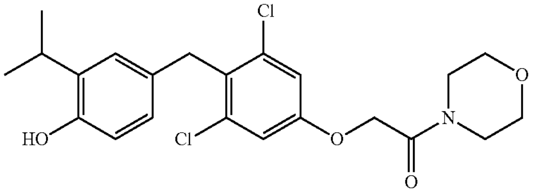 [SMILES: CC(C)c1cc(Cc2c(Cl)cc(OCC(=O)N3CCOCC3)cc2Cl)ccc1O] | A |

A = ke is more than or equal to 0.1;
B = ke is less than 0.1 and more than 0;
C = ke is 0;
NT = not tested.

Example 35: In Vitro Stability Evaluation in Mouse Plasma

Male CD-1 mouse plasma is purchased from BioIVT (catalog #MSE00PLK2YNN) and thawed in a 37° C. water bath with pH adjusted to 7.4 on Study day. After a pre-warm period of 15 minutes in a 37° C. water bath, 398 µL plasma is spiked with an aliquot of 2 µL stock solution of the test compound or positive control (propantheline) in dimethyl sulfoxide (DMSO) to achieve a final concentration of 1 µM with 0.5% DMSO. After a thorough mix, the mixture is placed back to the 37° C. water bath for incubations. At 0, 15, 30, 60, and 120 minutes, an aliquot of 30 µL reaction mixtures is removed and mixed with 300 µL acetonitrile containing 5 ng/mL terfenadine and 10 ng/mL tolbutamide as internal standards to quench the reaction. The resulting mixture is centrifuged at 4000 rpm, 4° C. for 15 minutes, and 100 µL supernatant is removed and mixed with 100 µL water for liquid chromatography-tandem mass spectrometry (LC-MS/MS) analysis.

LC-MS/MS Analysis

Shimadzu LC 30-AD HPLC system is used for sample analysis. The chromatography is performed on a reverse phase Kinetex 2.6 µm C18 column, 3.0×30 mm, 100 Å. The mobile phase A comprises of 0.1% formic acid in water and mobile phase B comprises of 0.1% formic acid in acetonitrile with a 2-min run time. The mass spectrometer (API-4000 and API Q Trap 4500 Applied Biosystems/MDS SCIEX Instruments, Framingham, MA, USA) is operated under electrospray ionization (ESI) positive or negative ion multiple reaction monitoring (MRM) mode.

Data Analysis

Percent compound remaining at a specific time point is calculated based on the peak area ratios at time 0 (as 100%). The observed rate constant ($k_{obs}$) for the metabolism of test compounds is calculated by plotting the natural log of percentage compound remaining versus time of incubation with the slope being $k_{obs}$. The half-life ($t_{1/2}$) is determined according to the following equation: $t_{1/2}=0.693/k_{obs}$.

Example 36: In Vivo Tissue Distribution Studies in Male CD-1 Mice

Male CD-1 mice (n=6 per group), 7-10 weeks old, are acclimated to the study room for a minimum of 3 days before dose administration in the studies. The test compounds are formulated in 1% N-methyl-2-pyrrolidone (NMP) and 1% Solutol in phosphate buffered saline (PBS) at 0.1 mg/mL clear solution and the dose volume was 10 mL/kg. The peripherally restricted FAAH inhibitor LL-650021 is formulated in 0.5% carboxymethyl cellulose in water at 0.1 mg/mL and the dose volume is 10 mL/kg. The concentrations of the formulation are determined to meet the acceptance criteria of within 20% of the target values.

The test compounds are administered to non-fasted mice at 1 mg/kg via subcutaneous (SC) injection or oral gavage (PO) with or without pretreatment of 1 mg/kg LL-650021 1 hour prior to test compound administration. At 1, 4, and 8 hours post-dose, the animals (n=2 per time point) are euthanized using $CO_2$ inhalation. A blood sample (0.3 mL) is collected from saphenous vein or other suitable site into pre-chilled $K_2$EDTA tube and placed on wet ice and brain and liver are harvested. The blood samples are centrifuged at 3200 g, 4° C. for 10 minutes and the plasma samples are transferred into polypropylene tubes, quick frozen over dry ice and kept at −60° C. or lower until analysis. The tissues are washed with cold saline, wiped dry, weighed, and then homogenized in 15 mM PBS (pH 7.4):methanol=2:1 buffer at the ratio of 1:10 (1 g tissue with 10 mL buffer resulting in 11-fold dilution). The tissue homogenates are kept at −60° C. or lower until analysis.

Sample Extraction

The plasma and tissue homogenates are extracted by protein precipitation. An aliquot of 10-50 μL plasma or 40-50 μL tissue homogenates is protein precipitated by adding 200-800 μL acetonitrile containing internal standards (10 ng/mL LL-120001 and 100 ng/mL of celecoxib, dexamethasone, glyburide, labetalol, tolbutamide, and verapamil), vortex-mixed for 10 min at 800 rpm and centrifuged at 4000 rpm, 4° C. for 15 minutes. The supernatant is transferred to the 96-well plate and centrifuged at 4000 rpm, 4° C. for 5 minutes before injected for LC-MS/MS analysis, or 200 μL supernatant is transferred to the 96-well plate, evaporated to dryness under a stream of nitrogen at 25° C., reconstituted with 50 μL of 70% acetonitrile, vortex-mixed for 10 min at 800 rpm and centrifuged at 4000 rpm, 4° C. for 5 minutes before injected for LC-MS/MS analysis.

LC-MS/MS Analysis

Acquity Ultra Performance LC system from Waters is used for sample analysis. The separations are performed on a ACQUITY UPLC BEH C18 column (50×2.10 mm; 1.7 m) at 50° C. with a flow rate of 0.6 mL/min. Mobile phase A consists of 2 mM ammonium acetate in methanol:water 5:95 and mobile phase B consists of 2 mM ammonium acetate in acetonitrile:water 95:5. Chromatography uses a linear gradient starting at 2% mobile phase B, 2% to 90% mobile phase B over 2.6 minutes, maintained at 90% B wash for 0.2 minutes, and a re-equilibration at 2% B for 0.2 minutes. An aliquot of 2-9 μL sample is injected. The mass spectrometer (API-6500+, Applied Biosystems/MDS SCIEX Instruments, Framingham, MA, USA) is operated under ESI in positive ion or negative ion MRM mode.

Example 37: In Vitro Prodrug and Agonist TRP Receptor Selectivity

LL-341070, a thyromimetic prodrug of Formula (I') described herein which delivers LL-341070A, a potent and selective small molecule agonist of thyroid hormone receptor (TR) beta following fatty acid amide hydrolase (FAAH)-mediated conversion, were evaluated for potency and selectivity for the thyroid hormone beta receptor (TRO). In vitro potency was determined via test compounds administered to luciferase-based TR reporter cell lines, using thyroid hormone (T3) as a positive control. Table 2 depicts the potency profiles of LL-341070 prodrug and LL-341070A active metabolite against TRO and TRα as measured in half maximal effective concentration (EC50), with selectivity measurement adjusted for the TRα-bias of T3 in the assays. Both LL-341070 and LL-341070A show enhanced selectivity for TRO, with LL-341070A showing enhanced potency.

TABLE 2

| Profile | Prodrug LL-341070 (nM) | Active L-341070A (nM) |
|---|---|---|
| TRβ $EC_{50}$ | 478 | 7.3 |
| TRα $EC_{50}$ | >10,000 | 24 |
| Selectivity* | n/a | 9.1 |

Example 38: LL-341070A Enhances Oligodendrocyte Progenitor Cell Differentiation In Vitro To profile LL-341070A, in vitro oligodendrocyte progenitor cell (OPC) assays were performed on primary OPC cultures generated from brains of E14.5 PLP-EGFP C57Bl/6 mouse embryos. Thyroid hormone (T3), known to induce OPC differentiation and remyelination, was used as a positive control at 10 ng/mL. Primary OPC cultures were treated with LL-341070A compound concentrations ranging from about 1 nM to about 1000 nM. After OPC differentiation was induced with or without LL-341070A compound for 5 days (N=6/concentration), cells were fixed and stained for myelin basic protein (MBP), normalized to total cell count.

FIG. 1 depicts the active metabolite of the LL-341070 prodrug, LL-341070A, enhanced oligodendrocyte differentiation in vitro in an oligodendrocyte progenitor cell assay (EC50=1.4 nM). Enhanced oligodendrocyte differentiation was shown to be relatively constant as a function of LL-341070A treatment concentration.

Example 39: Thyromimetic Treatment Enhances 24-OHC Synthesis In Vivo

Figure 2:
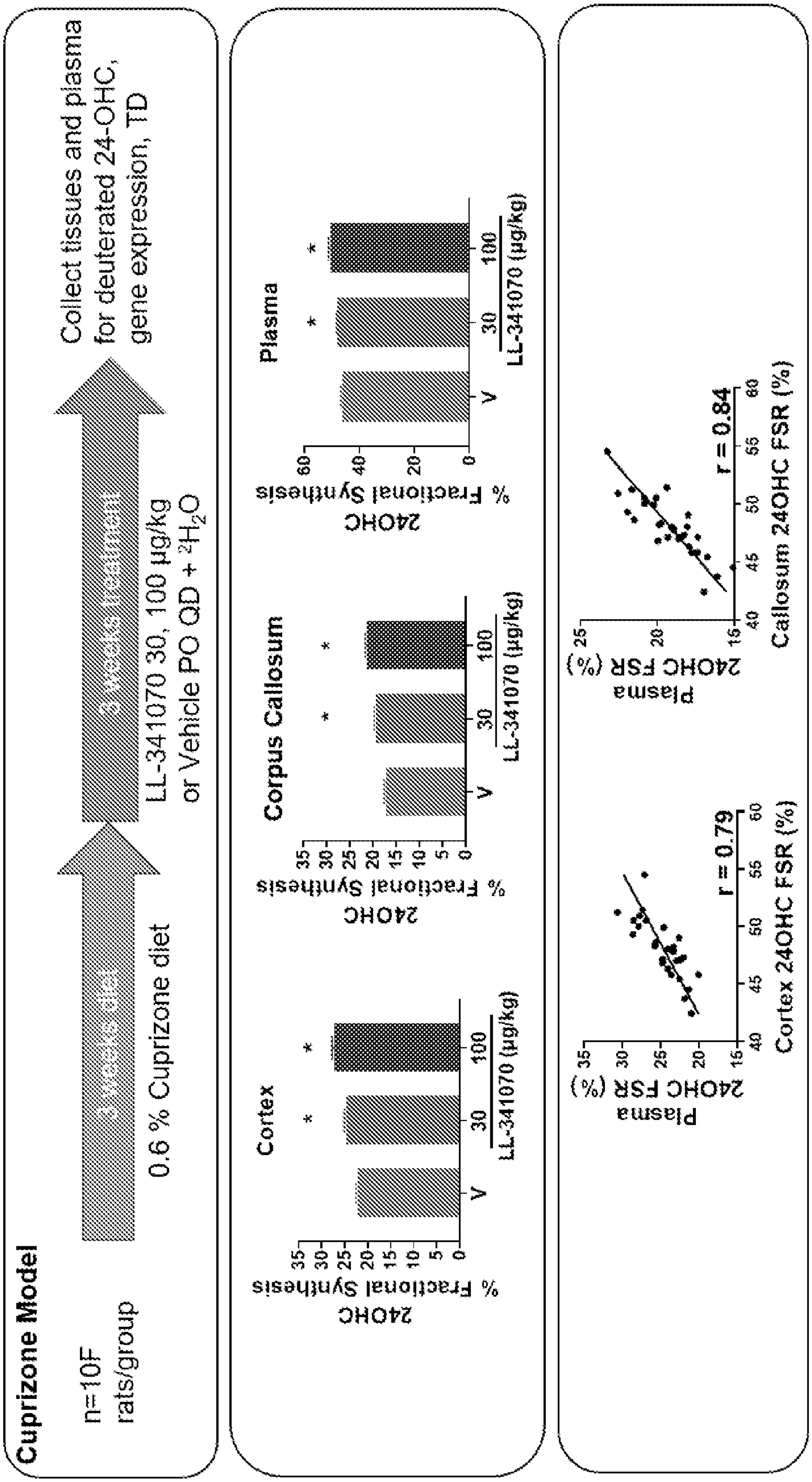
FIG. 2 depicts thyromimetic treatment enhances 24-OHC synthesis in vivo in the brains of rats following cuprizone-induced demyelination.

The ability of thyromimetics to accelerate the remyelination process in vivo was assessed by measuring the fractional synthesis of 24-hydroxycholesterol (24-OHC) in the brains of rats following cuprizone-induced demyelination. As shown in FIG. 2, the cuprizone demyelination model assessed n=10F rats/group. The effect of thyromimetic treatment on the fractional synthesis of 240HC was measured in brain and plasma using deuterated water labeling of 240HC in a cuprizone demyelination model following withdrawal from 0.6% cuprizone diet, during the period of active remyelination. At withdrawal from a 3 week 0.6% cuprizone diet, rats were provided deuterated water with administration of LL-341070 at 30 or 100 μg/kg for 3 weeks, then 24-OHC deuterium enrichment and labeling pattern were measured in cortex and corpus callosum. LL-341070 induced a dose-dependent increase in deuterated 24-OHC compared to vehicle controls, suggesting an increased rate of myelin synthesis. As shown in FIG. 2, thyromimetic treatment enhances the fractional synthesis rate (FSR) of 24S-hydroxycholesterol in brain and demonstrates a strong correlation with 240HC FSR in plasma. 240HC Fractional Synthesis Rate (FSR) was calculated based on data collected from tissue and plasma underwent alkaline hydrolysis and derivatization for GC/MS or LC/MS analysis of deuterated 240HC. Plasma analysis of 240HC measured by LC/MS as fraction of labeled to total plasma 240HC by Ardena Biosciences. Fractional synthesis was calculated by Mass Isotopomer Distribution Analysis using precursor 2H enrichment in body water from liver palmitate 6. Statistics: Data were analyzed by one-way ANOVA with Tukey's multiple comparisons test and are represented as mean+/−SEM. *p<0.05.

Compound potency, pharmacokinetics and target engagement were confirmed for LL-341070 prior to testing efficacy in remyelination models, including oligodendrocyte precursor cell differentiation in vitro and experimental autoimmune encephalitis in vivo.

Figure 3:
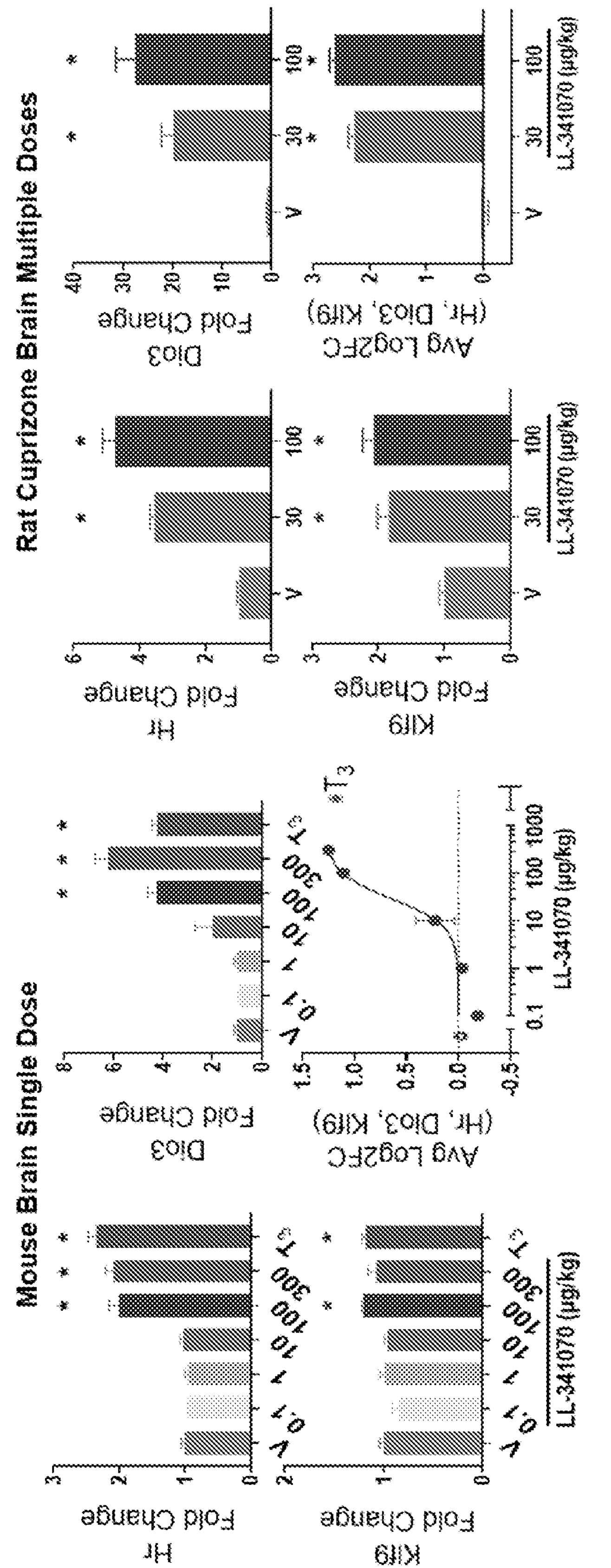
FIG. 3 depicts TRβ target engagement in brain is demonstrated by increased expression of T3-responsive target genes in vivo.

Example 40: Engagement of TRP in Brain Increases Expression of T3-Target Genes In Vivo FIG. 3 depicts TRβ target engagement in brain is demonstrated by increased expression of T3-responsive target genes in vivo. Single PO administration of LL-341070 (ranging from about 0.1 μg/kg to about 300 μg/kg) or T3 (about 300 μg/kg) in male C57BL/6 mouse increases expression of Hr, Dio3, Klf9 (quantified by QuaniPlex) and composite average log 2 fold change in brain. Klf9, a T3-responsive gene linked to myelin regeneration in vitro, is upregulated at various treatment concentrations. This expression increase was confirmed in the brain of a rat cuprizone model (as previously discussed) with 21 day repeat administration of LL-341070 at 30 μg/kg or 100 μg/kg, or T3 dosed at 300 μg/kg (quantified by Nanostring). Interestingly, Dio3 has an enhanced expression increase with repeat dosing.

Figure 4:
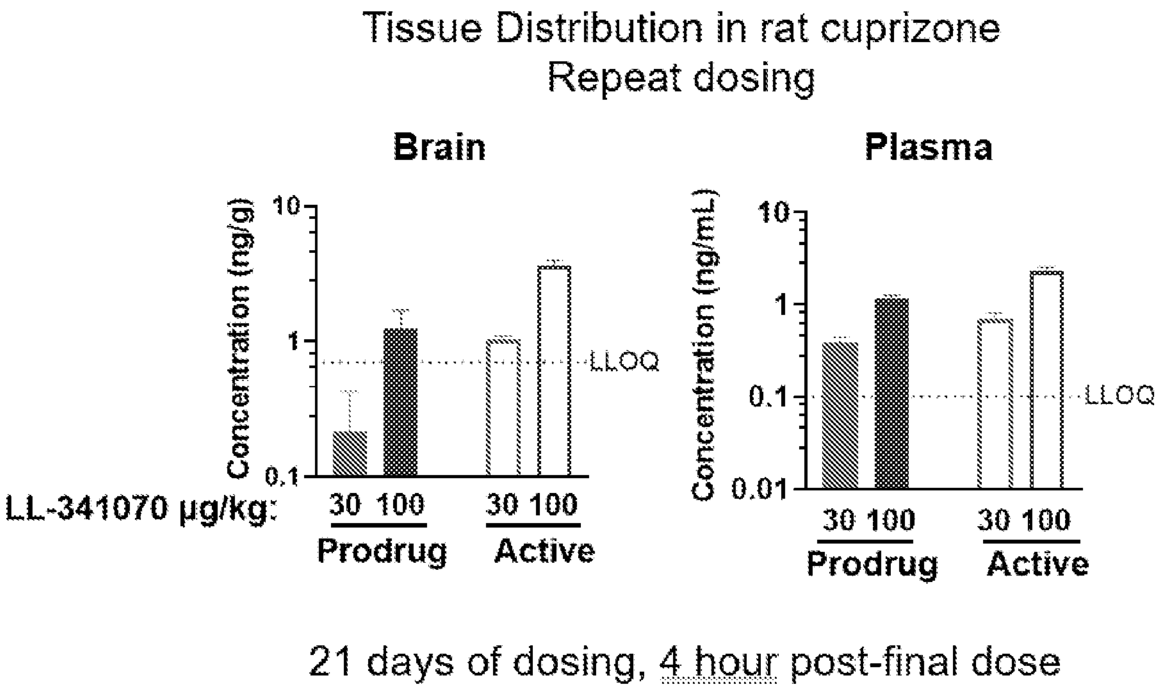
FIG. 4 depicts brain and plasma concentration following 21 days of repeat administration of LL-341070 measured 4 hours post-final dose.

Example 41: In Vivo Tissue Distribution Demonstrates Enhanced Brain Exposure of Active Compound Compared to Prodrug In vivo brain exposure of active compound compared to prodrug was assessed via tissue distribution (TD) assay in mouse and rat cuprizone model, measured as brain exposure ratio of brain to plasma following thyromimetic treatment. As shown in Table 3, single PO administration of LL-341070 (100 μg/kg) or LL-341070A(100 μg/kg), in male C57BL/6 mouse measured in brain and plasma, demonstrates enhanced brain exposure of active compound LL-341070A compared to prodrug LL-341070, leading to a brain-to-plasma AUC ratio >1 for LL-341070A, wherein AUC is 0-24 hr. Data shows AUC of LL-341070A in brain is ~7-fold higher than prodrug LL-341070. Table 3 also depicts brain-to-plasma AUC ratio. As shown in FIG. 4, 21 days of repeat administration of LL-341070 (30 μg/kg or 100 μg/kg) or LL-341070A(30 μg/kg or 100 μg/kg), in rat cuprizone model measured in brain and plasma 4 hours post-final dose, demonstrates enhanced brain exposure of active compound LL-341070A compared to prodrug LL-341070.

TABLE 3

| Prodrug @ 100 μg/kg PO | Brain AUC (ng/ml*h) | Plasma AUC (ng/mL*h) | Brain/Plasma AUC Ratio |
|---|---|---|---|
| Prodrug LL-341070 | 10.9 | 18.8 | 0.58 |
| Active LL-341070A | 73.9 | 35.8 | 2.06 |

Figure 5:
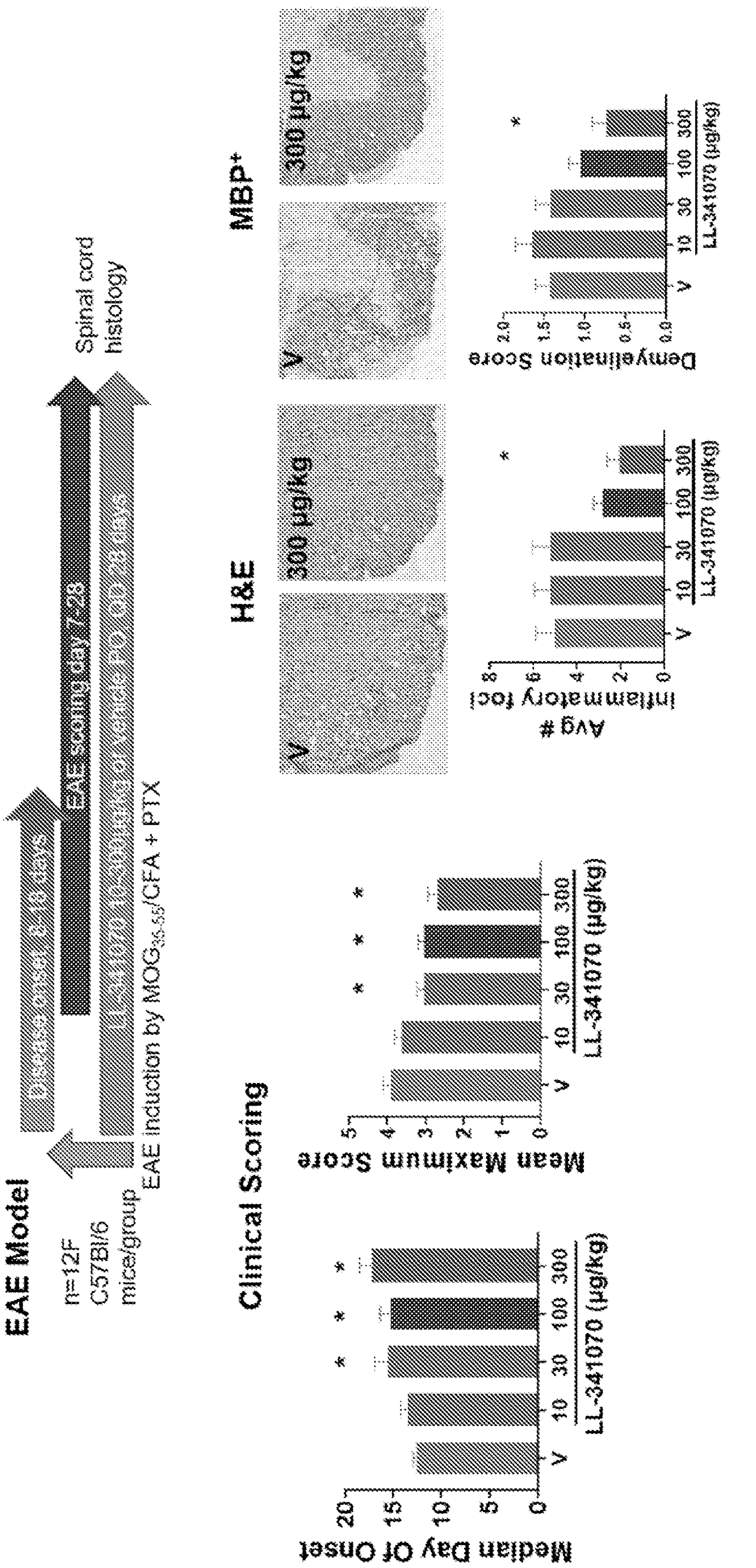
FIG. 5 depicts LL-341070 improves in vivo clinical scoring and histology in mouse prophylactic experimental autoimmune encephalitis (EAE) model.

Example 42: LL-341070 Improves In Vivo Clinical Scoring and Histology in Mouse EAE Model As shown in FIG. 5, LL-341070 efficacy was assessed in a mouse prophylactic experimental autoimmune encephalitis (EAE) model wherein following EAE induction by MOG35-55/CFA+PTX, disease onset 8-18 days after induction, with EAE scoring on day 7-28 after induction. The EAE model assessed n=12F C57Bl/6 mice/group, administered LL-341070 (10 μg/kg to 100 μg/kg) or vehicle PO daily after EAE induction. LL-341070 administered daily in a prophylactic paradigm dose-dependently improved median day of disease onset and decreased maximum disease severity. Histological analysis of spinal cord 28 days after immunization demonstrated a reduction of inflammatory foci, apoptotic cell count, and reduced area of demyelination by H&E and MBP staining. LL-341070 improves the clinical scoring mean and histological endpoints of inflammation and demyelination in a mouse EAE model.

Clinical scores were determined by blinded observer. Histology analyzed in spinal cord sample (demyelination score assessed by % demyelinated area in anti-MBP stain, inflammatory foci refers to # of groups of >20 cells/section in H&E stain). Statistics: Median day of onset in EAE compared using Wilcoxon's survival test.

Example 43: FAAH Expression is Enriched in Brain

Figure 6:
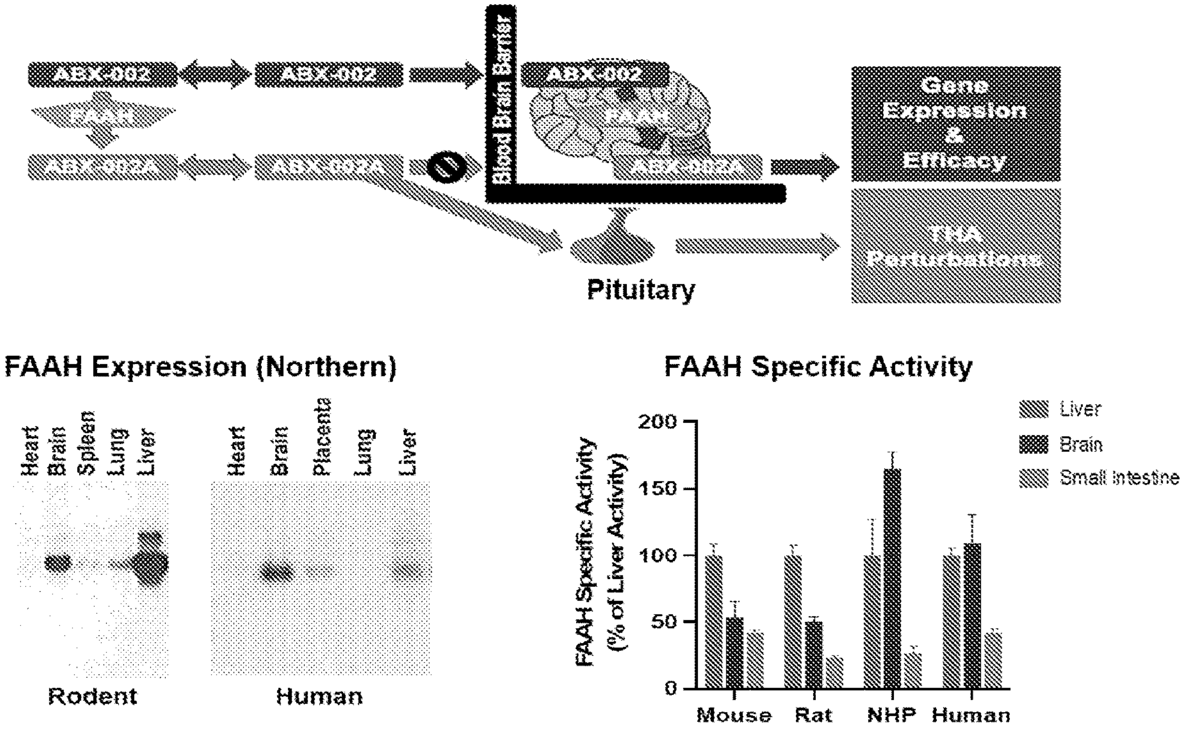
FIG. 6 depicts FAAH expression and specific activity across species and tissue types.

As shown in FIG. 6, brain-directed thyromimetic prodrugs (such as ABX-002 which is Compound 1 described herein, activated to ABX-002A) that are activated by fatty acid amide hydrolase (FAAH) were utilized to elucidate mechanisms by which thyromimetics disrupt the thyroid hormone axis (THA). The delivery of potent thyromimetics was altered to help identify whether feedback control on THA derives from central (hypothalamic) or peripheral (pituitary) mechanisms and potentially enhance therapeutic index of thyromimetics. These studies were performed using recombinant FAAH, tissue-derived S9 fractions, in vivo tissue distribution (TD), gene expression in brain and liver, and effects on $T_4$ in mice as a marker of THA disruption. Northern blot assay confirmed FAAH expressed across species (rodent and human), with relative mRNA FAAH expression enhanced in the brain. FAAH specific activity (cleavage of AMC assay) from tissue-derived S9 fractions of different organs (liver, brain, small intestine) across species (mouse, rat, non-human primate, human), calculated as a percentage of liver activity, was shown to be increased in brain of human and non-human primate.

Example 44: FAAH Expression Enhances Delivery of ABX-002A to Brain

Figure 7:
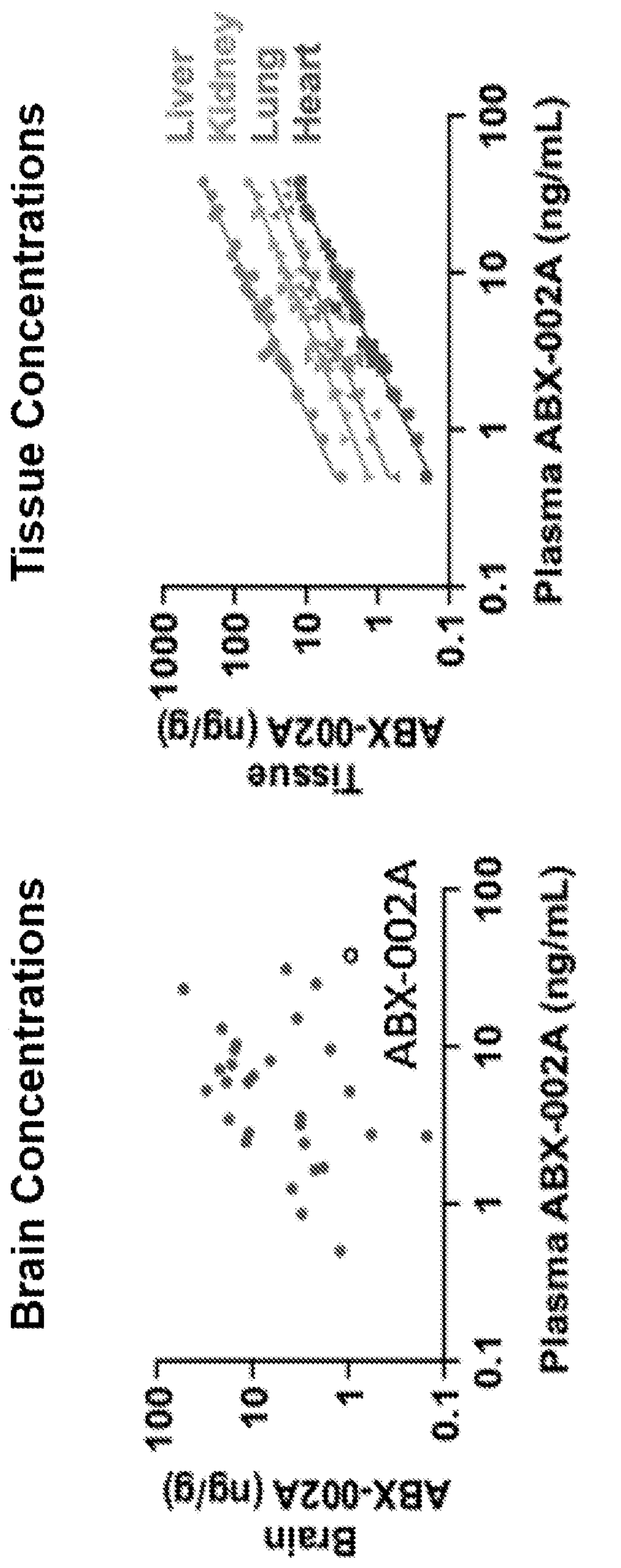
FIG. 7 depicts concentrations of ABX-002A in brain, liver, kidney, lung, and heart were measured 1 hour after SC administration of 30 different prodrugs of ABX-002A.

To assess delivery, concentrations of ABX-002A in brain, liver, kidney, lung, and heart were measured 1 hour after SC administration of 30 different prodrugs of ABX-002A. As shown in FIG. 7, brain-to-plasma ratios were increased relative to ABX-002A for the prodrugs, while tissue-to-plasma ratios for peripheral organs (liver, kidney, lung, and heart) showed a linear (constant) tissue-to-plasma relationship. Data shows FAAH is highly expressed in the CNS and ABX prodrugs enhance delivery of active metabolite to the brain by >30× with brain-to-plasma ratios >1. In organs other than the brain, data shows tissue concentrations are driven by plasma concentrations of the active metabolite ABX-002A.

Example 45: Global and Peripheral FAAH Inhibitors Alter Metabolite Distribution in Mice The ability of globally-penetrant and peripherally-restricted FAAH inhibitors (GFI & PFI, respectively) to alter distribution of ABX-002 and ABX-002A was assessed. Table 4 depicts the potency profiles (measured in apparent $IC_{50}$s (nM)) of peripheral and global FAAH inhibitors: LL-650177 (PFI), URB9373 (PFI), and PF-044578454 (GFI) obtained after 30 min preincubation with recombinant human FAAH and 7-amino-4-methylcourmarin (AMC).

TABLE 4

| FAAH inhibitor | Apparent $IC_{50}$s (nM) | Distribution |
|---|---|---|
| LL-650177 | 9.1 | Peripheral |
| URB937 | 69 | Peripheral |
| PF-04457845 | 3.0 | Global |

Figure 8:
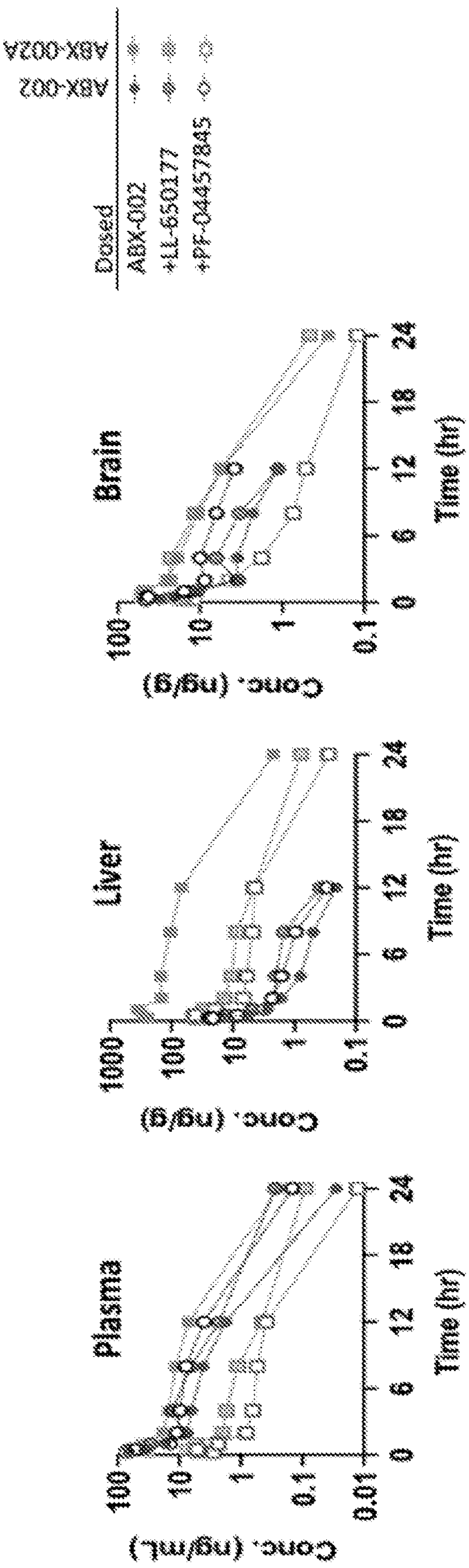
FIG. 8 depicts plasma, liver, and brain concentrations following ABX-002 prodrug treatment with or without peripheral or global FAAH inhibitors.

FIG. 8 shows plasma, liver, and brain concentrations after co-dosing prodrug (ABX-002) with or without PFI or GFI. Prodrug levels did not change or slightly increased with FAAH inhibition. Active metabolite (ABX-002A) levels decreased in plasma & liver with PFI & in all organs with GFI. Table 5 depicts the inhibition of active metabolite (LL-650177 or PF-044578454) in AUC in the plasma, liver, and brain after prodrug (ABX-002) co-dosing. Tissue distribution studies in mice confirm global & peripheral inhibition of FAAH.

TABLE 5

| FAAH inhibitor | Plasma | Liver | Brain |
|---|---|---|---|
| LL-650177 | 89% | 91% | −12% |
| PF-04457845 | 94% | 94% | 83% |

Example 46: Induction of T3-Regulated Genes in View of Prodrug and FAAH Inhibitors Female C57BL/6 mice (n=5/group), 6-8 weeks old, were acclimated to the study room for at least 3 days before dose administration in the studies. Non-fasted mice were given a single dose of PFI or vehicle orally (PO) on Day 0 at time=−1 hour. Single dose administered at 5 mL/kg based on most recent body weight, collected once for the duration of the study. Following the PFI or vehicle dose, animals were given a single dose of test article at time=0 hour. One group (n=5) was PO administered 300 ug/kg of T3 only at time=0 hours. Approximately 4 hours post test article dose (t=4 hours), animals were humanely euthanized and brain, liver, heart, pituitary, spinal cord, and plasma samples were harvested.

Sample Processing a. Expression Analysis Samples—At endpoint, multiple organs were harvested and tissues processed immediately as described below.

i. Brain: For each mouse, the cranium was opened and the brain removed. The cerebellum was sectioned away and the cerebral cortex was hemisected sagittally and the left half collected. After rinsing extraneous blood from the tissue with ice cold 0.9% NaCl, the cerebral cortical specimen was placed into a tube containing 1.2 mL pre-chilled RNALater and stored at 4° C.

ii. Liver: For each mouse, one liver biopsy (100-150 mg) was collected from the left lateral liver lobe. After rinsing extraneous blood from the biopsy with ice cold 0.9% NaCl, the sample was placed into 1.2 mL pre-chilled RNALater and stored at 4° C. iii. Left Ventricle: For each mouse, the left ventricle (LV) blood cleared using PBIs standard methods, and half of LV free wall was collected. After rinsing extraneous blood from the tissue with ice cold 0.9% NaCl, the LV free wall was placed into 1.2 mL pre-chilled RNALater and stored at 4° C. LV tissue was retained at PBI for potential future analyses or until appropriate genes can be identified for up to 6 months following conclusion of the in-life phase of study. Sample disposition was confirmed prior to disposal.

iv. Pituitary Gland: For each mouse, after removing the brain the pituitary gland was harvested. After rinsing extraneous blood from the pituitary with ice cold 0.9% NaCl, the specimen was placed into 0.15 mL pre-chilled RNALater and stored at 4° C. Pituitary tissue was retained at PBI for potential future analyses or until appropriate genes can be identified for up to 6 months following conclusion of the in-life phase of study. Sample disposition was confirmed prior to disposal.

b. Pharmacokinetic Samples—At endpoint, blood and tissue specimens were processed immediately as described below. Samples for PK analysis were retained at PBI at −80° C. for up to 90 days following conclusion of the in-life phase of study.

i. Plasma: whole blood (~300 μL) was collected on K3EDTA via cardiac puncture under isoflurane anesthesia. Blood was immediately placed on wet ice. Following the conclusion of takedown procedures, blood was centrifuged at 4° C. for 10 minutes at 10,000×g. Plasma (~125 μL) was aliquoted to appropriately labelled tubes and flash frozen.

ii. Liver: For each mouse, one liver biopsy (30-50 mg) was collected from the left lateral liver lobe. After rinsing extraneous blood from the biopsy with ice cold 0.9% NaCl, the sample was placed into an appropriately labelled tube and flash-frozen in liquid nitrogen.

iii. Brain: For each mouse, a mid-brain biopsy (30-50 mg) was collected from the right cerebral cortex. After rinsing extraneous blood from the tissue with ice cold 0.9% NaCl, the biopsy was placed into an appropriately labelled tube and flash frozen.

iv. Left Ventricle: For each mouse, the left ventricle (LV) will have blood cleared using PBIs standard methods, and half LV free wall was collected. After rinsing extraneous blood from the tissue with ice cold 0.9% NaCl, the LV free wall was placed into an appropriately labelled tube and flash frozen.

Target Engagement

Changes in the expression of select genes identified through transcriptomic analysis were measured from purified RNA using a hybridization-based in situ RNA quantification method (NanoString, Seattle, WA). Briefly, fresh tissues were collected in RNALater™ Stabilization Solution, catalog #AM7021 (ThermoFisher Scientific; Carlsbad, CA) and frozen at −20° C. until ready for RNA extraction. Whole blood was collected in MiniCollect K2EDTA tubes, catalog #450480 Greinder Bio-one GmbH (Kremsmunster, Austria), via terminal cardiac puncture and processed to plasma by centrifuging at 2000×g for 10 minutes at 4° C. For RNA extraction, tissues were homogenized using a bead homogenizer in TRIzol Reagent, catalog #15596026 (ThermoFisher Scientific), and RNA was extracted according to manufacturer's protocols and purified using Econospin RNA Mini Spin Columns for RNA (Ephoch Life Sciences, Missouri City, TX, catalog #1940-250) following manufacturer's protocols. Specific gene probes were designed by NanoString Bioinformatics Team using an identified target sequence based on the NCBI Reference Sequence (RefSeq) database. Custom probes were synthesized by Integrated DNA Technologies (IDT; Coralville, IA). mRNA expression was analyzed on an nCounter® SPRINT Profiler NanoString system using a multiplexing approach with nCounter PlexSet-12 Reagent Pack, catalog #PS-GX-PTK-12 (CSO) according to manufacturer's protocols (NanoString, Inc, Seattle, WA).

Data Analysis

Figure 9C:
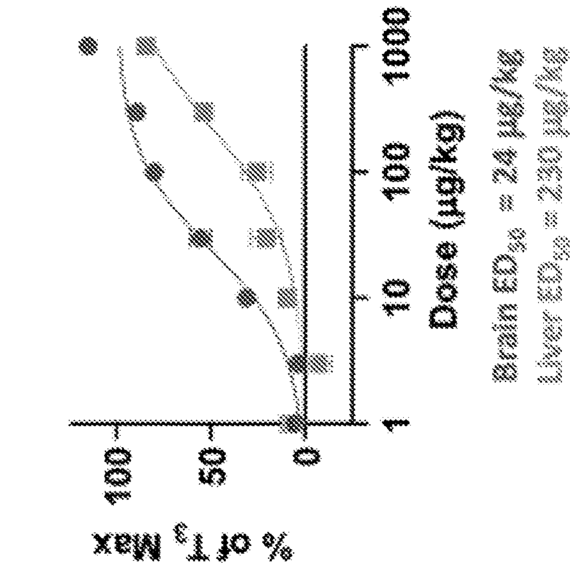
FIG. 9C depicts induction of T3-target genes in brain vs. liver after single administration of ABX-002 plus FAAH inhibitor.
Figure 9B:
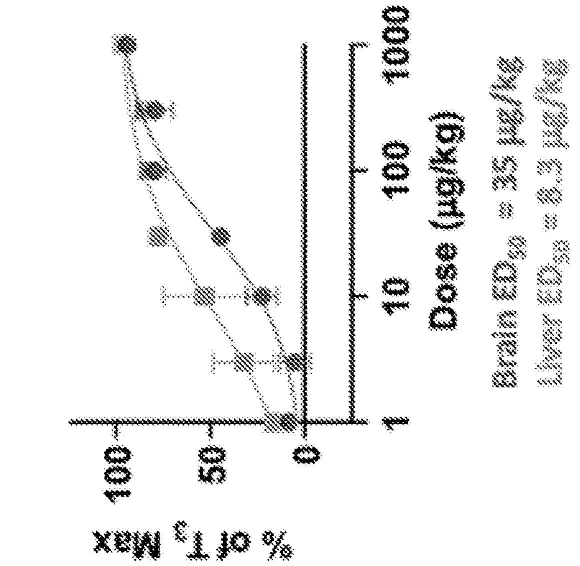
FIG. 9B depicts induction of T3-target genes in brain vs. liver after single administration of ABX-002.
Figure 9A:
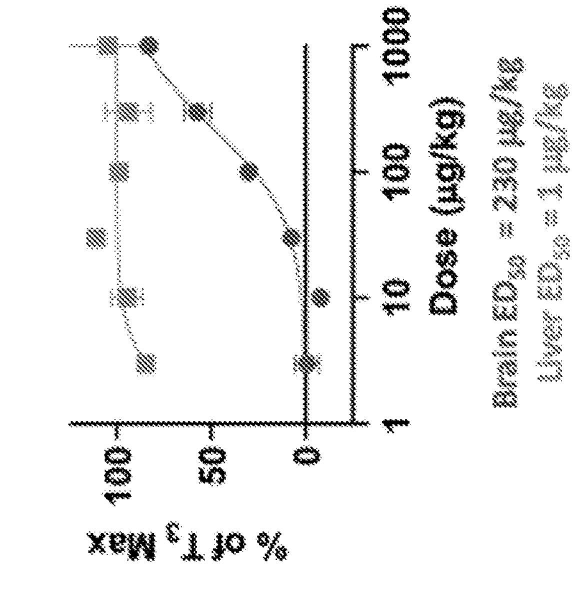
FIG. 9A depicts induction of T3-target genes in brain vs. liver after single administration of ABX-002A.
Figures 10A, 10B, 10C, 10D:
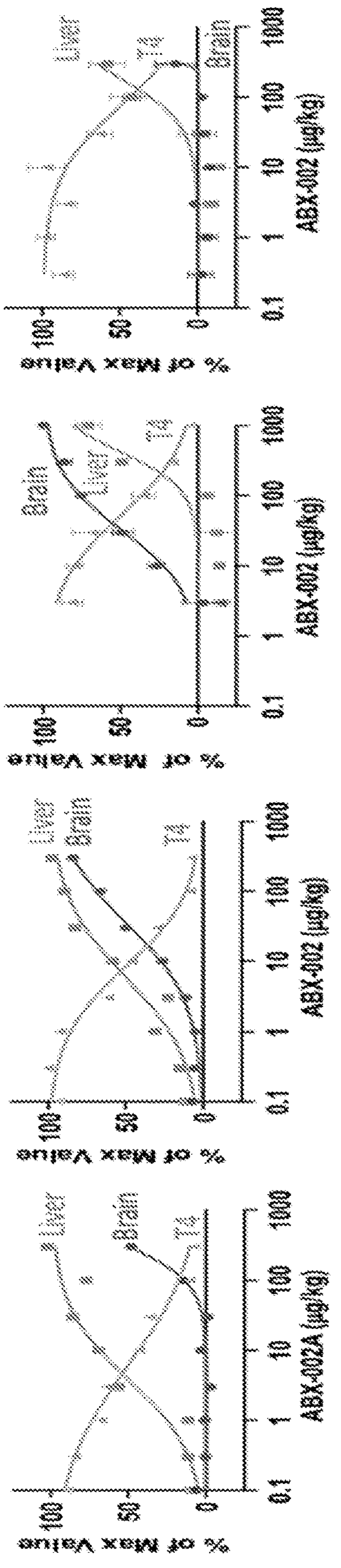
FIG. 10A depicts gene expression in brain and liver, and effects on T4 after administration of ABX-002A.
FIG. 10B depicts gene expression in brain and liver, and effects on T4 after administration of ABX-002.
FIG. 10C depicts gene expression in brain and liver, and effects on T4 after administration of ABX-002 plus peripheral FAAH inhibitor.
FIG. 10D depicts gene expression in brain and liver, and effects on T4 after administration of ABX-002 plus global FAAH inhibitor.

T3-target genes are increased after a single administration of drug with the relative activity in brain vs. liver determined by prodrug and/or FAAH inhibition. Relative activity in brain vs. liver (as a marker of peripheral activity) shifts >1500-fold across the different dosing paradigms. FIGS. 9A, 9B, and 9C show induction of T3-regulated genes in brain (blue) & liver (orange) 4 h after single administration of (A) active metabolite or (B) prodrug alone or (C) prodrug+PFI (URB937). RNA analyzed by Nanostring; Mean fold change of multiple genes was calculated on a log 2 scale and normalized to data obtained for 300 mg/kg of T3. PFI administration reduced potency of prodrugs on activation of $T_3$-regulated genes in the liver by >10×, without affecting activity or exposure in the brain. PFIs also decreased potency on the THA, consistent with negative feedback based on circulating peripheral metabolite rather than brain exposure. Thus, use of a PFI allowed separation of on-target brain effects from those on THA.

Example 47: T4 Parallels Peripheral Activity

Female C57BL/6 mice (n=5/group), 6-8 weeks old, were acclimated to the study room for at least 3 days before dose administration in the studies. Mice were dosed at 5 mL/kg based on most recent body weight, collected once for the duration of the study. Based on most recent body weight, collected once for the duration of the study, mice were placed into weight-matched treatment dosing cohorts. Mice were given a single administration of PFI or vehicle orally (PO) daily (n=5/group) for 7 days at time=−1 hour. Following the PFI (100 μg/kg) or vehicle dose (10 mL/kg, p.o.), animals were given test article daily at time=0 hour. Test article administration one of eight dose levels (0.1, 0.3, 1, 3, 10, 30, 100 or 300 μg/kg) on Days 1-7 for a total of seven doses. Mice were dosed PO, QD for 7 days with (A) active metabolite or (B) prodrug alone; (C) prodrug+PFI (LL-650177) or (D) prodrug+GFI. Approximately 4 or 8 hours post test article dose (t=4 hours or t=8 hours), animals were humanely euthanized using standard procedures, and brain, liver, and plasma samples were harvested. RNA from samples harvested 4 hours after final dose was quantified using a hybridization-based in situ RNA quantification method (NanoString, Seattle, WA), as described below. RNA from samples harvested 8 hours after final dose was quantified using a hybridization-based in situ RNA quantification method (QuantiGene Plex), as described below. On the final day of dosing, mice were dosed on a timetable to mitigate the influence of diurnal effects on thyroid hormone sensitive gene expression. Thus, treatment groups were balanced for "time of day" at endpoint sacrifice. Mice were anesthetized 4 or 8 hours after final dosing, have blood collected via retro-orbital puncture, and euthanized using standard procedures. Immediately following euthanasia, tissues were harvested and processed per the following procedures.

Sample Processing a. Expression Analysis Samples—At endpoint, multiple organs were harvested and tissues processed immediately as described below.

i. Brain: For each mouse, the cranium was opened and the brain removed. The cerebellum was sectioned away and the cerebral cortex was hemisected sagittally and the left half collected. After rinsing extraneous blood from the tissue with ice cold 0.9% NaCl, the cerebral cortical specimen was placed into a tube containing 1.2 mL pre-chilled RNALater and stored at 4° C.

ii. Liver: For each mouse, one liver biopsy (100-150 mg) was collected from the left lateral liver lobe. After rinsing extraneous blood from the biopsy with ice cold 0.9% NaCl, the sample was placed into 1.2 mL pre-chilled RNALater and stored at 4° C. iii. Left Ventricle: For each mouse, the left ventricle (LV) blood cleared using PBIs standard methods, and half of LV free wall was collected. After rinsing extraneous blood from the tissue with ice cold 0.9% NaCl, the LV free wall was placed into 1.2 mL pre-chilled RNALater and stored at 4° C. LV tissue was retained at PBI for potential future analyses or until appropriate genes can be identified for up to 6 months following conclusion of the in-life phase of study. Sample disposition was confirmed prior to disposal.

iv. Pituitary Gland: For each mouse, after removing the brain the pituitary gland was harvested. After rinsing extraneous blood from the pituitary with ice cold 0.9% NaCl, the specimen was placed into 0.15 mL pre-chilled RNALater and stored at 4° C. Pituitary tissue was retained at PBI for potential future analyses or until appropriate genes can be identified for up to 6 months following conclusion of the in-life phase of study. Sample disposition was confirmed prior to disposal.

b. Pharmacokinetic Samples—At endpoint, blood and tissue specimens were processed immediately as described below. Samples for PK analysis were retained at PBI at −80° C. for up to 90 days following conclusion of the in-life phase of study.

i. Plasma: whole blood (~300 μL) was collected on K3EDTA via cardiac puncture under isoflurane anesthesia. Blood was immediately placed on wet ice. Following the conclusion of takedown procedures, blood was centrifuged at 4° C. for 10 minutes at 10,000×g. Plasma (~125 μL) was aliquoted to appropriately labelled tubes and flash frozen.

ii. Liver: For each mouse, one liver biopsy (30-50 mg) was collected from the left lateral liver lobe. After rinsing extraneous blood from the biopsy with ice cold 0.9% NaCl, the sample was placed into an appropriately labelled tube and flash-frozen in liquid nitrogen.

iii. Brain: For each mouse, a mid-brain biopsy (30-50 mg) was collected from the right cerebral cortex. After rinsing extraneous blood from the tissue with ice cold 0.9% NaCl, the biopsy was placed into an appropriately labelled tube and flash frozen.

iv. Left Ventricle: For each mouse, the left ventricle (LV) will have blood cleared using PBIs standard methods, and half LV free wall was collected. After rinsing extraneous blood from the tissue with ice cold 0.9% NaCl, the LV free wall was placed into an appropriately labelled tube and flash frozen.

Target Engagement

Tissue samples were prepared for biochemical analysis by cryopowdering on liquid nitrogen, and lysed using PBI's standard methods. Changes in the expression of select genes identified through transcriptomic analysis (mRNA expression) were measured from purified RNA using a hybridization-based in situ RNA quantification method (NanoString or QuantiGene Plex). Target gene expression data was presented as a ratio to the geometric mean of appropriately expressed normalization genes. Briefly, fresh tissues were collected in RNALater™ Stabilization Solution, catalog #AM7021 (ThermoFisher Scientific; Carlsbad, CA) and frozen at −20° C. until ready for RNA extraction. Whole blood was collected in MiniCollect K2EDTA tubes, catalog #450480 Greinder Bio-one GmbH (Kremsmunster, Austria), via terminal cardiac puncture and processed to plasma by centrifuging at 2000×g for 10 minutes at 4° C. For RNA extraction, tissues were homogenized using a bead homogenizer in TRIzol Reagent, catalog #15596026 (ThermoFisher Scientific), and RNA was extracted according to manufacturer's protocols and purified using Econospin RNA Mini Spin/Columns for RNA (Ephoch Life Sciences, Missouri City, TX, catalog #1940-250) following manufacturer's protocols. Specific gene probes were designed by NanoString Bioinformatics Team using an identified target sequence based on the NCBI Reference Sequence (RefSeq) database. contains. Custom probes were synthesized by Integrated DNA Technologies (IDT; Coralville, IA). mRNA expression was analyzed on an nCounter® SPRINT Profiler NanoString system using a multiplexing approach with nCounter PlexSet-12 Reagent Pack, catalog #PS-GX-PTK-12 (CSO) according to manufacturer's protocols (NanoString, Inc, Seattle, WA).

T4 Analysis

T4 was measured in terminal plasma samples using an ELISA kit (Biovision, Inc., Thyroxine [T4] [Mouse/Rat] ELISA Kit, Cat #: K7421-100). Assays were performed according to manufacturer's instructions with minor modifications based on previous assay validation efforts. Briefly, a seven-point standard curve of provided T4 diluted in Assay Buffer (25, 15, 10, 5, 2, 1 μg/dL) was prepared in duplicate for each assay. Plasma samples (undiluted), blanks (Assay Buffer) and standards were added to separate wells of a 96-well plate pre-coated with a T4 capture antibody, followed by addition of T4 Enzyme Conjugate to each well. Plates were then gently shaken (600 rpm) for 20-30 s to mix, and then covered with an acetate plate seal and incubated for 1 h at room temperature (RT) with gentle shaking (600 rpm). Plate contents were aspirated and washed three times with 1× Wash Buffer, then blotted on paper towels to remove excess liquid. TMB Substrate was then added to each well and plates were secured with an acetate seal incubated for 15 min at RT, protected from light. Stop Solution was then added to each well and the plates shaken gently to mix the solution. Absorbance was read at 450 nm within 15 min of addition of the Stop Solution using a Varioskan Lux plate reader (ThermoFisher Scientific, Carlsbad, CA). Relative optical densities (ODs) were background-corrected against blank samples and standard curves. T4 concentrations were interpolated using the four-parameter curve-fit method. Unknown sample concentrations were determined using GraphPad Prism software (GraphPad Prism 9.0.2, GraphPad Software, San Diego, CA).

Data Analysis

FIGS. 10A, 10B, 10C and 10D show gene expression in brain (blue) & liver (orange), & effects on T4 (gray) 4 or 8 h after last dose in mice that had been dosed PO, QD for 7 days with (A) active metabolite or (B) prodrug alone; (C) prodrug+PFI (LL-650177) or (D) prodrug+GFI. Both prodrug and active metabolite reduce T4 levels after 7 days of treatment. Table 6 reports $ED_{50}$ values in μg/kg for each treatment type.

TABLE 6

| Treatment | Brain ($ED_{50}$ mg/kg) | Liver ($ED_{50}$ mg/kg) | $T_4$ ($ED_{50}$ mg/kg) |
|---|---|---|---|
| ABX-002A | 310 | 3.8 | 6.0 |
| ABX-002 (n = 3) | 44 | 2.5 | 3.4 |
| +LL-650177 | 30 | 260 | 48 |
| +PF-04457845 | >300 | 124 | 89 |

Using $T_4$ as a marker for effects on THA; $T_4$ parallels peripheral activity more than CNS activation of target genes. Negative regulation of $T_4$ by thyromimetics does not appear to be predominantly centrally-mediated because the effects on THA and liver gene expression parallel plasma distribution more closely than exposure or activity in the CNS, suggesting a primarily pituitary-driven effect. The combination of a thyromimetic prodrug and a PFI may further enhance delivery of thyromimetics to the brain and maximize centrally-targeted distribution.

Example 48: Peripheral Exposure to ABX-002A Predicts Effects on THA

The relationship between THA effects and plasma ABX-002A was studied in both mice and NHP. Mouse: Female C57BL/6 mouse data from Example 14 above was employed to calculate exposure to amide and acid based on PK data from an independent experiment such as that detailed in Example 12. PK was only performed at a single dose, with other doses calculated proportionately. Non-human primate (NHP): Plasma pharmacokinetics and effects on the thyroid hormone axis were measured in non-naïve cynomolgus monkeys (n=3/group) after daily dosing of ABX-002 at 10, 30, 100 or 300 ug/kg for 7 days. ABX-002 was formulated in 0.1% NMP/0.1% solutol and administered at 5 mL/kg PO. Blood samples were taken on day 1 and day 7 at 0, 0.25, 0.5, 1, 2, 4, 8, 12, and 24 hrs and analyzed for ABX-002, LL-340001, T3 and T4 levels by LCMS (as described above). TSH was measured by immunoassay.

Bioanalysis for T3 and T4 in NHP serum was performed using a surrogate matrix, QCs, double blank and blank. Standard curve samples were prepared by adding 5 μL of WS to 50 μL blank surrogate serum. QC samples were prepared by adding 5 μL of WS to 50 μL blank surrogate serum. Unknow samples were added 5 μl DMSO. All calibrator standard, QCs, sample and blank wells were added 500 μL of IS working solution (2.5 ng/mL T3-13C6 and 25 ng/mL T4-13C6) in methanol, while 500 μL blank methanol was added to all double blanks. Following 400 μL supernatant transfer, sample were evaporated under N2 gas and reconstituted with 100 μL 80% methanol in water.

Figure 11A:
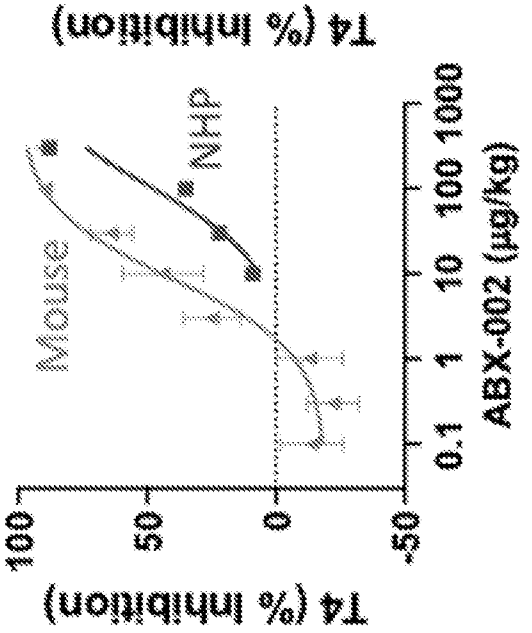
FIG. 11A depicts T4 inhibition as a function of ABX-002 dose in mice or non-human primate (NHP).
Figure 11B:
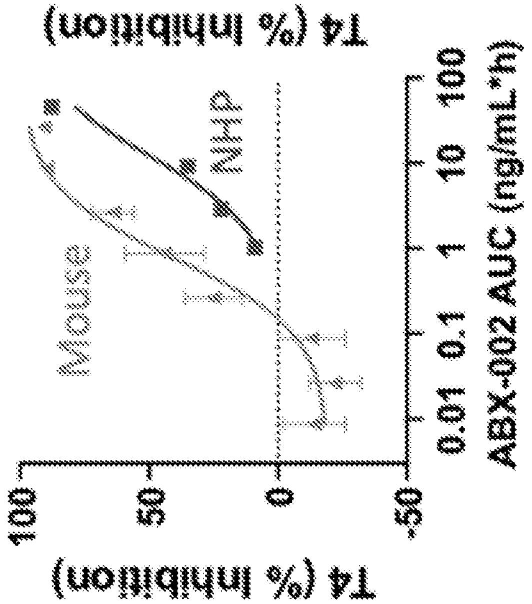
FIG. 11B depicts T4 inhibition as a function of plasma ABX-002 prodrug AUC in mice or non-human primate (NHP).
Figure 11C:
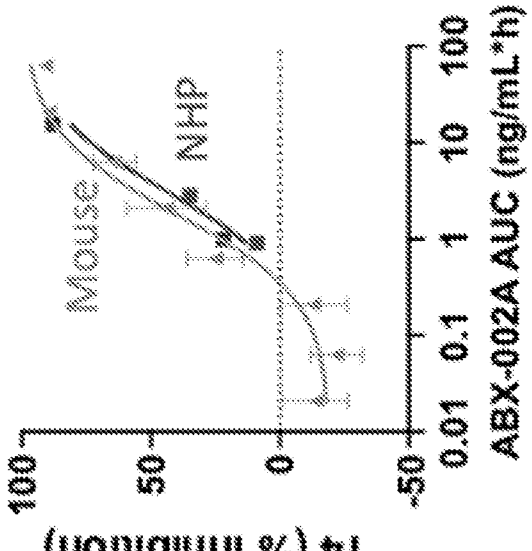
FIG. 11C depicts T4 inhibition as a function of plasma ABX-002A active metabolite AUC in mice or non-human primate (NHP).

FIGS. 11A, 11B, and 11C show $T_4$ inhibition as a function of (A) dose (B) plasma prodrug AUC or (C) plasma active metabolite AUC after 7 days of treatment in mice (orange) or non-human primate, NHP, (blue). Day 7 T4 levels normalized to the day 1 levels for each animal compared with the exposure in those same animals. Overall, the curves traced on FIG. 11C show the relationship between THA effects and plasma ABX-002A are present in both mice and NHP, and peripheral exposure to the active metabolite is a better predictor of effects on THA than either dose or plasma prodrug exposure.

What is claimed is:

1. A pharmaceutical composition comprising a fatty acid amide hydrolase (FAAH) cleavable prodrug of Formula (I'), or a pharmaceutically acceptable salt or solvate thereof:

Formula (I')

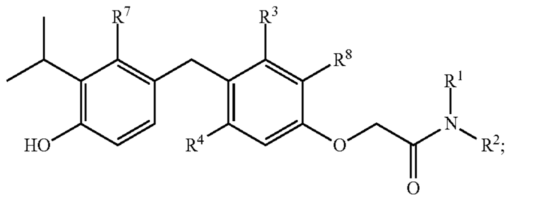

wherein:

$R^1$ and $R^2$ are independently selected from hydrogen, —$OR^5$, —$NR^5R^6$, $C_1$-$C_6$alkyl, $C_2$-$C_6$alkenyl, $C_2$-$C_6$alkynyl, $C_3$-$C_6$cycloalkyl, $C_3$-$C_6$heterocycl- oalkyl, phenyl, and —$C_1$-$C_6$alkyl-phenyl, wherein $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, phenyl, and —$C_1$-$C_6$alkyl-phenyl are optionally substituted with one or more of halo, cyano, —$OR^5$, —$NR^5R^6$, —$S(O)_2R^5$, or —$S(O)_2OR^5$;

$R^3$ and $R^4$ are independently selected from —F, —Cl, —Br, and —I;

$R^5$ and $R^6$ are independently selected from hydrogen and $C_1$-$C_6$alkyl; and $R^7$ and $R^8$ are independently selected from hydrogen, —F, —Cl, —Br, and —I;

and a pharmaceutically acceptable excipient; further comprising a peripherally restricted FAAH inhibitor.

2. The pharmaceutical composition of claim 1, or a pharmaceutically acceptable salt or solvate thereof, wherein $R^7$ is hydrogen.

3. The pharmaceutical composition of claim 1, or a pharmaceutically acceptable salt or solvate thereof, wherein $R^7$ is —F.

4. The pharmaceutical composition of claim 1, or a pharmaceutically acceptable salt or solvate thereof, wherein $R^8$ is hydrogen.

5. The pharmaceutical composition of claim 1, or a pharmaceutically acceptable salt or solvate thereof, wherein $R^8$ is —F.

6. The pharmaceutical composition of claim 1, or a pharmaceutically acceptable salt or solvate thereof, wherein $R^1$ is hydrogen.

7. The pharmaceutical composition of claim 6, or a pharmaceutically acceptable salt or solvate thereof, wherein $R^2$ is $C_1$-$C_6$alkyl optionally substituted with one or more of halo, cyano, —$OR^5$, —$NR^5R^6$, —$S(O)_2R^5$, or —$S(O)_2OR^5$.

8. The pharmaceutical composition of claim 7, or a pharmaceutically acceptable salt or solvate thereof, wherein $R^2$ is $C_1$-$C_6$alkyl substituted with one or more of halo, cyano, —$OR^5$, —$NR^5R^6$, —$S(O)_2R^5$, or —$S(O)_2OR^5$.

9. The pharmaceutical composition of claim 8, or a pharmaceutically acceptable salt or solvate thereof, wherein $R^2$ is $C_1$-$C_6$alkyl substituted with one or more-OH.

10. The pharmaceutical composition of claim 8, or a pharmaceutically acceptable salt or solvate thereof, wherein $R^2$ is $C_1$-$C_6$alkyl substituted with one or more of halo.

11. The pharmaceutical composition of claim 7, or a pharmaceutically acceptable salt or solvate thereof, wherein $R^2$ is unsubstituted $C_1$-$C_6$alkyl.

12. The pharmaceutical composition of claim 6, or a pharmaceutically acceptable salt or solvate thereof, wherein $R^2$ is phenyl optionally substituted with one or more of halo, cyano, —$OR^5$, —$NR^5R^6$, —$S(O)_2R^5$, or —$S(O)_2OR^5$.

13. The pharmaceutical composition of claim 6, or a pharmaceutically acceptable salt or solvate thereof, wherein $R^2$ is —$C_1$-$C_6$alkyl-phenyl optionally substituted with one or more of halo, cyano, —$OR^5$, —$NR^5R^6$, —$S(O)_2R^5$, or —$S(O)_2OR^5$.

14. The pharmaceutical composition of claim 1, or a pharmaceutically acceptable salt or solvate thereof, wherein $R^3$ and $R^4$ are independently selected from —F, —Cl, —Br.

15. The pharmaceutical composition of claim 14, or a pharmaceutically acceptable salt or solvate thereof, wherein $R^3$ and $R^4$ are both —Br.

16. The pharmaceutical composition of claim 14, or a pharmaceutically acceptable salt or solvate thereof, wherein $R^3$ and $R^4$ are both —Cl.

17. The pharmaceutical composition of claim 1, wherein the fatty acid amide hydrolase (FAAH) cleavable prodrug of Formula (I') has a structure selected from:

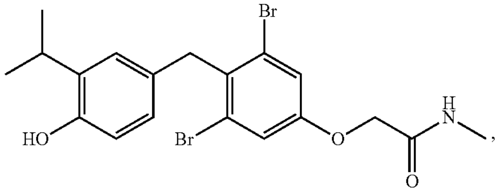

,

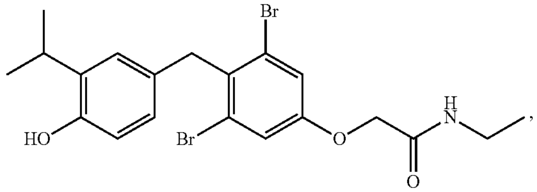

,

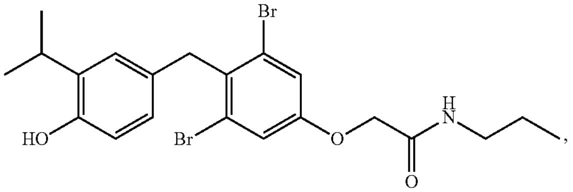

,

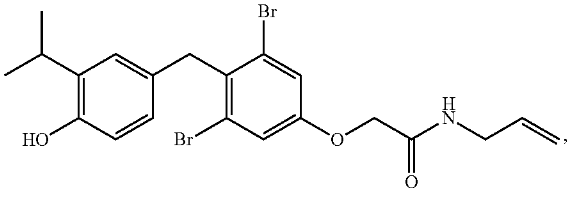

,

-continued
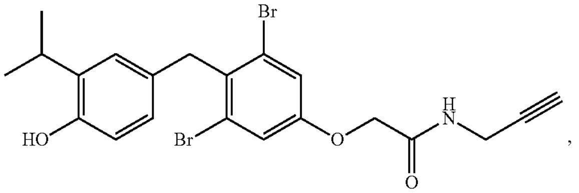
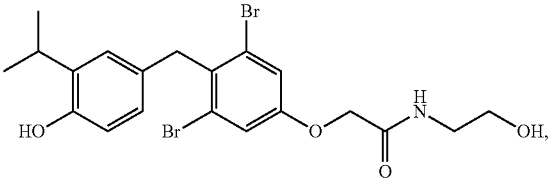
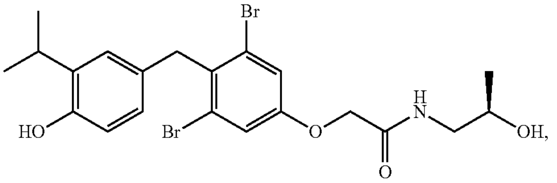
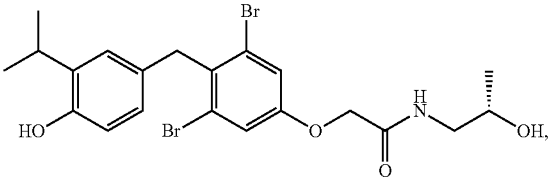
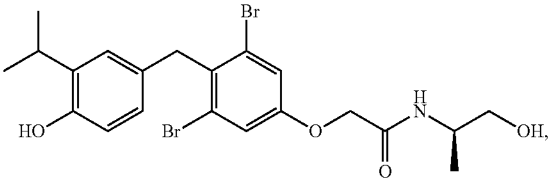
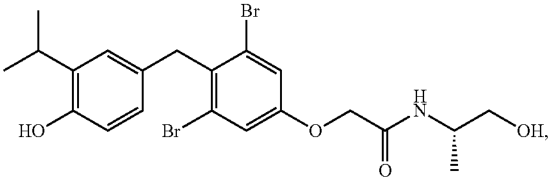
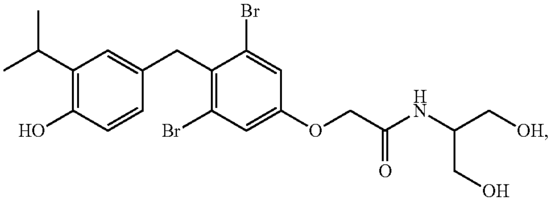
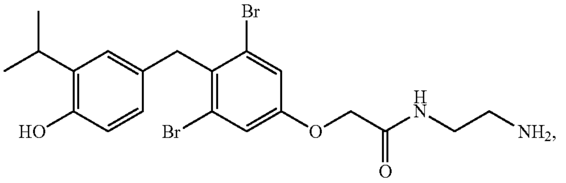
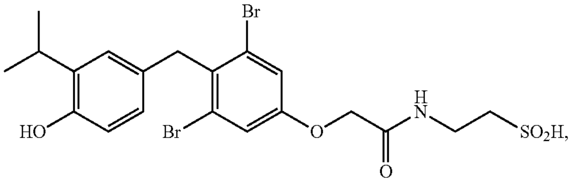
-continued
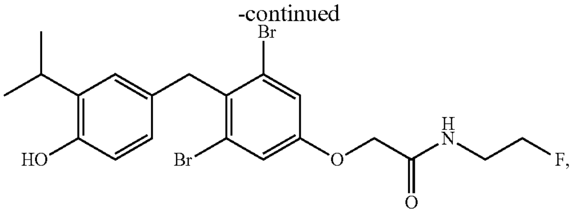
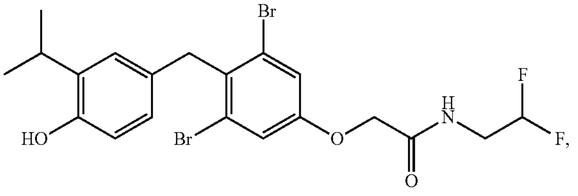
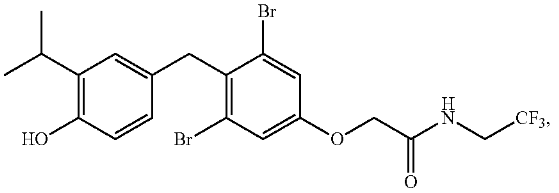
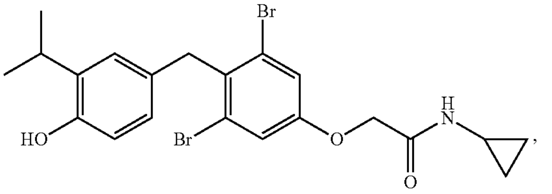
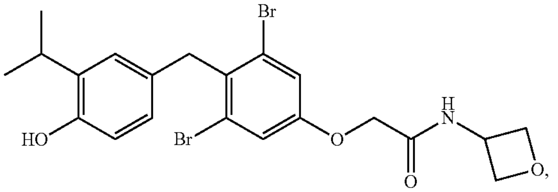
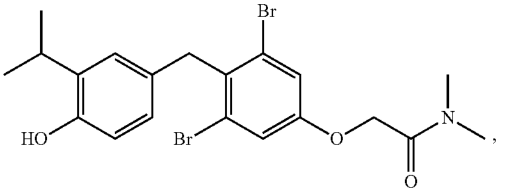
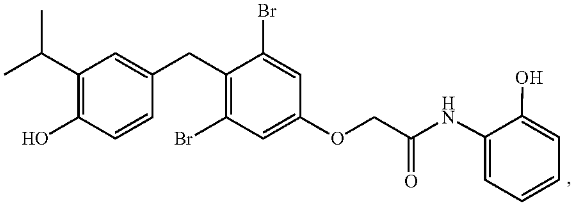
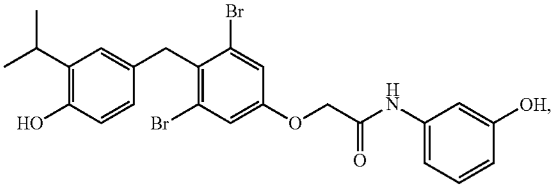
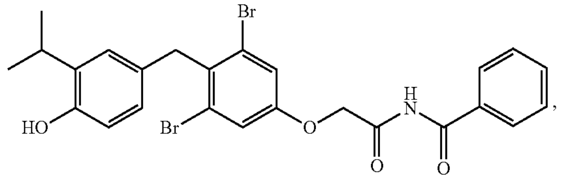

-continued
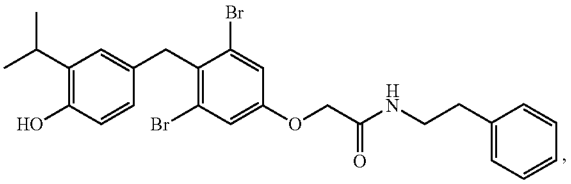
,
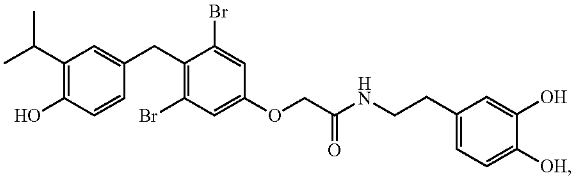
,
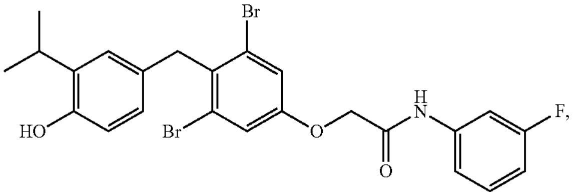
,
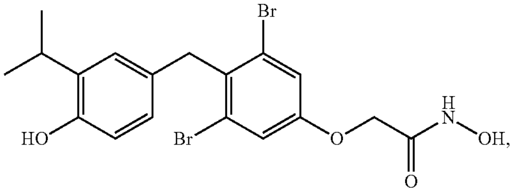
,
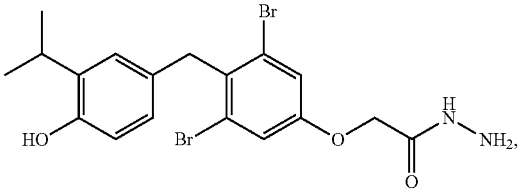
,
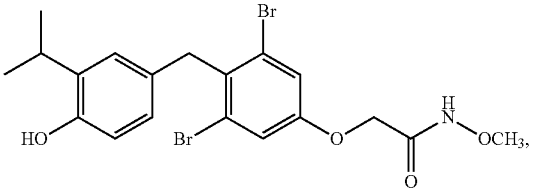
,
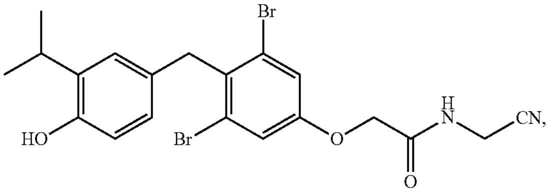
,
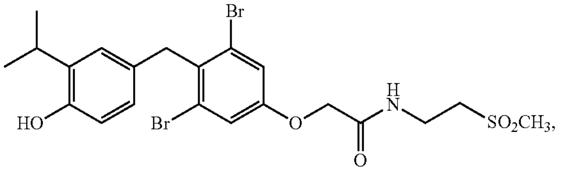
,
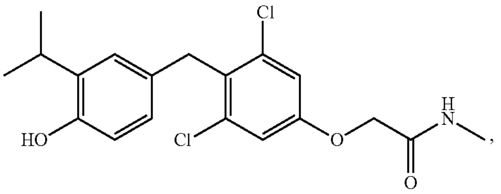
,
-continued
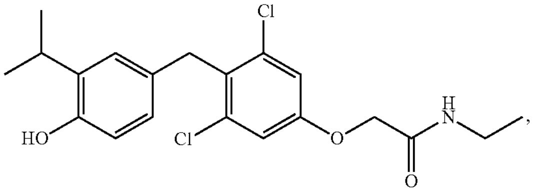
,
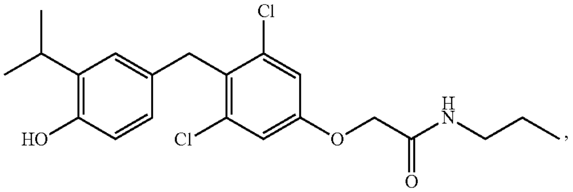
,
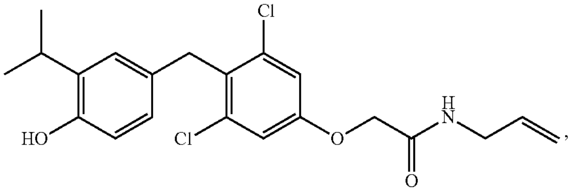
,
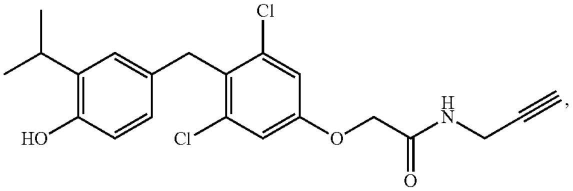
,
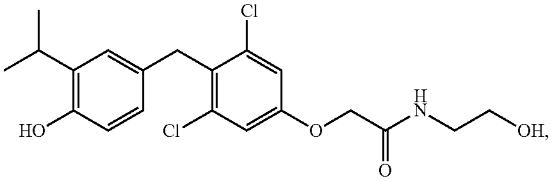
,
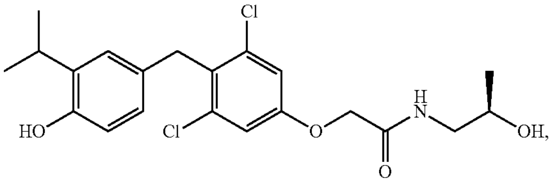
,
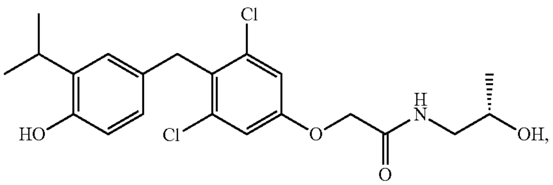
,
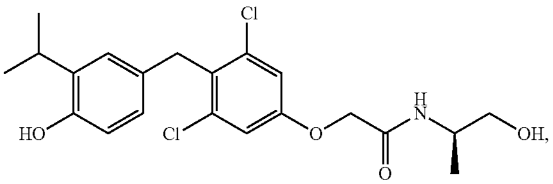
,
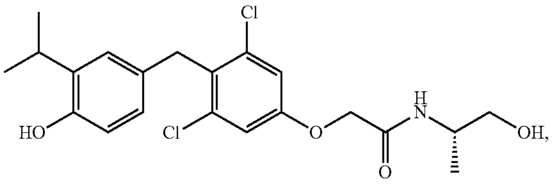
, -continued
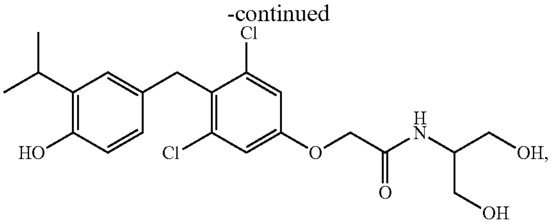
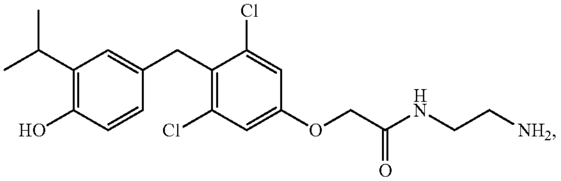
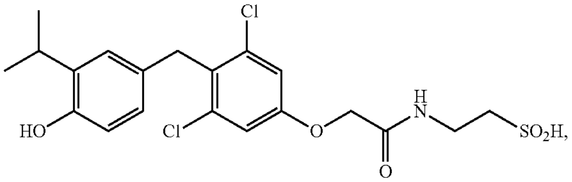
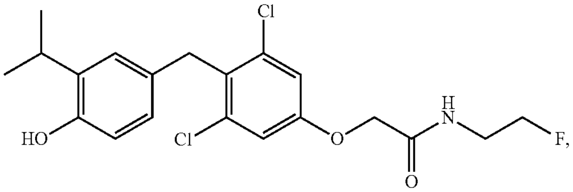
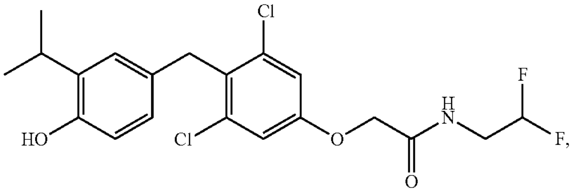
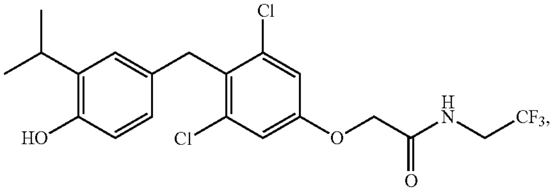
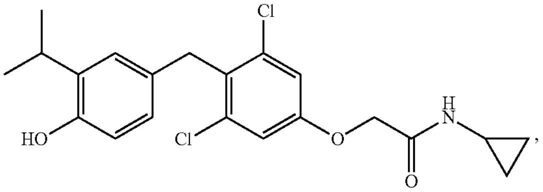
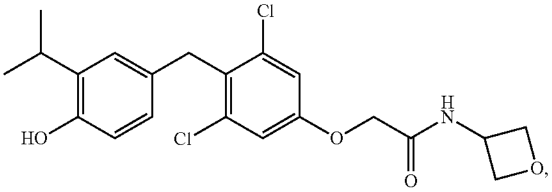
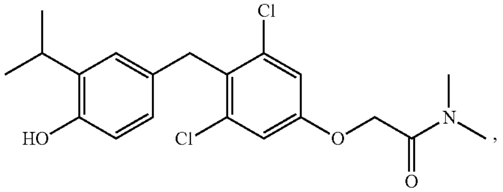
-continued
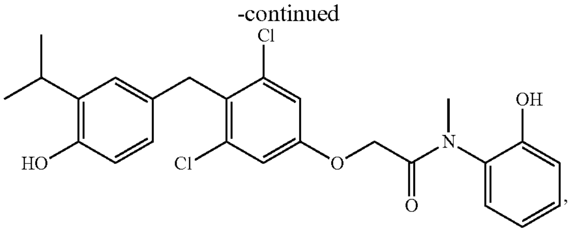
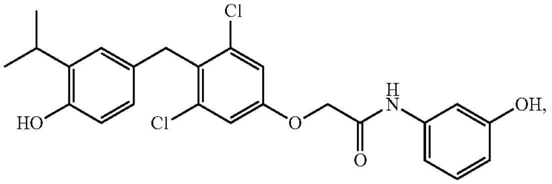
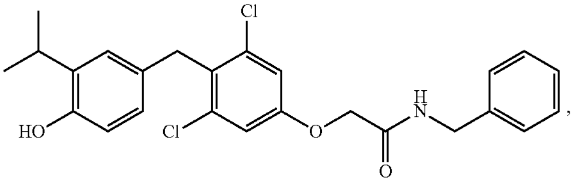
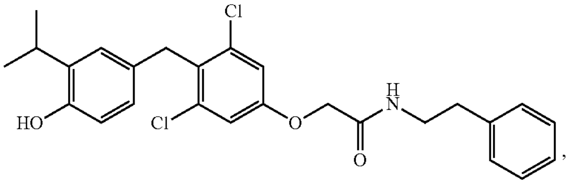
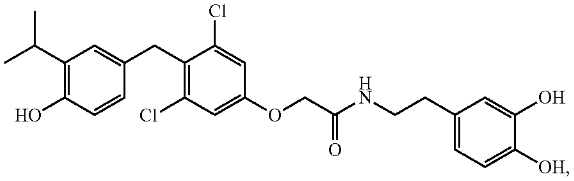
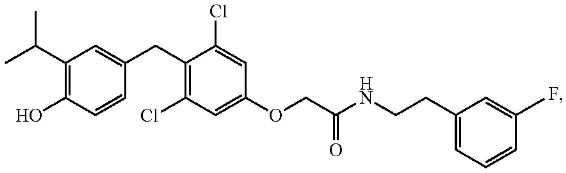
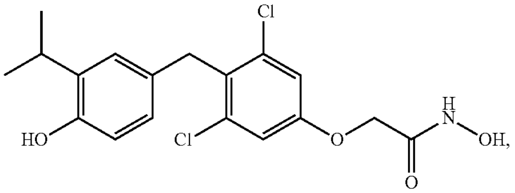
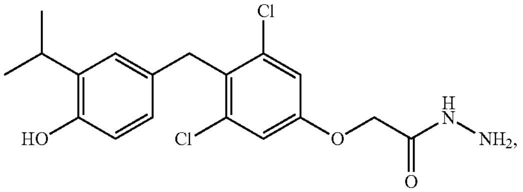
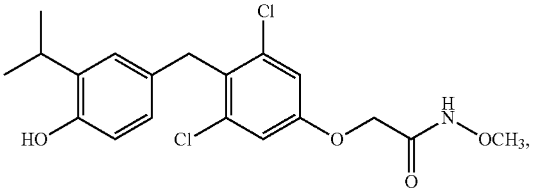

-continued
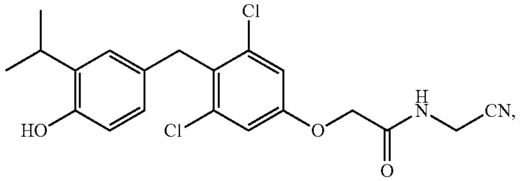
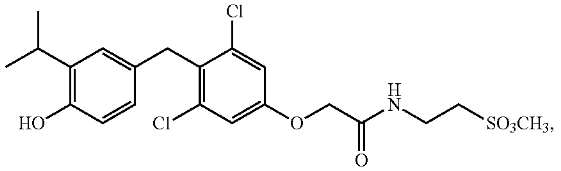
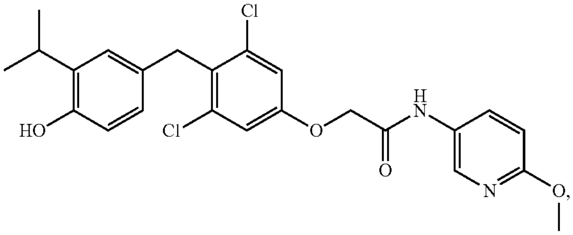
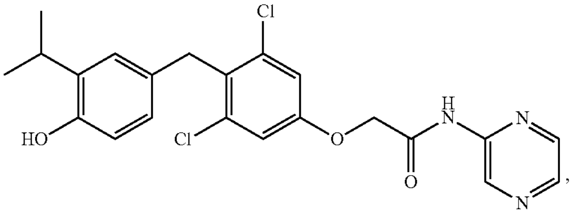
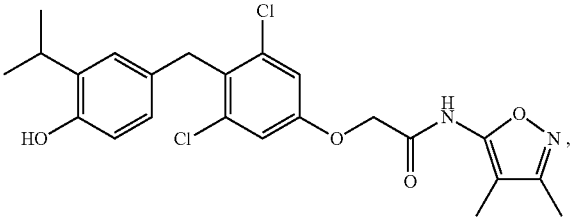
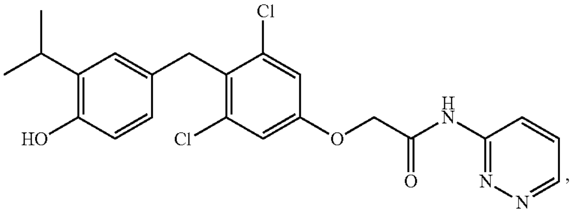
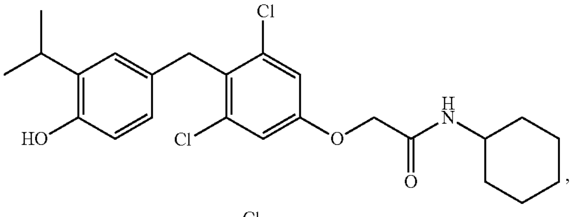
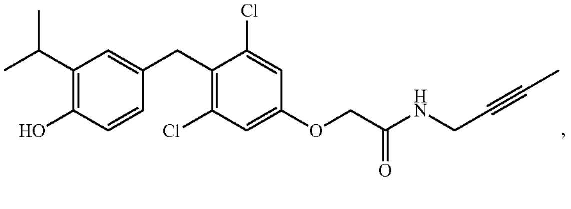
-continued
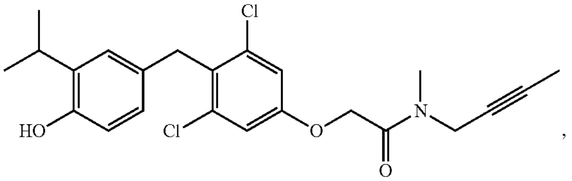
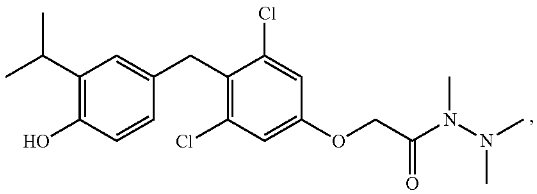
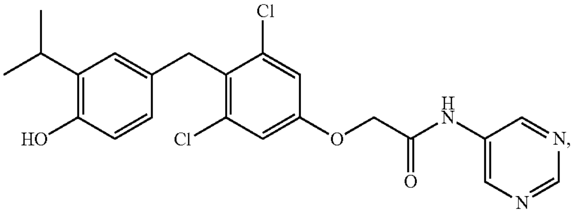
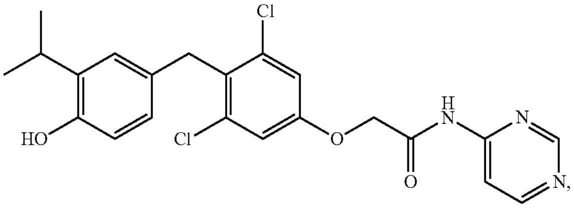
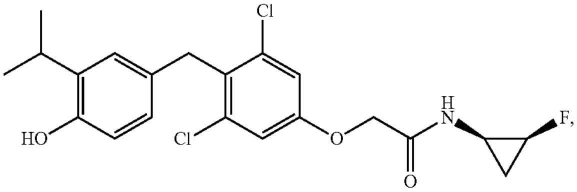
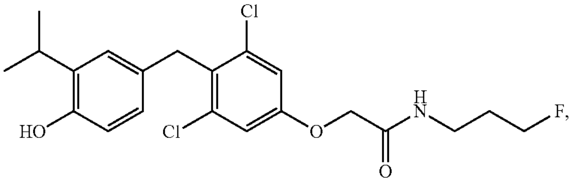
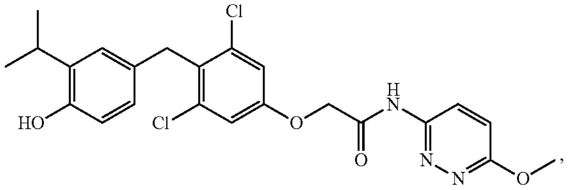
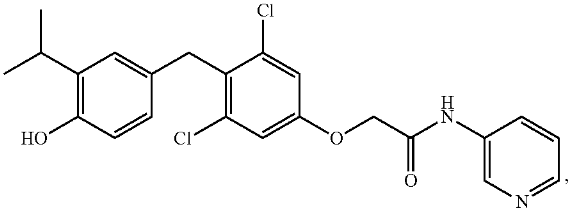

-continued
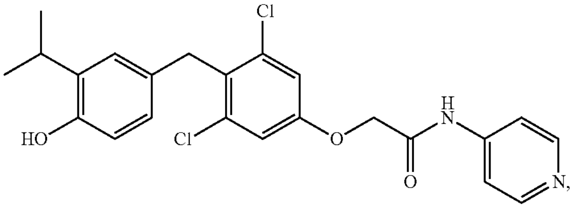,
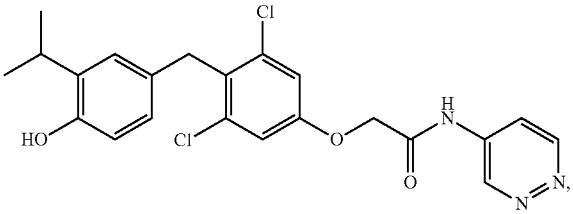,
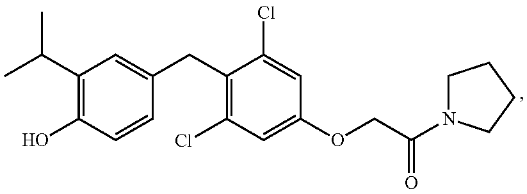,
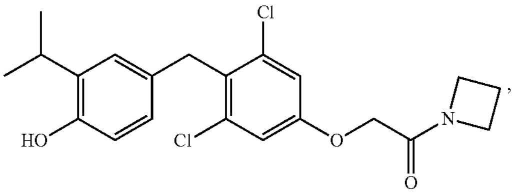,
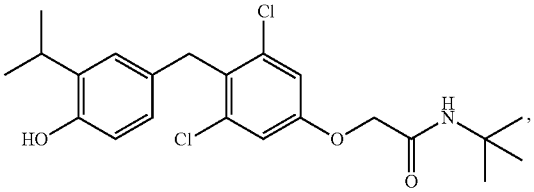,
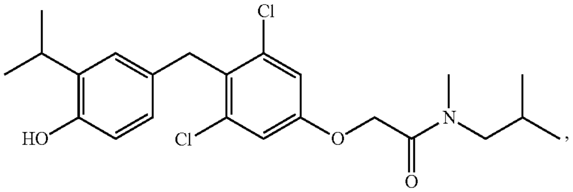,
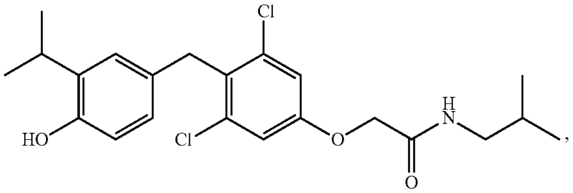,
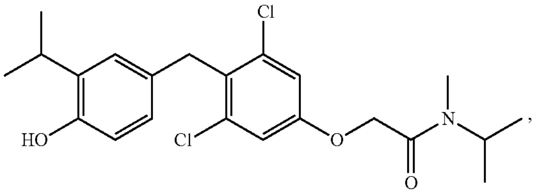,
-continued
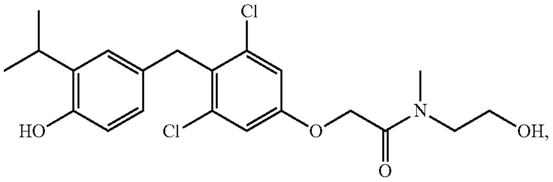,
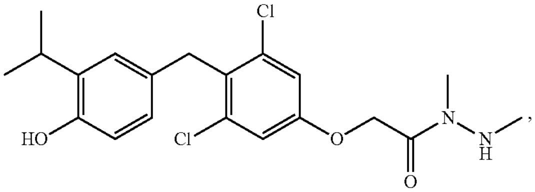,
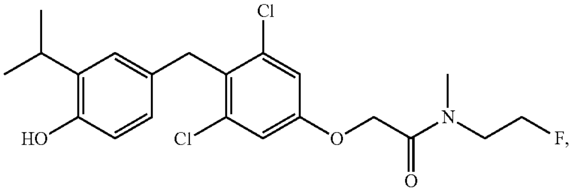,
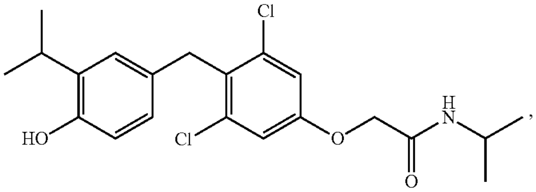,
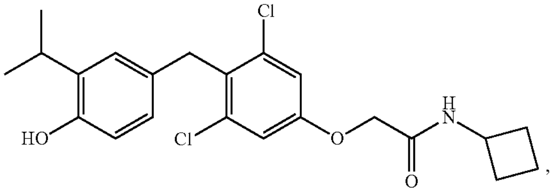,
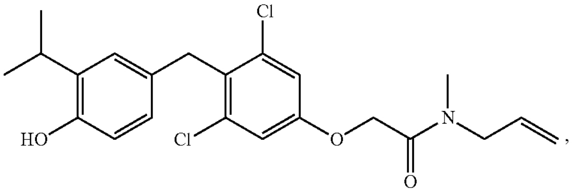,
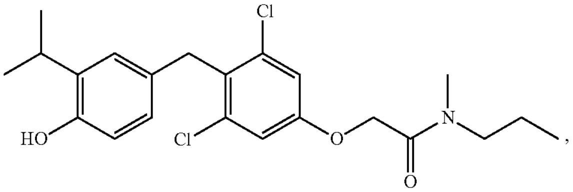,
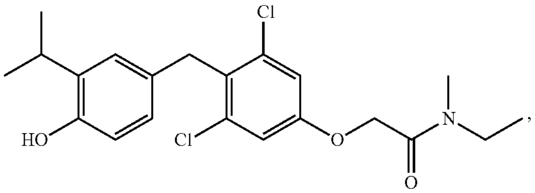,
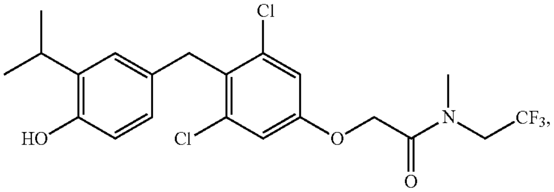, -continued
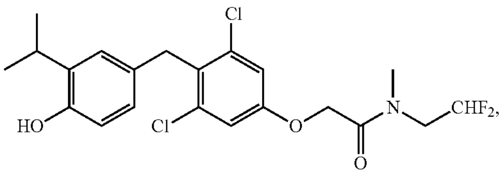
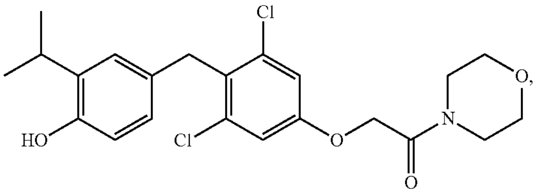
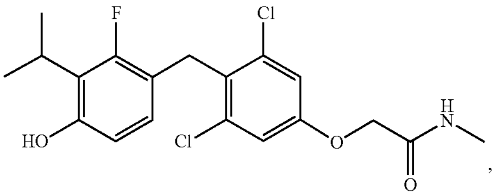
,
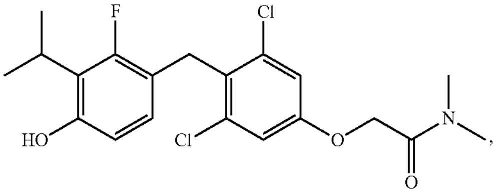
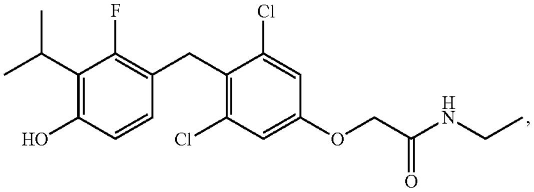
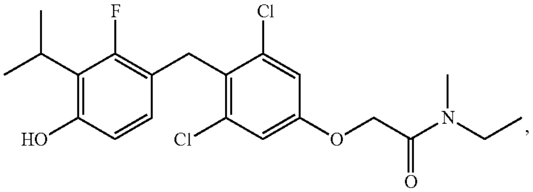
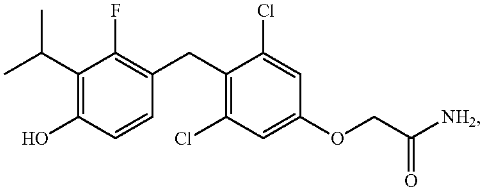
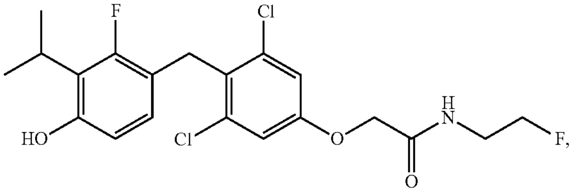
-continued
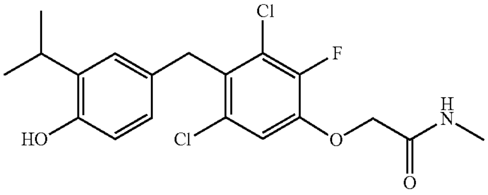
,
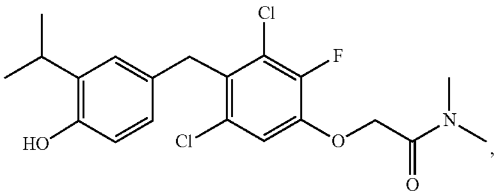
,
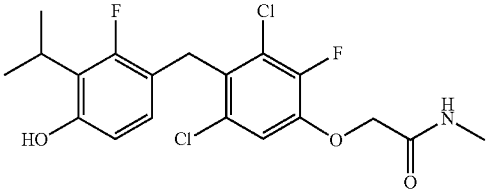
,
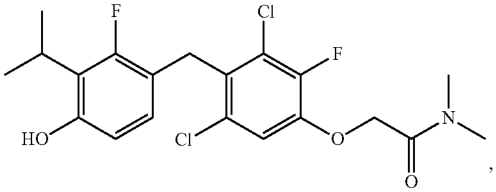
,
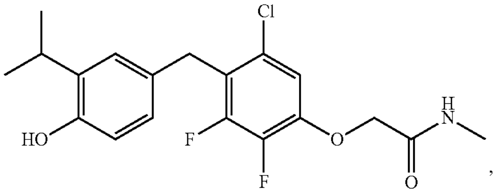
,
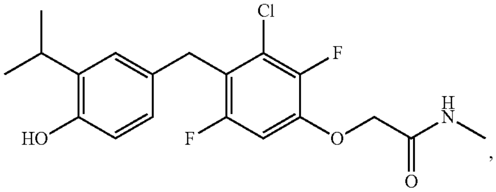
,
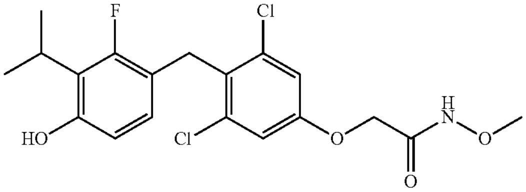
,
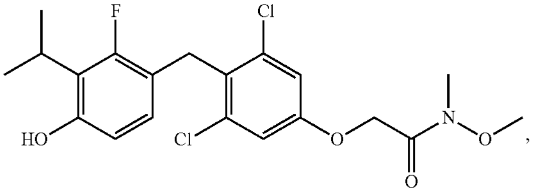
, and -continued

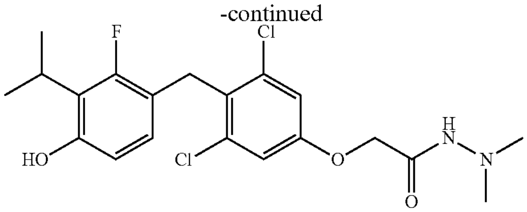

;

or a pharmaceutically acceptable salt or solvate thereof.

18. The pharmaceutical composition of claim 1, or a pharmaceutically acceptable salt or solvate thereof, wherein the peripherally restricted FAAH inhibitor is ASP-3652.

19. A method of treating a CNS disease or disorder in a patient in need thereof comprising administering to the patient a therapeutically effective amount of a pharmaceutical composition of claim 1, or a pharmaceutically acceptable salt or solvate thereof.

20. The method of claim 19, wherein the CNS disease or disorder is selected from acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (HDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephalopathy (PML), tropical spastic paraparesis (TSP), X-linked adrenoleukodystrophy (X-ALD, ALO, or X-linked ALO), and Zellweger syndrome.

* * * * *